(12) United States Patent
Lee et al.

(10) Patent No.: US 9,724,378 B2
(45) Date of Patent: Aug. 8, 2017

(54) FUSION PROTEIN COMPRISING GRANZYME B AND USE THEREOF

(71) Applicant: Samsung Electronics Co., Ltd., Suwon-si, Gyeonggi-do (KR)

(72) Inventors: Jae Il Lee, Yongin-si (KR); Hye Yoon Kang, Suwon-si (KR); Dongkyu Shin, Seongnam-si (KR); Jung Min Kim, Seoul (KR); Jungmin Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 42 days.

(21) Appl. No.: 14/716,275

(22) Filed: May 19, 2015

(65) Prior Publication Data

US 2015/0329847 A1 Nov. 19, 2015

(30) Foreign Application Priority Data

May 19, 2014 (KR) ........................ 10-2014-0060005

(51) Int. Cl.
| | |
|---|---|
| *C07K 4/00* | (2006.01) |
| *A61K 38/03* | (2006.01) |
| *C12N 9/64* | (2006.01) |
| *A61K 38/48* | (2006.01) |
| *C07K 16/28* | (2006.01) |
| *A61K 39/395* | (2006.01) |
| *A61K 38/00* | (2006.01) |

(52) U.S. Cl.
CPC ............ *A61K 38/03* (2013.01); *A61K 38/482* (2013.01); *A61K 39/3955* (2013.01); *C07K 4/00* (2013.01); *C07K 16/2863* (2013.01); *C12N 9/6467* (2013.01); *C12Y 304/21079* (2013.01); *A61K 38/00* (2013.01); *C07K 2318/20* (2013.01); *C07K 2319/00* (2013.01); *C07K 2319/01* (2013.01); *C07K 2319/035* (2013.01); *C07K 2319/33* (2013.01); *C07K 2319/50* (2013.01); *C07K 2319/70* (2013.01)

(58) Field of Classification Search
CPC ......................... C12N 9/6467; C07K 2319/00
See application file for complete search history.

(56) References Cited

U.S. PATENT DOCUMENTS

| | | |
|---|---|---|
| 7,906,628 B2 | 3/2011 | Hung et al. |
| 8,043,831 B2 | 10/2011 | Rosenblum et al. |
| 9,096,840 B2 * | 8/2015 | Rosenblum ............ C07K 16/00 |
| 2003/0054007 A1 | 3/2003 | Felgner et al. |

FOREIGN PATENT DOCUMENTS

| | | |
|---|---|---|
| JP | 2002-531113 A | 9/2002 |
| JP | 2003-531820 A | 10/2003 |
| WO | WO 00/34308 A2 | 6/2000 |

OTHER PUBLICATIONS

Kurschus et al., Delivery and therapeutic potential of human granzyme B, *Immunological Reviews*, 235 (1): 159-171 (2010).
Palm-Apergi et al., The membrane repair response masks membrane disturbances caused by cell-penetrating peptide uptake, *The FASEB Journal*, 23(1): 214-223 (2009).
Trapani et al., Functional Significance of the Perforin/Granzyme Cell Death Pathway, *Nature Reviews—Immunology*, 2: 735-747 (2002).

* cited by examiner

*Primary Examiner* — Karen Cochrane Carlson
(74) *Attorney, Agent, or Firm* — Leydig, Voit & Mayer, Ltd.

(57) ABSTRACT

A fusion protein including granzyme B, a cell penetrating peptide, a cleavage site, and a targeting moiety, a composition for cell membrane penetration comprising the fusion protein, and an anticancer composition comprising the fusion protein.

11 Claims, 11 Drawing Sheets

FIG. 5A

| Clone | NxC | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
|  |  | D | L | G | K | K | L | L | E | A | A | R | A | G | Q | D | D | E | V | R | I | L | M | A | N | G | A | D | V | N | A |
| E_01 | N3C | . | . | . | . | . | . | . | . | . | . | . | . | . | . | . | . | . | . | . | . | . | . | . | . | . | . | . | . | . | . |
| E_67 | N3C | . | . | . | . | . | . | . | . | . | . | . | . | . | . | . | . | . | . | . | . | . | . | . | . | . | . | . | . | . | . |
| E_68 | N3C | . | . | . | . | . | . | . | . | . | . | . | . | . | . | . | . | . | . | . | . | . | . | . | . | . | . | . | . | . | . |
| E_69 | N4C | . | . | . | . | . | . | . | . | . | . | . | . | . | . | . | . | . | . | . | . | . | . | . | . | . | . | . | . | . | . |
| 9_16 | N3C | . | . | . | . | . | . | . | . | . | . | . | . | . | . | . | . | . | . | . | . | . | . | . | . | . | . | . | . | . | . |
| 9_26 | N3C | . | . | . | . | . | . | . | . | . | . | . | . | . | . | . | . | . | . | . | . | . | . | . | . | . | . | . | . | . | . |
| 9_29 | N3C | . | . | . | . | . | . | . | . | . | . | . | . | . | . | . | . | . | . | . | . | . | . | . | . | . | . | . | . | . | . |
| H_14 | N3C | . | . | . | . | . | . | . | . | . | . | . | . | . | . | . | . | C | . | . | . | . | . | . | . | . | . | . | . | . | . |
| B4_01 | N4C | . | . | . | . | . | . | . | . | . | . | . | . | . | . | . | . | H | . | . | . | . | . | . | . | . | . | . | . | . | . |
| B4_02 | N3C | . | . | . | . | . | . | . | . | . | . | . | . | . | . | . | . | . | . | . | . | . | . | . | . | . | . | . | . | . | . |
| B4_07 | N3C | . | . | . | . | . | . | . | . | . | . | . | . | . | . | . | . | . | . | . | . | . | . | . | . | . | . | . | . | . | . |
| B4_33 | N3C | . | . | . | . | . | . | . | . | . | . | . | . | . | . | . | . | . | . | . | . | . | . | . | . | . | . | . | . | . | . |
| B4_45 | N3C | . | . | . | . | . | . | . | . | . | . | . | . | . | . | . | . | . | . | . | . | . | . | . | . | . | . | . | . | . | . |
| B4_50 | N4C | . | . | . | . | . | . | . | . | . | . | . | . | . | . | . | . | . | . | . | . | . | . | . | . | . | . | . | . | . | . |
| B4_58 | N5C | . | . | . | . | . | T | . | . | . | . | . | . | . | . | . | . | . | . | . | . | . | . | . | . | . | . | . | . | . | . |
| L_01 | N3C | . | . | . | . | . | . | . | . | . | . | . | . | . | . | . | . | . | . | . | . | . | . | . | . | . | . | . | . | . | . |
| L_02 | N2C | . | . | . | . | . | . | . | . | . | . | . | . | . | . | . | . | . | . | . | . | . | . | . | . | . | . | . | . | . | . |
| L_07 | N2C | . | . | . | . | . | . | . | . | . | . | . | . | . | . | . | . | . | . | . | . | . | . | . | . | . | . | . | . | . | . |
| L_11 | N3C | . | . | . | . | . | . | . | . | . | . | . | . | . | . | . | . | . | . | . | . | . | . | . | . | . | . | . | . | . | . |
| L_13 | N2C | . | . | . | . | . | . | . | . | . | . | . | . | . | . | . | . | . | . | . | . | . | . | . | . | . | . | . | . | . | . |
| L_19 | N3C | . | . | . | . | . | . | . | . | . | . | . | . | . | . | . | . | . | . | . | . | . | . | . | . | . | . | . | . | . | . |
| T_01 | N3C | . | . | . | . | . | . | . | . | . | . | . | . | . | . | . | D | . | . | . | . | . | . | . | . | . | . | . | . | . | . |
| T_02 | N3C | . | . | . | . | . | . | . | . | V | . | . | . | . | . | . | . | . | . | . | . | . | . | . | . | . | . | . | . | . | . |
| T_07 | N3C | . | . | . | . | . | . | . | . | . | . | . | . | . | . | . | . | . | . | . | . | . | . | . | . | . | . | . | . | . | . |
| T_08 | N3C | . | . | . | . | . | . | . | . | . | . | . | . | . | . | . | . | . | . | . | . | . | . | . | . | . | . | . | . | . | . |
| T_09 | N3C | . | . | . | . | . | . | . | . | . | . | . | . | . | . | . | S | . | . | . | . | . | . | . | . | . | . | . | . | . | . |
| T_16 | N3C | . | . | . | . | P | . | . | . | . | . | . | . | . | . | . | . | . | . | . | . | . | . | . | . | . | . | . | . | . | . |
| T_25 | N3C | . | . | . | . | . | . | . | . | . | . | . | . | . | . | . | . | . | . | . | . | . | . | . | . | . | . | . | . | . | . |
| T_27 | N3C | . | . | . | . | P | . | . | . | . | . | . | . | . | . | . | . | . | . | . | . | . | . | . | . | . | . | . | . | . | . |
| T_37 | N3C | . | . | . | . | . | . | . | . | . | . | . | . | . | . | . | . | . | . | . | . | . | . | . | . | . | . | . | . | . | . |
| T_40 | N3C | . | . | . | . | . | . | . | . | . | . | . | . | . | . | . | S | . | . | . | . | . | . | . | . | . | . | . | . | . | . |

N-Cap

| Clone | NxC | s | D | x | x | G | x | T | P | L | H | L | A | A | x | x | G | H | L | E | I | V | E | V | L | L | K | z | G | A | D | V | N | A |
|---|---|---|---|---|---|---|---|---|---|---|---|---|---|---|---|---|---|---|---|---|---|---|---|---|---|---|---|---|---|---|---|---|---|---|
| E_01 | N3C | Y | . | Y | I | . | W | . | . | . | . | . | . | . | D | . | . | . | . | . | . | . | . | . | . | . | . | N | . | . | . | . | . | . |
| E_67 | N3C | D | . | L | L | . | M | . | . | . | . | . | . | . | D | T | . | . | . | . | . | . | . | . | . | . | . | Y | . | . | . | . | . | . |
| E_68 | N3C | S | . | N | F | . | F | . | . | . | . | . | . | . | F | Y | . | . | . | . | . | . | . | . | . | . | . | H | . | . | . | . | . | . |
| E_69 | N4C | K | G | H | H | C | N | . | . | . | . | . | . | . | W | A | . | . | . | . | . | . | . | . | . | . | . | Y | . | . | . | . | . | . |
| 9_16 | N3C | V | . | T | D | . | I | . | L | . | . | . | . | . | Y | Y | . | . | . | . | . | . | . | . | . | . | . | H | . | . | . | . | . | . |
| 9_26 | N3C | H | . | W | N | . | W | . | . | . | . | . | . | . | K | Y | . | . | . | . | . | . | . | . | . | . | . | H | . | . | . | . | . | . |
| 9_29 | N3C | F | . | Y | . | D | N | . | . | . | . | . | . | . | D | A | . | . | . | . | . | . | . | . | . | . | . | Y | . | . | . | . | . | . |
| H_14 | N3C | N | . | W | R | . | F | . | . | . | . | . | . | . | L | N | . | . | . | . | . | . | . | . | . | . | . | N | . | . | . | . | . | . |
| B4_01 | N4C | K | . | T | W | . | D | . | . | . | . | . | . | . | L | L | . | R | . | . | . | . | . | . | . | . | . | H | . | . | . | . | . | . |
| B4_02 | N3C | Y | . | A | S | . | Y | . | L | . | . | . | . | . | R | M | . | . | . | . | . | . | . | . | . | . | . | Y | . | . | . | . | . | . |
| B4_07 | N3C | R | . | V | A | . | R | . | . | . | . | . | . | . | S | F | . | . | . | . | . | . | . | . | . | . | . | Y | . | . | . | . | . | . |
| B4_33 | N3C | N | . | Q | Y | . | Y | . | . | . | . | . | . | . | R | M | . | . | . | . | . | . | . | . | . | . | . | H | . | . | . | . | . | . |
| B4_45 | N3C | N | . | R | Y | . | Y | . | T | . | . | . | . | . | R | H | . | . | . | . | . | . | . | . | . | . | . | H | . | . | . | . | . | . |
| B4_50 | N4C | D | . | H | D | . | Y | . | . | . | . | . | . | . | D | K | . | . | . | . | . | . | . | . | . | . | . | H | . | . | . | . | . | . |
| B4_58 | N5C | H | . | S | Y | . | S | . | . | . | . | . | . | . | N | R | . | . | . | . | . | . | . | . | . | . | . | Y | . | . | . | . | . | . |
| L_01 | N3C | D | . | T | W | . | D | . | . | . | . | . | . | . | L | F | . | . | . | . | . | . | . | . | . | . | . | Y | . | . | . | . | . | . |
| L_02 | N2C | K | . | N | W | . | D | . | . | . | . | . | . | . | I | F | . | . | . | . | . | . | . | . | . | . | . | N | . | . | . | . | . | . |
| L_07 | N2C | H | . | S | W | . | D | . | . | . | . | . | . | . | T | F | . | . | . | . | . | . | . | . | . | . | . | H | . | . | . | . | . | . |
| L_11 | N3C | A | . | N | W | . | I | . | . | . | . | . | . | . | R | R | . | . | . | . | . | . | . | . | . | . | . | H | . | . | . | . | . | . |
| L_13 | N2C | N | . | L | W | . | D | . | . | . | . | . | . | . | T | R | . | . | . | . | . | . | . | . | . | . | . | Y | . | . | . | . | . | . |
| L_19 | N3C | D | . | Y | F | . | D | . | . | . | . | . | . | . | W | S | . | . | . | . | . | . | . | . | . | . | . | Y | . | . | . | . | . | . |
| T_01 | N3C | S | . | F | S | . | F | . | . | . | . | . | . | . | Y | K | . | . | . | . | . | . | . | . | . | . | . | H | . | . | . | . | . | . |
| T_02 | N3C | S | . | W | H | . | N | . | . | . | . | . | . | . | W | I | . | . | . | . | . | . | . | . | . | . | . | Y | . | . | . | . | . | . |
| T_07 | N3C | I | . | F | S | . | R | . | . | . | . | . | . | . | L | I | . | . | . | . | . | . | . | . | . | . | . | Y | . | . | . | . | . | . |
| T_08 | N3C | K | . | T | Y | . | I | . | . | . | . | . | . | . | M | N | . | . | . | . | . | . | . | . | . | . | . | N | . | . | . | . | . | . |
| T_09 | N3C | Y | . | Q | M | . | M | . | . | . | . | . | . | . | W | T | . | . | . | . | . | . | . | . | . | . | . | H | . | . | . | . | . | . |
| T_16 | N3C | Y | . | M | Q | V | N | . | . | . | . | . | . | . | W | L | . | . | . | . | . | . | . | . | . | . | . | N | . | . | . | . | . | . |
| T_25 | N3C | H | . | M | Q | . | R | . | . | . | . | . | . | . | Y | T | . | . | . | . | . | . | . | . | . | . | . | Y | . | . | . | . | . | . |
| T_27 | N3C | I | . | I | I | . | Y | . | . | . | . | . | . | . | W | S | . | . | . | . | . | . | . | . | . | . | . | N | . | . | . | . | . | . |
| T_37 | N3C | V | . | I | Q | . | R | . | . | . | . | . | . | . | W | I | . | . | . | . | . | . | . | . | . | . | . | Y | . | . | . | . | . | . |
| T_40 | N3C | I | . | F | Q | . | K | . | . | . | . | . | . | . | Q | L | . | . | . | . | . | . | . | . | . | . | . | Y | . | . | . | . | . | . |

FIG. 5D

| Clone | NxC | x | D | x | x | G | x | T P L H L A A | x | x | G H L E I V E V L L K | z | G A D V N A |
|---|---|---|---|---|---|---|---|---|---|---|---|---|---|
| E_01 | N3C | S | . | Y | I | . | D | . . . . . . . | . | . | . H N . . . . . . . . . | . H | . . . . . |
| E_67 | N3C | R | . | T | R | . | K | . . . . . . . | . | . | . R D . . . . . . . . . | . H | D . . . . |
| E_68 | N3C | F | . | M | W | . | N | . . . . . . . | . | . | . Q N . . . . . . . . . | . N | . . . . . |
| E_69 | N4C | D | . | D | E | . | Y | . . . . . . . | . | . | . D I . D . . . . . . . | . Y | . . . . . |
| 9_16 | N3C | H | . | Y | A | . | S | . . . . . . . | . | . | . N T . . . . . . . . . | . N | . . . . . |
| 9_26 | N3C | I | . | N | A | . | K | . . . . . . . | . | . | . A H . . . . . . . . . | . Y | . . . . . |
| 9_29 | N3C | S | . | R | D | . | H | . . . . . . . | . | . | . R E . . . . . . . . . | . N | . . . . . |
| H_14 | N3C | T | . | T | A | . | N | . . . . . . . | . | . | . W F . . . . . . . . . | . N | . . . . . |
| B4_01 | N4C | I | . | M | R | . | T | . . . . . . . | . | . | . P A . . . . . . . . . | . Y | . . . . . |
| B4_02 | N3C | R | . | R | F | . | S | . . . . . . . | . | . | . W H . . . . . . . . . | . H | . . . . . |
| B4_07 | N3C | V | . | Y | T | . | T | . . . . . . . | . | . | . W H . . . . . . . . . | . H | . . . . . |
| B4_33 | N3C | I | . | V | L | . | T | . . . . . . . | . | . | . W H . . . . . . . . . | . N | . . . . . |
| B4_45 | N3C | F | . | N | T | . | Q | . . . . . . . | . | . | . W H . . . . . . . . . | . Y | . . . . . |
| B4_50 | N4C | D | . | S | M | . | N | . . . . . . . | . | . | . R H . . . . . . . . . | . H | . . . . . |
| B4_58 | N5C | F | . | S | T | . | Q | . . . . . . . | . | . | . S Q . . . . . . . . . | . Y | . . . . . |
| L_01 | N3C | H | . | R | F | . | F | . . . . . . . | . | . | . S S . . . . . . . . . | . H | . . . . . |
| L_02 | N2C | | | | | | | | | | | | |
| L_07 | N2C | | | | | | | | | | | | |
| L_11 | N3C | D | . | V | Q | . | N | . . . . . T . | . | . | . H H . . . . . . . . . | . H | . . . . . |
| L_13 | N2C | | | | | | | | | | | | |
| L_19 | N3C | Q | . | Q | R | . | F | . . . . . . . | . | . | . I A . . . . . . . . . | . Y | . . . . . |
| T_01 | N3C | N | . | A | T | . | T | . . . . . . . | . | . | . K K . . . . . . . . . | . N | . . . . . |
| T_02 | N3C | T | . | H | S | . | S | . . . . . . . | . | . | . T L . . . . . . . . . | . Y | . . . . . |
| T_07 | N3C | H | . | S | A | . | S | . . . . . . . | . | . | . T K . . . . . . . . . | . Y | . . . . . |
| T_08 | N3C | L | . | N | T | . | S | . . . . . . . | . | . | . N Y . . . . . . . . . | . H | . . . . . |
| T_09 | N3C | D | . | T | H | . | A | . . . . . . . | . | . | . H T . . . . . . . . . | . Y | . . . . . |
| T_16 | N3C | E | . | S | Y | . | N | . . . . . . . | . | . | . D K . . . . . . . . . | . N | . . . . . |
| T_25 | N3C | I | . | F | T | . | H | . . . . . . . | . | . | . F R . . . . . . . . . | . H | . . . . . |
| T_27 | N3C | S | . | V | T | . | S | . . . . . . . | . | . | . D K . . . . . . . . . | . Y | . . . . . |
| T_37 | N3C | M | . | D | F | . | E | . . . . . . . | . | . | . R T . . . . . . . . . | . H | . . . . . |
| T_40 | N3C | L | . | A | R | . | I | . . . . . . . | . | . | . I H . . P . . . . . . | . Y | . . . . . |

FIG. 5E

| Clone | NxC | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| | | | | | | | | | | | | | | | 4. repeat | | | | | | | | | | | | | | | | | |
| | | | | | | | | 5 | | | 10 | | | 15 | | | 20 | | | 25 | | | 30 | | | | | | | | | |
| | | x | D | x | x | G | x | T | P | L | H | L | A | A | x | x | G | H | L | E | I | V | E | V | L | L | K | z | G | A | D | V | N | A |
| E_01 | N3C | | | | | | | | | | | | | | | | | | | | | | | | | | | | | | | | | |
| E_67 | N3C | | | | | | | | | | | | | | | | | | | | | | | | | | | | | | | | | |
| E_68 | N3C | | | | | | | | | | | | | | | | | | | | | | | | | | | | | | | | | |
| E_69 | N4C | W | . | M | Y | . | R | . | . | . | . | . | . | . | . | S | A | . | . | . | . | . | . | . | . | . | . | Y | . | . | . | . | . |
| 9_16 | N3C | | | | | | | | | | | | | | | | | | | | | | | | | | | | | | | | | |
| 9_26 | N3C | | | | | | | | | | | | | | | | | | | | | | | | | | | | | | | | | |
| 9_29 | N3C | | | | | | | | | | | | | | | | | | | | | | | | | | | | | | | | | |
| H_14 | N3C | | | | | | | | | | | | | | | | | | | | | | | | | | | | | | | | | |
| B4_01 | N4C | D | . | V | H | . | N | . | . | . | . | . | . | . | . | M | S | . | . | . | . | . | . | . | . | . | . | Y | . | . | . | . | . |
| B4_02 | N3C | | | | | | | | | | | | | | | | | | | | | | | | | | | | | | | | | |
| B4_07 | N3C | | | | | | | | | | | | | | | | | | | | | | | | | | | | | | | | | |
| B4_33 | N3C | | | | | | | | | | | | | | | | | | | | | | | | | | | | | | | | | |
| B4_45 | N3C | | | | | | | | | | | | | | | | | | | | | | | | | | | | | | | | | |
| B4_50 | N4C | N | . | F | M | . | S | . | . | . | . | . | . | . | . | W | S | . | . | . | . | . | . | . | . | . | . | H | . | . | . | . | . |
| B4_58 | N5C | S | . | R | M | . | F | . | . | . | . | . | . | . | . | Y | T | . | . | . | . | . | . | . | . | . | . | N | . | . | . | . | . |
| L_01 | N3C | | | | | | | | | | | | | | | | | | | | | | | | | | | | | | | | | |
| L_02 | N2C | | | | | | | | | | | | | | | | | | | | | | | | | | | | | | | | | |
| L_07 | N2C | | | | | | | | | | | | | | | | | | | | | | | | | | | | | | | | | |
| L_11 | N3C | | | | | | | | | | | | | | | | | | | | | | | | | | | | | | | | | |
| L_13 | N2C | | | | | | | | | | | | | | | | | | | | | | | | | | | | | | | | | |
| L_19 | N3C | | | | | | | | | | | | | | | | | | | | | | | | | | | | | | | | | |
| T_01 | N3C | | | | | | | | | | | | | | | | | | | | | | | | | | | | | | | | | |
| T_02 | N3C | | | | | | | | | | | | | | | | | | | | | | | | | | | | | | | | | |
| T_07 | N3C | | | | | | | | | | | | | | | | | | | | | | | | | | | | | | | | | |
| T_08 | N3C | | | | | | | | | | | | | | | | | | | | | | | | | | | | | | | | | |
| T_09 | N3C | | | | | | | | | | | | | | | | | | | | | | | | | | | | | | | | | |
| T_16 | N3C | | | | | | | | | | | | | | | | | | | | | | | | | | | | | | | | | |
| T_25 | N3C | | | | | | | | | | | | | | | | | | | | | | | | | | | | | | | | | |
| T_27 | N3C | | | | | | | | | | | | | | | | | | | | | | | | | | | | | | | | | |
| T_37 | N3C | | | | | | | | | | | | | | | | | | | | | | | | | | | | | | | | | |
| T_40 | N3C | | | | | | | | | | | | | | | | | | | | | | | | | | | | | | | | | |

FIG. 5F

| Clone | NxC | 5. repeat |
|---|---|---|
| | | x D x x G x T P L H L A A x x G H L E I V E V L L K z G A D V N A |
| E_01 | N3C | |
| E_67 | N3C | |
| E_68 | N3C | |
| E_69 | N4C | |
| 9_16 | N3C | |
| 9_26 | N3C | |
| 9_29 | N3C | |
| H_14 | N3C | |
| B4_01 | N4C | |
| B4_02 | N3C | |
| B4_07 | N3C | |
| B4_33 | N3C | |
| B4_45 | N3C | |
| B4_50 | N4C | |
| B4_58 | N5C | K . . F V . W . . . . . . . Y R . . . . . . . . . . H . . . . . |
| L_01 | N3C | |
| L_02 | N2C | |
| L_07 | N2C | |
| L_11 | N3C | |
| L_13 | N2C | |
| L_19 | N3C | |
| T_01 | N3C | |
| T_02 | N3C | |
| T_07 | N3C | |
| T_08 | N3C | |
| T_09 | N3C | |
| T_16 | N3C | |
| T_25 | N3C | |
| T_27 | N3C | |
| T_37 | N3C | |
| T_40 | N3C | |

FIG. 5G

| Clone | NxC | C-Cap |
|---|---|---|
| | | Q D K F G K T A F D I S I D N G N E D L A E I L Q |
| E_01 | N3C | . . . . . . . . . . . . . . . . . . . . . . . . . |
| E_67 | N3C | . . . . . . . . . . . . . . . . . . . . . . . . . |
| E_68 | N3C | . . . . . . . . . . . . . . . . . . . . . . . . . |
| E_69 | N4C | . . . . . . . . . . . . . . . . . . . . . . . . . |
| 9_16 | N3C | . . . . . . . . . . . . . . . . . . . . . . . . . |
| 9_26 | N3C | . . . . . . . . . . . . . . . . . . . . . . . . . |
| 9_29 | N3C | . . . . . . . . . . . . . . . . . . . . . . . . . |
| H_14 | N3C | . . . . . . . . . . . . . . . . . . . . . . . . . |
| B4_01 | N4C | . . . . . . . . . . . . . . . . . . . . . . . . . |
| B4_02 | N3C | . . . . . . . . . . . . . . . . . . . . . . . . . |
| B4_07 | N3C | . . . . . . . . . . . . . . . . . . . . . . . . . |
| B4_33 | N3C | . . . . . . . . . . . . . . . . . . . . . . . . . |
| B4_45 | N3C | . . . . . . . . . . . . . . . . . . . . . . . . . |
| B4_50 | N4C | . . . . . . . . . . . . . . . . . . . . . . . . . |
| B4_58 | N5C | . . . . . . . . . . . . . . . . . . . . . . . . . |
| L_01 | N3C | . . . . . . . . . . . . . . . . . . . . . . . . . |
| L_02 | N2C | . . . . . . . . . . . . . . . . . . . . . . . . . |
| L_07 | N2C | . . . . . . . . . . . . . . . . . . . . . . . . . |
| L_11 | N3C | . . . . . . . . . . . . . . . . . . . . . . . . . |
| L_13 | N2C | . . . . . . . . . . . . . . . . . . . . . . . . . |
| L_19 | N3C | . . . . . . . . . . . . . . . . . . . . . . . . . |
| T_01 | N3C | . . . . . . . . . . . . . . . . . . . . . . . . . |
| T_02 | N3C | . . . . . . . . . . . . . . . . . . . . . . . . . |
| T_07 | N3C | . . . . . . . . . . . . . . . . . . . . . . . . . |
| T_08 | N3C | . . . . . . . . . . . . . . . . . . . . . . . . . |
| T_09 | N3C | . . . . . . . . . . . . . . . . . . . . . . . . . |
| T_16 | N3C | . . . . . . . . . . . . . . . . . . . . . . . . . |
| T_25 | N3C | . . . . . . . . . . . . . . . . . . . . . . . . . |
| T_27 | N3C | . . . . . . . . . . . . . . . . . . . . . . . . . |
| T_37 | N3C | . . . . . . . . . . . . . . . . . . . . . . . . . |
| T_40 | N3C | . . . . . . . . . . . . . . . . . . . . . . . . . |

FUSION PROTEIN COMPRISING GRANZYME B AND USE THEREOF

CROSS-REFERENCE TO RELATED APPLICATIONS

This application claims the benefit of Korean Patent Application No. 10-2014-0060005 filed on May 19, 2014 in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 106,123 byte ASCII (Text) file named "720524 ST25.TXT" created May 7, 2015.

BACKGROUND OF THE INVENTION

1. Field

Provided are a fusion protein including granzyme B, a cell penetrating peptide, a cleavage site of a peptidase or protease, and a targeting moiety, a pharmaceutical composition for cell membrane penetration including the fusion protein, and an anticancer composition including the fusion protein.

2. Description of the Related Art

It has been generally required in various clinical circumstances to specifically kill a cancer cell. A number of intracellular signal transduction pathways are associated with cell death and cell survival, and thus cell death and cell survival can be controlled by controlling pathways associated with cell death and survival. The pathways can be successfully controlled by the successful delivery of a substance that restricts or blocks the pathway. A representative example of the signal transduction pathways is an apoptosis pathway. Thus, the elements related to the apoptosis pathway are useful as a target to specifically destroy a particular cell.

Granzyme B (GrB), a serine protease, is found in cytotoxic T lymphocytes (CTL) and natural killer (NK) cells. Granzyme B relates to apoptosis which is induced in a target cell when it is exposed to the contents of lysosome-type cytoplasmic granules (or lytic granules). Cytotoxic T lymphocyte granules include a series of serine proteases including perforin, a pore-forming protein, and granzymes.

In a lymphocyte-mediated cell lysis, perforin has been known to insert itself into a plasma membrane of a target cell and polymerize, forming a pore, thereby mediating the access of granzyme B into the cytoplasm of the target cell. Once granzyme B is introduced inside of a cell, it directly activates a caspase and induces rapid DNA destruction, thereby inducing cellular apoptosis.

Granzymes are structurally related to each other, but have different substrate preferences. Among the various granzymes, granzyme B has a particular activity to cleave a procaspase after an aspartic acid residue. and causes the maturation (i.e., activation) of the procapsase into caspase-3, thereby exhibiting a high cytotoxicity to a target cell inducing cellular apoptosis. Granzyme B directly activates caspases under certain conditions, directly damaging downstream caspase substrates, to trigger apoptosis.

Recently, various technologies to introduce macromolecules such as proteins into cells have been developed and are central to certain new therapies. However, exact targeting of a cell or tissue is difficult using existing technologies. In an effort to solve this problem, there have been many studies conducted regarding the cell membrane penetration of therapeutic proteins.

It has recently been found that a TAT protein of HIV-1 which is added to a cell culture medium can be delivered inside of a cell, and thus, the protein has been known as a protein transduction domain (PTD). PTD can be transferred into a cell together with other peptide or proteins which are fused thereto. Thus, there have been various attempts to transfer therapeutic drugs, peptides, and proteins into a cell using the PTD.

It is required to develop a technology for intracellular delivery of a cytotoxic substance such as granzyme B using a protein transduction domain.

BRIEF SUMMARY OF THE INVENTION

Provided is a fusion protein including granzyme B, a cell penetrating peptide (CPP), a cleavage site of a peptidase or protease, and a targeting moiety. The cell penetrating peptide may include a hydrophobic peptide and a basic peptide.

Another embodiment provides a pharmaceutical composition including the fusion protein, and a carrier.

Another embodiment provides a composition for cell membrane penetration of granzyme B including the fusion protein.

Another embodiment provides an anticancer composition including the fusion protein.

Another embodiment provides a method for intracellular delivery of granzyme B comprising administering the fusion protein to a subject in need thereof.

Another embodiment provides a method of preventing and/or treating a cancer including administering the fusion protein to a subject in need thereof.

Related compositions and methods also are provided in the following description.

BRIEF DESCRIPTION OF THE DRAWINGS

Figure 5B:
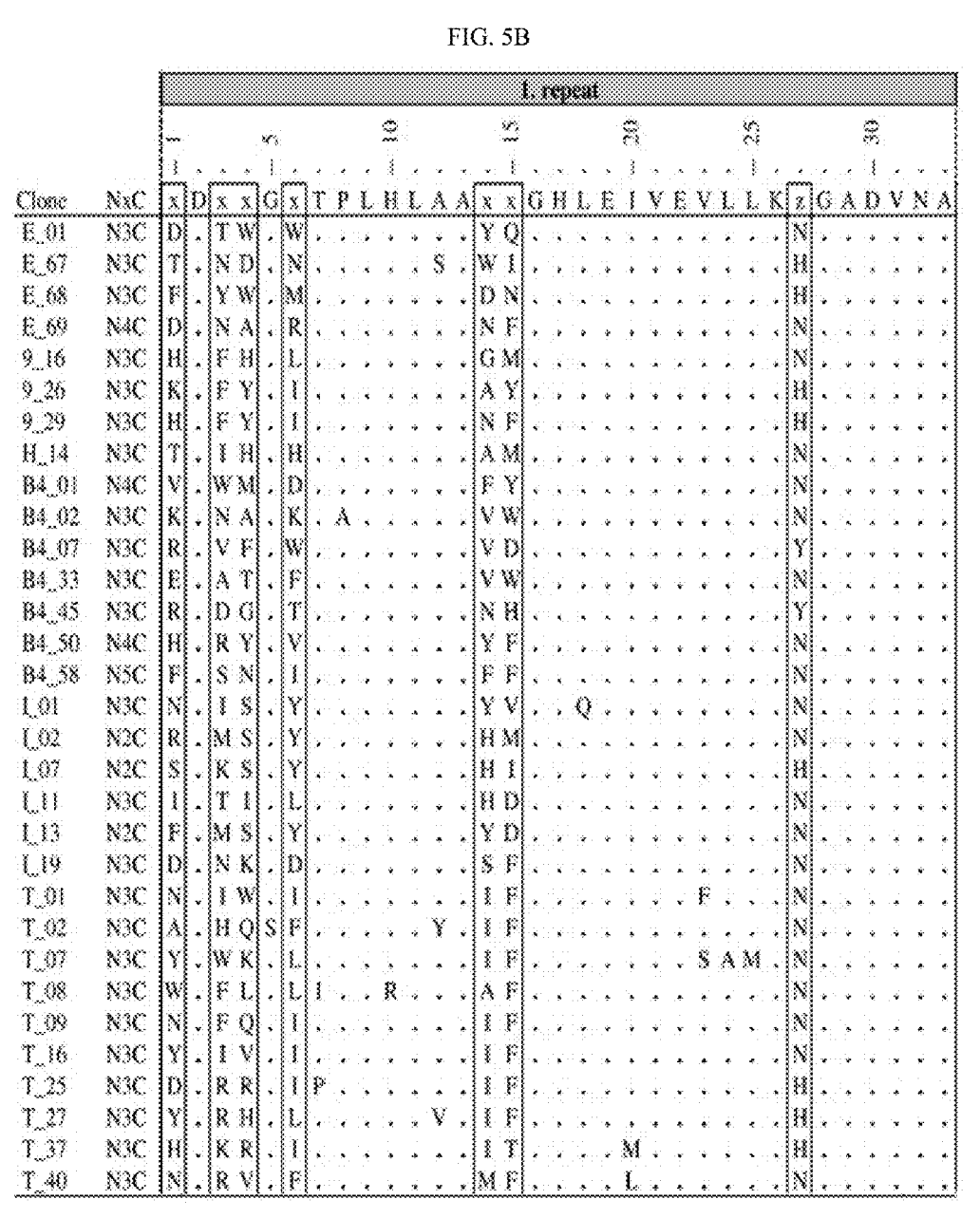

FIGS. 5A to 5G provide tables displaying nucleotide sequences of various DARPins.

DETAILED DESCRIPTION OF THE INVENTION

Figure 1:
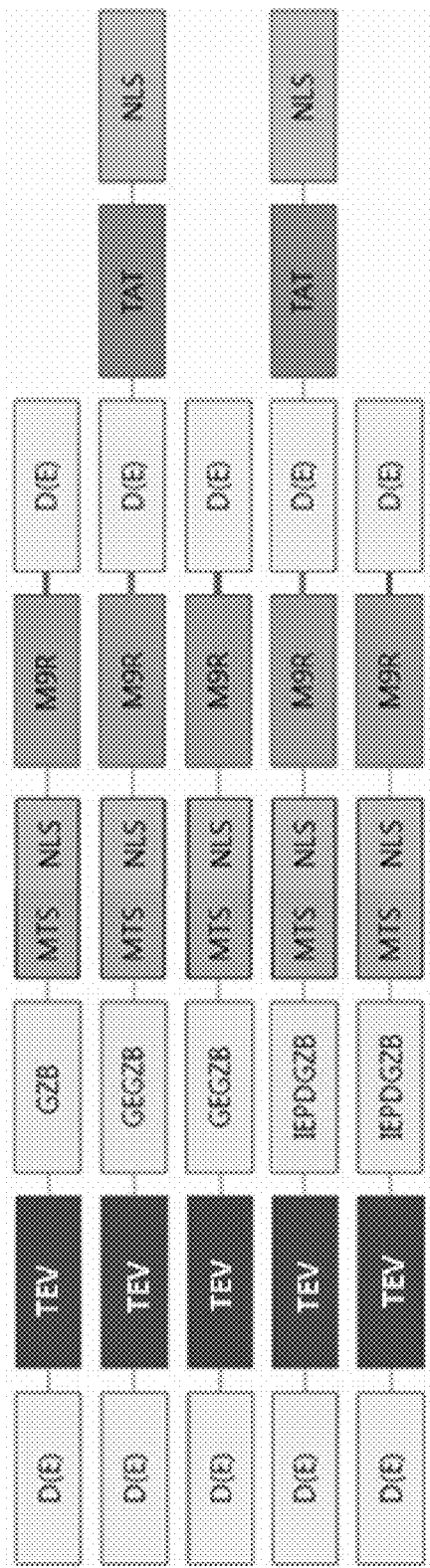
FIG. 1 is a schematic illustrating a construct of various embodiments of the fusion protein described herein.

To more effectively treat a cancer, a fusion protein for intracellular delivery of granzyme B is provided, wherein granzyme B exhibiting an anticancer effect and a cell penetrating peptide (CPP) for successfully delivering granzyme B into a cancer cell are fused (conjugated), and a more effective anticancer effect can be achieved by delivering the designed fusion protein into a cancer cell.

An embodiment provides a fusion protein comprising (1) granzyme B, (2) a cell penetrating peptide (CPP), (3) a cleavage site of a peptidase or protease, and (4) a targeting moiety.

Granzyme B, which is a serine protease, is expressed in cytotoxic T lymphocytes (CTL) and natural killer (NK) cell, and plays an important role in inducing apoptosis of a target cell in cell-mediate immune response. Granzyme B has strong cytotoxicity. It is inactivated in a normal cell, but specifically activated in a cancer cell or a virus-infected cell by being cleaved at a specific site by a specific enzyme such as cathepsin, which is rich in a cancer cell or virus-infected cell such cell, to exhibit cytotoxicity. Therefore, granzyme B is harmless to a normal cell but has specific and strong cytotoxicity to a cancer cell, and thus, it is advantageous for more effective cancer therapy with safety to a normal cell.

Granzyme B (EC number: 3.4.21.79) may be from a mammal, for example a primate (such as human, a monkey, etc.), a rodent (such as a mouse, rat, etc.), and the like. For example, granzyme B may be selected from the group consisting of a human granzyme B comprising the amino acid sequence of Accession number NP_004122 or an amino acid sequence encoded by the nucleotide sequence (mRNA) of Accession number NM_004131, and a mouse granzyme B comprising the amino acid sequence of Accession number NP_038570, or a combination thereof; but not be limited thereto.

In the fusion protein, the granzyme B may be a full-length granzyme B or a fragment of granzyme B. The fragment of granzyme B may comprise an active region (e.g., "IIGGHEAKPHSRPYMAYLMIWDQKSLKRCGGFLIQDDFVLTAAHCWGSSINVTLGAHN IKEQEPTQQFIPVKRPIPHPAYNPKNFSNDIMLLQLERKAKRTRAVQPLRLPSNKAQVKP GQTCSVAGWGQTAPLGKHSHTLQEVKMTVQEDRKCESDLRHYYDSTIELCVGDPEIKK TSFKGDSGGPLVCNKVAQGIVSYGRNNGMPPRACTKVSSFVHWIKKTMKRH": SEQ ID NO: 11) and cleavage sequence (or a cleavage inducing sequence; for example, a cathepsin cleavage sequence or an auto-cleavage (self-cleavage) sequence cleaved by auto-activation (self-activation) of granzyme B). The granzyme B is activated by cleavage by a dipeptidyl peptidase I (DPPI), which is a representative cysteine-based protease found in ribosomes, or auto-activated (self-activated). The dipeptidyl peptidase I may be cathepsin C or cathepsin H. Cathepsin C can exhibit its activity, unless (i) the amino group at the N-terminus of granzyme B is blocked, (ii) any amino acid residue of the cleavage site is proline, (iii) the amino acid residue at the N-terminus of granzyme B is lysine or arginine, or (iv) the structure of a peptide of protein disturbs cleavage (e.g., by a folding of a peptide or protein preventing the cleavage site from being exposed). The auto-activation (self-activation) of granzyme B may be induced by presence or artificial insertion of an auto-activation inducing sequence (e.g., "IEPD (SEQ ID NO: 36"). For example, the cleavage sequence in the fragment of granzyme B may be a cathepsin cleavage site (for example, a cleavage site of Dipeptidyl peptidase I) of granzyme B, such as the native granzyme B DPPI cleavage site (e.g., "GE"). Also, the cleavage sequence may be provided by a peptide comprising an amino acid sequence (auto-cleavage sequence; e.g., IEPD (SEQ ID NO: 36), etc.) which is artificially linked (e.g., a non-native peptide) to an active region of granzyme B and induces an auto-activation and cleavage of granzyme B itself whereby the cleavage sequence (e.g., IEPD) is removed. In order to be cleaved by an enzyme such as cathepsin, the cleavage sequence (peptide) may be exposed to N-terminus. Therefore, in the fragment of granzyme B, the cleavage sequence may be linked to N-terminus of the active region of granzyme B.

In an embodiment, the fragment of granzyme B may comprise:

1) an active region of granzyme B and
2) at least one cleavage sequence, for example, at least one cleavage sequence of dipeptidyl peptidase I (cleavage site recognized by dipeptidyl peptidase I) or at least one auto-cleavage sequence, wherein the cleavage sequence comprises or consists essentially of about 2 to about 20 amino acids, about 2 to about 15 amino acids, or about 2 to about 10 amino acids, comprising contiguous amino acids 'GE', 'IEPD' (SEQ ID NO: 36), or a combination thereof, wherein the cleavage site is linked to N-terminus of the active region of granzyme B.

As used herein, the term "cleavage sequence" in the fragment of granzyme B is used to be distinguished from the term "cleavage site of a peptidase or protease" positioned between a cell penetrating peptide (CPP) and a targeting moiety in a fusion protein described herein.

In order to be recognized by an enzyme such as cathepsin and activated, granzyme B may preferably have an exposed N-terminus. More specifically, the N-terminus of the cleavage sequence of granzyme B or the fragment of granzyme B should be exposed. Therefore, in the fusion protein, granzyme B or the fragment of granzyme B comprising the cleavage sequence, may be positioned at N-terminal part of the fusion protein.

The cell penetrating peptide may be any peptide capable of penetrating cell membrane, and for example, at least one selected from the group consisting of a membrane-translocation sequence (MTS) or a fragment thereof (wherein the fragment comprises 5 or more contiguous amino acid residues in the membrane-translocation sequence), a macromolecule intracellular transduction domain (MTD), TAT peptide (e.g., YGRKKRRQRRR; SEQ ID NO: 24), RKKRRQRRR (SEQ ID NO: 25)), MTD103 (LALPVLLLA; SEQ ID NO: 26), TP10 (AGYLLGKINLKALAALAKKIL; SEQ ID NO: 27), Penetratin (RQIKIWFQNRRMKWKK; SEQ ID NO: 28), MAP (model amphipathic peptide; e.g., KLALKLALKALKAALKLA (SEQ ID NO: 29)), a cell penetrating fusion peptide comprising a hydrophobic peptide and a basic peptide, or any combination thereof.

For example, the membrane-translocation sequence may comprise or consist essentially of the amino acid sequence of AAVALLPAVLLALLAP (SEQ ID NO: 12), but not be limited thereto. The fragment thereof may be a peptide comprising or consisting essentially of about 7 to about 16 contiguous amino acid residues of the amino acid sequence of SEQ ID NO: 12, and for example, a peptide comprising or consisting essentially of AAVALLP (SEQ ID NO: 13) or AVLLALLAP (SEQ ID NO: 14), but not be limited thereto.

The cell penetrating fusion peptide of a hydrophobic peptide and a basic peptide may comprise or consist essentially of:

a hydrophobic peptide comprising a total of about 5 to about 100 amino acids, about 5 to about 50 amino acids, about 5 to about 40 amino acids, or about 6 to 30 amino acids, wherein the hydrophobic peptide comprises hydrophobic amino acids at the ratio of about 60% or more, about 70% or more, about 80% or more, or about 90% or more, for example, about 60 to about 100%, about 70 to about 100%, about 80 to about 100%, or about 90 to about 100%, based on the number of the total amino acids in the hydrophobic peptide; and a basic peptide comprising a basic peptide unit comprising about 1 to about 6 basic amino acids or a repeat comprising about 2 to about 6 basic peptide units.

In the cell penetrating fusion peptide, the hydrophobic peptide may comprise a total of about 5 to about 100 amino acids, about 5 to about 50 amino acids, about 5 to about 40 amino acids, or about 6 to about 30 amino acids, and comprise a hydrophobic amino acid at the ratio of about 60% or more, about 70% or more, about 80% or more, or about 90% or more, for example, about 60 to about 100%, about 70 to about 100%, about 80 to about 100%, or about 90 to about 100%, based on the number of the total amino acids in the hydrophobic peptide. The hydrophobic amino acid may be at least one selected from the group consisting of glycine, alanine, valine, leucine, isoleucine, methionine, proline, tryptophan, phenylalanine, and the like, or any combination thereof. When the hydrophobic peptide includes one kind of hydrophobic amino acid, the hydrophobic amino acid may be included once or repeatedly. In addition, in some embodiments the hydrophobic peptide may not comprise any basic amino acid.

In an embodiment, the hydrophobic peptide may be at least one selected from the group consisting of a membrane-translocation sequence (MTS, e.g., AAVALLPAVLLAL-LAP; SEQ ID NO: 12), a fragment of the membrane-translocation sequence (for example, a peptide fragment including about 7 to about 16 consecutive amino acids within the amino acid sequence of SEQ ID NO: 1; e.g., AAVALLP (SEQ ID NO: 13), AVLLALLAP (SEQ ID NO: 14), etc.), and the like or any combination thereof.

The basic peptide may comprise or consist essentially of a basic peptide unit comprising about 1 to about 6 basic amino acids, or a repeat comprising about 2 to about 6 basic peptide units. When the basic peptide includes 2 or more basic amino acids, the basic amino acids are the same with or different from one another. If the basic peptide comprises 7 or more amino acids, the basic peptide acts as a cell penetrating peptide in itself, thereby transferring a protein (e.g., granzyme B) to an endosome, which can lead to the degradation of the protein (e.g., granzyme B). Therefore, it may be advantageous that the basic peptide includes 6 or less amino acid. The basic peptide may play a role to induce transfer of granzyme B into a nucleus.

The basic amino acid may be at least one selected from the group consisting of lysine, arginine, histidine, and the like, or any combination thereof. When the basic peptide includes two or more basic amino acids, each of the basic amino acids may be independently selected from the group consisting of lysine, arginine, histidine, and the like. When the basic peptide includes one kind of basic amino acid, the basic amino acid may be included once or repeatedly. When the basic peptide comprises about 2 to about 6 basic peptide units, the basic peptide units may be comprise the same amino acid sequence with or different basic peptide units from one another.

In a particular embodiment, the basic peptide unit may comprise lysine (K), arginine (R), or a combination thereof, in about 1 to about 6 amino acids in length. For example, the basic peptide unit may be at least one selected from the group consisting of KKKRK (SEQ ID NO: 15), KKKR (SEQ ID NO: 16), RKRK (SEQ ID NO: 17), RKRKRK (SEQ ID NO: 18), KKKKK (SEQ ID NO: 19), KKKKKR (SEQ ID NO: 20), KKKRKR (SEQ ID NO: 21), R5 (RRRRR) (SEQ ID NO: 22), R6 (RRRRRR) (SEQ ID NO: 23), and the like, or any combination thereof, but not be limited thereto.

Some of the basic peptides have been known to have a nuclear membrane penetrating activity; however, none of them has been known to have a cell membrane penetrating activity. In the present invention, the basic peptide is fused with a hydrophobic peptide, to produce a cell penetrating fusion peptide, thereby considerably increasing the cell membrane penetrating effect of the hydrophobic peptide and thus increases the cell penetrating ability of the fusion peptide comprising granzyme B.

The basic peptide may be linked (e.g., covalently) to the N-terminus or the C-terminus of the hydrophobic peptide, or respectively linked to both of the N-terminus and the C-terminus of the hydrophobic peptide (when two or more basic peptides are included). One particular embodiment, in order to more increase the cell membrane penetrability, the basic peptide may be linked to the N-terminus or the C-terminus, for example the C-terminus, of the hydrophobic peptide. When two or more basic peptides are respectively linked to both termini of the hydrophobic peptide, the basic peptides may be the same with or different from one another.

In a particular embodiment, the cell penetrating fusion peptide may comprise or consist essentially of:

a hydrophobic peptide and a basic peptide which is linked to the C-terminus of the hydrophobic peptide (that is, in the cell penetrating fusion peptide, a hydrophobic peptide is located at a N-terminal part and a basic peptide is located at a C-terminal part), or a hydrophobic peptide and a basic peptide which is linked to N-terminus of the hydrophobic peptide (that is, in the cell penetrating fusion peptide, a hydrophobic peptide is located at a C-terminal part and a basic peptide is located at a N-terminal part.

To increase the cell membrane penetrability of the cell penetrating fusion peptide, the cell penetrating fusion peptide may comprise a hydrophobic peptide and a basic peptide which is linked to the C-terminus of the hydrophobic peptide.

The cell penetrating fusion peptide may exhibit more excellent cell penetrability than pre-existing cell penetrating peptides, and thus, it may be useful in intracellular delivery of the fusion protein comprising granzyme B or a fragment thereof.

The cleavage site of a peptidase or protease may be located between the cell penetrating peptide and a targeting moiety in a fusion protein, and may be capable of being cleaved under proper conditions (e.g., presence and/or activation of the peptidase or protease). By such cleavage, a cell penetrating peptide can be released from a targeting moiety having relatively large molecular weight, whereby the cell penetrating peptide can exhibit a cell penetrating activity, thereby achieving a cell penetration and intracellular delivery of granzyme B which is attached (linked) to the cell penetrating peptide.

In order to ensure the specificity of granzyme B to a cancer cell, the cleavage site may be cleaved by a peptidase or protease present specifically in a cancer cell. The peptidase or protease present specifically in a cancer cell may be a cancer cell-specific cleavage enzyme which is secreted specifically in a cancer cell or located specifically on cell membrane of a cancer cell (e.g., exposed to outside of cell membrane), and for example, endopeptidase. The cancer cell-specific cleavage enzyme may be at least one selected from the group consisting of matrix metalloproteinase (MMP; e.g., MMP1, MMP2, MMP3, MMP7, MMP8, MMP9, MMP10, MMP11, MMP12, MMP13, MMP14, MMP15, MMP16, MMP17, MMP18, MMP19, MMP20, MMP21, MMP23A, MMP23B, MMP24, MMP25, MMP26, MMP27, MMP28, etc.), cathepsin C, cathepsin H, urokinase-type plasminogen activator (uPA), and the like, or any combination thereof. The cleavage site may be any cleavage (recognition) site of the cancer cell-specific cleavage enzyme. In a particular example, the cleavage site may be a cleavage (recognition) site of MMP9 (e.g., SGKIPRTLTA; SEQ ID NO: 35), but not be limited thereto.

The targeting moiety may be a domain capable of specifically targeting a target cell or target tissue, and for example, it may be a substance capable of targeting a specific cell such as a cancer cell or a specific tissue such as a cancer tissue. One or more targeting moieties may be incorporated into the fusion protein comprising granzyme B. For example, the targeting moiety may be comprised at both of C-terminus and N-terminus of a fusion protein comprising granzyme B, where the targeting moieties at C-terminus and N-terminus may be the same with or different to each other, but not be limited thereto. The targeting moiety may be at least one selected from the group consisting of an antibody, an antigen-binding fragment of an antibody, a protein scaffold such as a DARPin, and the like, or any combination thereof. The antibody or the protein scaffold may be one specifically recognizing or binding to at least one selected from the group consisting of signal transduction substances (e.g., various growth factors, etc.), receptors (e.g., receptor tyrosine kinase proteins, etc.), and the like, which are present or overexpressed specifically in a target cell (e.g., a cancer cell). The protein scaffold may be a protein construct characterized by having a similar structure to a protein or specifically recognizing or binding a specific protein or a specific cell. For example, the protein scaffold may be selected from the group consisting of a DARPin, an affibody, a lasso scaffold, a cyclotide, a knottin, an avimer (short for avidity multimer), a Kunitz domain, an anticalin, an adnectin, a pronectin, a fynomer, a nanofitin, an affilin, and the like, or any combination thereof, but not limited thereto.

Examples of the growth factor may selected from the group consisting of epidermal growth factor (EGF), platelet-derived growth factor (PDGF), fibroblast growth factor (FGF), vascular endothelial growth factor (VEGF), and the like. Examples of the receptor tyrosine kinase protein may include receptors of various growth factors, and for example, be selected from the group consisting of an ErbB family such as epidermal growth factor receptor (EGFR), HER2, HER3, etc., insulin receptor, platelet-derived growth factor receptor (PDGFR), fibroblast growth factor receptor (FGFR), vascular endothelial growth factor receptor (VEGFR), hepatocyte growth factor receptor (HGFR) such as c-Met, tropomyosin-receptor-kinase (Trk) receptor, Ephrin (Eph) receptor, AXL receptor, Leukocyte receptor tyrosine kinase (LTK) receptor, TIE receptor, receptor tyrosine kinase-like orphan (ROR) receptor, discoidin domain receptor (DDR), RET receptor, KLG receptor, related to receptor tyrosine kinase (RYK) receptor, Muscle-Specific Kinase (MuSK) receptor, and the like.

The antibody may be from any subtype immunoglobulin (IgA, IgD, IgE, IgG (IgG1, IgG2, IgG3, IgG4), or IgM), which recognizes at least one selected from the group consisting of various signal transduction substances, various receptors, and the like, present or overexpressed specifically in a target cell, as an antigen. The antigen-binding fragment may be a polypeptide comprising a part of an antibody, which is responsible for specific binding to the antigen. The antigen-binding fragment may be a heavy chain CDR (complementarity determining region), a light chain CDR, a heavy chain variable region, a light chain variable region, or a combination thereof (e.g., scFv, (scFv)2, scFv-Fc, Fab, Fab', or F(ab')2). In a particular embodiment, the targeting moiety may be an antigen-binding fragment of an antibody, such as scFv or scFv-Fc.

DARPin (designed ankyrin repeat protein) refers to an antibody mimetic protein having high specificity and high binding affinity to a target protein, which is prepared via genetic engineering. DARPin is originated from natural ankyrin protein, and has a structure comprising at least 2 ankyrin repeat motifs, for example, comprising at least 3, 4 or 5 ankyrin repeat motifs. The DARPin can have any suitable molecular weight depending on the number of repeat motifs. For example, the DARPins including 3, 4 or 5 ankyrin repeat motifs may have a molecular weight of about 10 kDa, about 14 kDa, or about 18 kDa, respectively. DARPin includes a structural core that provides structure and a target binding portion that resides outside of the core and binds to a target. The structural core includes a conserved amino acid sequence and the target binding portion includes an amino acid sequence that differs depending on the target.

Since the DARPin has high affinity to an antigen (target), and higher stability and smaller molecular weight, it has advantageous properties (such as pharmacokinetic (PK) properties in the living body) and stability in the living body. In addition, the DARPin can be readily fused with other proteins. Therefore, the DARPin can be useful in preparing a fusion protein having excellent properties such as increased stability in vivo The fusion protein may comprise at least one DARPin, for example, about 1 to about 10, about 1 to about 5, or about 1 to about 3 DARPins, which include the same amino acid sequence, or at least two kinds of DARPins, for example, about 2 to about 10, about 2 to about 5, or about 2 to about 3 kinds of DARPins, which include different amino acid sequences and target the same or different antigens.

Examples of DARPins are summarized in the following table and the nucleotide sequences thereof are illustrated in FIGS. 5A to 5G and SEQ ID NOs: 37-68:

| Target protein | DARPins |
| --- | --- |
| Human IgG1-Fc | I__01/02/07/11/13/19 |
| TNF-alpha | T__01/02/07/08/09/16/25/27/37/40 |
| ErbB1 (EGFR) | E__01/67/68/69 |
| ErbB2 (1-509) | 9__16/26/29 |
| ErbB2 (1-631) | H__14 |
| ErbB4 | B4__01/02/07/33/45/50/58 |
| CitS | cp34__15/16 |

In an embodiment, the targeting moiety may be an anti-EGFR DARPin which targets EGFR. The anti-EGFR DARPin may be any DARPin having DARPin's own unique structure and specifically binding to EGFR. For example, the anti-EGFR DARPin may be at least one selected from the group consisting of the following 4 anti-EGFR DARPins:

```
anti-EGFR DARPin-01 (SEQ ID NO: 30):
dlgkklleaaragqddevrilmangadvnaddtwgwtplhlaayqg hleivevllkngadvnaydyigwtplhlaadghleivevllkngad vnasdyigdtplhlaahnghleivevllkhgadvnaqdkfgktafd isidngnedlaeilq anti-EGFR DARPin-67 (SEQ ID NO: 31):
dlgkklleaaragqddevrilmangadvnatdndgntplhlsawig hleivevllkhgadvnaddllgmtplhlaadtghleivevllkyga
```

-continued dvnardtrgktplhlaardghleivevllkhdadvnaqdkfgktaf disidngnedlaeilq anti-EGFR DARPin-68 (SEQ ID NO: 32):
dlgkklleaaragqddevrilmangadvnafdywgmtplhlaadng hleivevllkhgadvnasdnfgftplhlaafyghleivevllkhga dvnafdmwgntplhlaaqnghleivevllkngadvnaqdkfgktaf disidngnedlaeilq anti-EGFR DARPin-69 (SEQ ID NO: 33):
dlgkklleaaragqddevrilmangadvnaddnagrtplhlaanfg hleivevllkngadvnakghhcntplhlaawaghleivevllkyga dvnadddegytplhlaadigdleivevllkygadvnawdmygrtpl hlaasaghleivevllkygadvnaqdkfgktafdisidngnedlae ilq In the fusion protein, granzyme B may be located so that it is exposed at N-terminus of the fusion peptide, in order to be activated by an enzyme specifically present in a cancer cell, and the cleavage site of a peptidase or protease may be located between a cell penetrating peptide and targeting moiety, and cleaved when specifically reaching a cancer cell by the targeting moiety, thereby releasing the cell penetrating peptide from the targeting moiety to activate a cell membrane penetrating activity of the cell penetrating peptide. In addition, granzyme B may be linked to the cell penetrating peptide so that it penetrates through a cell membrane together with the activated cell penetrating peptide and moves inside of a cell. Therefore, the fusion protein may comprise or consist essentially of, in order from N-terminus to C-terminus, (1) granzyme B, (2) a cell penetrating peptide (CPP), (3) a cleavage site of a peptidase or protease, and (4) a targeting moiety. As described above, when granzyme B is a fragment of granzyme B comprising an active region of granzyme B and a cleavage sequence, the fusion protein may comprise or consist essentially of, in order from N-terminus to C-terminus, (1') a fragment of '(a cleavage sequence)-(an active region of granzyme B)', (2) a cell penetrating peptide (CPP), (3) a cleavage site of a peptidase or protease, and (4) a targeting moiety.

The components of a fusion protein (i.e., granzyme B, a cell penetrating peptide, a cleavage site of a peptidase or protease, and a targeting moiety), or a hydrophobic peptide and a basic peptide of a cell penetrating fusion peptide, may be independently linked to each other through a peptide linker or directly linked to each other with no linker. The peptide linker may be a peptide comprising about 1 to about 20 amino acids or about 2 to about 10 amino acids. The peptide linker may comprise at least one amino acid residue, and when the peptide linker comprises two or more amino acid residues, each residue may be independently selected from the group consisting of Gly, Asn, Ser, Thr, Ala, and the like. For example, the peptide linker may be (GS)n (wherein n is an integer from 1 to 5), but not be limited thereto. Several appropriate amino acid sequences usefully employed as the peptide linker are well known to the relevant art.

Each of the components may be linked to each other via a covalent bond such as a peptide bond, which is generally present in a protein.

granzyme B comprised in a fusion protein has a very strong cytotoxicity, allowing to effectively kill cancer cells, however it may exhibit a fatal cytotoxicity to normal cells. Therefore, a targeting to a cancer cell and a target-specific activity of granzyme B are very important in the fusion protein. For this, the fusion protein employs a multiple safety mechanism for a cancer cell specific activation of granzyme B, comprising (1) a targeting to a cancer cell by a targeting moiety, (2) a cancer cell specific cleavage at a cleavage site and an activation of a cell penetrating peptide by such cleavage, and (3) a use of granzyme B, which is activated by cathepsin present specifically in or by itself a cancer cell. Therefore, the fusion protein can achieve an increased efficacy of granzyme B in delivery to a cancer cell, cancer cell specific cell membrane penetration, and/or intracellular delivery into a cancer cell, and thus, it can be useful for intracellular delivery of granzyme B or for killing a cancer cell.

Another embodiment provides a pharmaceutical composition comprising a fusion protein and a carrier.

Another embodiment provides a composition for cell membrane penetration of granzyme B, comprising a fusion protein. Another embodiment provides a composition for intracellular delivery of granzyme B, comprising a fusion protein. The cell to which the composition is delivered may be a cell of a diseased region such as a cancer cell.

Another embodiment provides a method for intracellular delivery (or cell membrane penetration) of granzyme B using a fusion protein. The method for intracellular delivery or cell membrane penetration may comprise administering a fusion protein to a subject in need of intracellular delivery or cell membrane penetration of granzyme B.

An embodiment provides an anticancer composition comprising a fusion protein as an active ingredient. Another embodiment provides a method of preventing and/or treating a cancer comprising administering a fusion protein to a subject in need of preventing and/or treating a cancer. In the method, the fusion protein may be administered in a pharmaceutically effective amount. The method may further comprise a step of identifying a subject in need of preventing and/or treating a cancer, prior to the step of administering. The step of identifying may comprise determining whether or not a subject needs prevention and/or treatment of a cancer (e.g., a subject is suffered from a cancer).

The subject may be any animal selected from mammals such as primates including human, monkeys, etc., rodents including rats, mice, etc., and the like; a cell, a tissue, or body fluid (e.g., blood, serum) derived (isolated) from the animal; or a culture thereof. The subject may be an animal, or a cell, a tissue, or body fluid derived (isolated) from the animal, which is in need of delivery (e.g., intracellular delivery) of granzyme B included in the fusion protein.

The fusion protein may be administered to a subject in need of administration of granzyme B, via oral or parenteral route, or administered by being contacted with a cell, tissue, or body fluid isolated from the subject.

The fusion protein or the pharmaceutically composition may further include a pharmaceutically acceptable carrier. The pharmaceutically acceptable carrier may be any one that is commonly used in formulation of nucleic acid containing drugs, and may be, but not limited to, at least one selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, mineral oil, and the like. The pharmaceutically composition may further include at least one selected from the group consisting of a diluent, an excipient, a lubricant, a wetting agent, a sweetener, a flavor enhancer, an emulsifying agent, a suspension agent, a preservative, and the like.

The fusion protein or the pharmaceutically composition may be administered via oral or parenteral route. Parenteral administration may be performed by intravenous injection, subcutaneous injection, muscular injection, intraperitoneal injection, endothelial administration, local administration, intranasal administration, intrapulmonary administration, and/or rectal administration. Since oral administration leads to digestion of proteins or peptides, an active ingredient in the compositions for oral administration must be coated or formulated to prevent digestion in stomach.

In addition, the fusion protein may be in a form of solution in oil or an aqueous medium, suspension, syrup, or emulsifying solution form, or may be formulated into a form of an extract, powders, granules, a tablet or a capsule. The cell membrane penetrating conjugate may further include a dispersing agent and/or a stabilizing agent for its formulation.

Another embodiment provides a method of improving (increasing) a cell membrane penetrability of granzyme B, wherein the method comprises preparing a fusion protein comprising (1) granzyme B, (2) a cell penetrating peptide (CPP), (3) a cleavage site, and (4) a targeting moiety. Another embodiment provides a method of preparing granzyme B derivative having increased cell membrane penetrability, wherein the method comprises preparing s fusion protein comprising (1) granzyme B, (2) a cell penetrating peptide (CPP), (3) a cleavage site, and (4) a targeting moiety. The step of preparing a fusion protein may be conducted ex vivo. Each component of the fusion protein may be independently linked to each other through a peptide linker or directly linked to each other with no linker, as described above.

The preparation of the fusion protein may be performed by any general method for preparing a protein, such as a chemical synthesis of a protein, a protein expression using an expression (recombinant) vector comprising (carrying) polynucleotides encoding each component of the fusion protein (in a proper host cell), and the like. Thus, also provided herein is a polynucleotide encoding the fusion protein described herein, optionally in an expression (recombinant) vector, as well as a method of producing the fusion protein comprising expressing the polynucleotide encoding the fusion protein in a cell or culturing a recombinant cell comprising (harboring) the polynucleotide encoding the fusion protein to express the polynucleotide.

Each component of the fusion protein, i.e., granzyme B, a cell penetrating peptide, a cleavage site, and a targeting moiety, is described above.

As used herein, the term "vector" refers to a means for expressing a gene of interest in a host cell, as exemplified by a plasmid vector, a cosmid vector, and a viral vector, such as a bacteriophage vector, an adenovirus vector, a retrovirus vector and an adeno-associated virus vector. The recombinant vector may be constructed from well-known plasmids (for example, pSC101, pGV1106, pACYC177, ColE1, pKT230, pME290, pBR322, pUC8/9, pUC6, pBD9, pHC79, pIJ6l, pLAFR1, pHV14, pGEX series, pET series, pUC19, etc.), phages (for example, λgt4λB, λ-Charon, λΔz1, M13, etc.) or viruses (for example, SV40, etc.) by known manipulation (genetic engineering) techniques.

In the recombinant vector, the polynucleotide encoding the protein conjugate may be operatively linked to a promoter. The term "operatively linked" is intended to pertain to a functional linkage between a nucleotide sequence of interest and an expression regulatory element (for example, a promoter sequence) so that the expression of the nucleotide sequence of interest is governed by the regulatory element. For instance, when it is "operatively linked" to the regulatory element, the nucleotide sequence of interest can be transcribed and/or translated under the control of the regulatory element.

The recombinant vector may be constructed typically as a cloning vector or an expression vector. For recombinant expression vectors, a vector typically available for expressing a foreign protein in plant, animal or microorganism cells may be employed. Various methods well known in the art may be used for the construction of recombinant vectors.

For use in hosts, such as prokaryotic or eukaryotic cells, the recombinant vector may be constructed appropriately. For example, when a vector is constructed as an expression vector for use in a prokaryotic host, the vector typically includes a strong promoter for transcription (e.g., a pLλ promoter, a CMV promoter, a trp promoter, a lac promoter, a tac promoter, a T7 promoter, etc.), a ribosomal binding side for initiating translation, and transcriptional/translational termination sites. On the other hand, an expression vector for use in a eukaryotic host includes an origin of replication operable in a eukaryotic cell, such as, but not limited to, an f1 origin of replication, an SV40 origin of replication, a pMB1 origin of replication, an adeno origin of replication, an AAV origin of replication, a BBV origin of replication. In addition, the expression vector typically includes a promoter derived from mammalian cells (for example, metallothionein promoter) or from mammalian viruses (for example, adenovirus late promoter, vaccinia virus 7.5K promoter, SV40 promoter, cytomegalovirus promoter and tk promoter of HSV), and a polyadenylation sequence as a transcription termination sequence.

The recombinant cell may be prepared by introducing the recombinant vector into a suitable host cell. So long as it allows for the sequential cloning and expression of the recombinant vector in a stable manner, any host cell known in the art may be employed. Examples of the prokaryotic host cell available may be at least one selected from the group consisting of *E. coli* JM109, *E. coli* BL21, *E. coli* RR1, *E. coli* LE392, *E. coli* B, *E. coli* X 1776, *E. coli* W3110, *Bacillus* spp. such as *Bacillus subtilis* and *Bacillus thuringiensis*, and enterobacteriaceae strains such as *Salmonella typhimurium, Serratia marcescens*, and various *Pseudomonas* species. Eukaryotic host cells to be transformed may be at least one selected from the group consisting of *Saccharomyces cerevisiae*, insect cells, plant cells and animal cells including Sp2/0, CHO (Chinese hamster ovary) K1, CHO DG44, PER.C6, W138, BHK, COS-7, 293, HepG2, Huh7, 3T3, RIN, and MDCK, but not be limited thereto.

Using a method well known in the art, the polynucleotide or a recombinant vector carrying the polynucleotide may be introduced (incorporated) into a host cell. This transformation is carried out through $CaCl_2$ or electroporation when the host cell is prokaryotic. For eukaryotic host cells, the genetic introduction may be achieved using, but not limited to, microinjection, calcium phosphate precipitation, electroporation, liposome-mediated transfection, or particle bombardment.

To select a (recombinant vector) transformed host cell, advantage may be taken of the phenotype attributed to a selection marker according to a method known in the art. For example, when the selection marker is a gene resistant to a certain antibiotic, the host cells may be grown in the presence of the antibiotic in a medium to select a transformant of interest.

The fusion protein capable of an effective intracellular delivery of granzyme B specific to a cancer cell, and the pharmaceutical composition (anticancer composition) comprising the fusion protein may exhibit a "first-in class" anticancer activity, which is distinguished from pre-existing anticancer agents, and thus, they are expected to be useful as an effective anticancer drug. For example, pharmaceutical composition may have a large effect on almost all types of solid tumors such as lung cancer, breast cancer, etc., and be also expected to have a good effect on metastasis.

EXAMPLES

Hereafter, the present invention will be described in detail by examples.

The following examples are intended merely to illustrate the invention and are not construed to restrict the invention.

Example 1

Preparation of a Fusion Protein 1.1. Preparation of GZB-MTS-BAA-M9R-D(E) A fusion protein (amino acid sequence: SEQ ID NO: 1; nucleotide sequence: SEQ ID NO: 2), which comprises, in order from N-terminus to C-terminus, "granzyme B (GZB)-cell penetrating fusion peptide [membrane-translocation sequence (MTS)-basic amino acid (BAA)]-cleavage site (M9R)-targeting moiety [EGFR DARPin (D(E))], was prepared (the first construct in FIG. 1). The amino acid sequence of KKKRK (SEQ ID NO: 15), which is a representative nuclear transfer signal, was used as "BAA".

The nucleotide sequence of SEQ ID NO: 2 was transfected into E. coli BL21 (DE3) cell and expressed, to produce the fusion protein having the amino acid sequence of SEQ ID NO: 1. In detail, the polynucleotides were cloned to pET21b vector (Novagen) using the restriction enzymes NdeI (NEB) and XhoI (NEB) to construct recombinant vectors pET21b. These recombinant vectors were introduced into an E. coli strain (BL21 (DE3) Codon Plus-RIPL; Invitrogen).

The transfected cells were cultured in LB media. When the O.D. value of absorbance at 600 nm reaches 0.5, 1 mM of IPTG (isopropyl-β-D-thio-galactoside) was added to the cell culture, which was further cultured at 18° C. for 16 hours. The obtained cultured cells were crushed by sonication in the presence of 20 mM Tris-HCl buffer solution (pH 7.4) supplemented with 10% glycerol and 0.25M NaCl, and centrifuged at 10,000 g, to obtain a supernatant. The obtained supernatant was applied to $Ni^{2+}$-NTA superflow column (Qiagen) which is equilibrated with the buffer solution. The column was washed with a washing buffer (20 mM Tris-HCl, pH 7.4, 10% glycerol. and 1 M NaCl) in the amount of 5-fold of the column volume, and then treated with a eluting buffer (20 mM Tris-HCl, pH 7.4, 10% glycerol, 0.25 M NaCl and 0.2M imidazole), to elute the fusion protein. The fractions including the fusion protein were collected and salts comprised in the fractions were removed using Amicon Ultra-15 Centrifugal Filter (Milipore), to concentrate and purify the protein. The concentration of the purified protein was measured using BSA as a standard substance.

Figure 2:
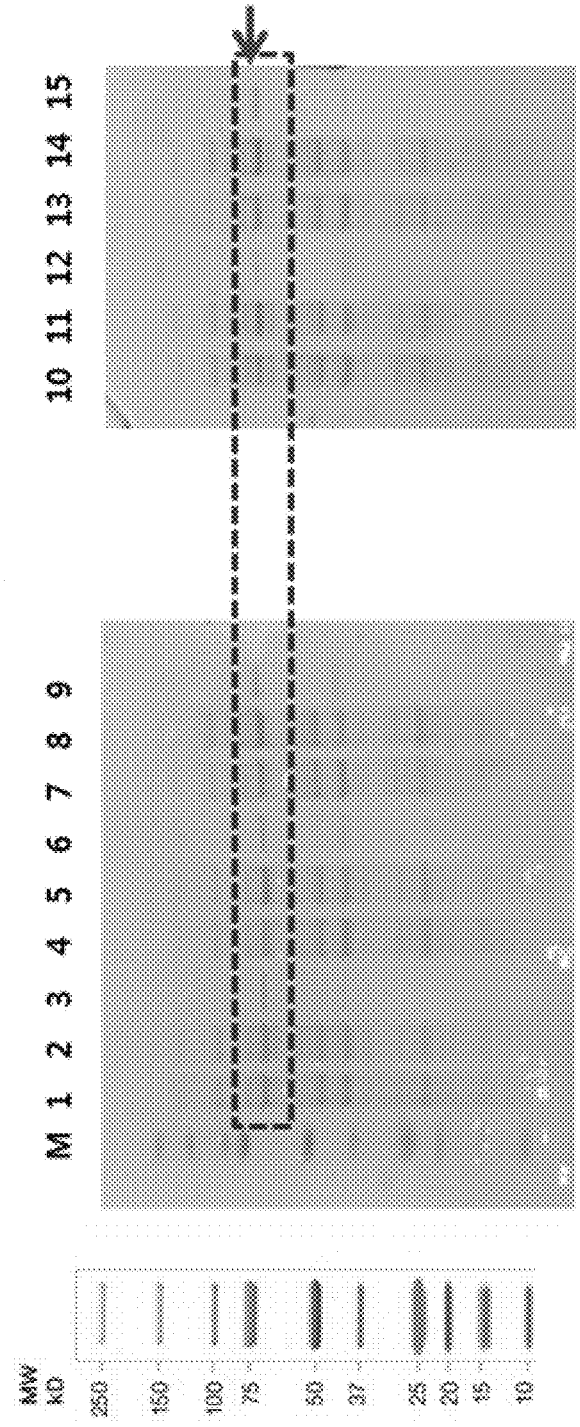
FIG. 2 illustrates immunoblotting assay results showing the expression of a fusion protein.

The expression of the fusion protein was observed through SDS-PAGE assay, and the obtained results are shown in FIG. 2.

The prepared fusion protein (SEQ ID NO: 1) and its coding nucleotide sequence (SEQ ID NO: 2) are summarized in Table 1:

TABLE 1

| N → C | Amino Acid Sequence | Nucleotide Sequence encoding the Amino Acid Sequence |
|---|---|---|
| His6 | MRGSHHHHHHDYDIPTT | ATGCGCGGCAGCCATCACCATCACCATCACGATTACG ATATCCCAACGACC |
| Dar(E) | DLGKKLLEAARAGQDDEVRI LMANGADVNADDTWGWTPL HLAAYQGHLEIVEVLLKNGA DVNAYDYIGWTPLHLAADGH LEIVEVLLKNGADVNASDYIG DTPLHLAAHNGHLEIVEVLLK HGADVNAQDKFGKTAFDISID NGNEDLAEILQ | GATCTGGGCAAAAAACTGCTGGAAGCGGCGCGCGCG GGCCAGGATGATGAAGTGCGCATTCTGATGGCGAAT GGTGCGGATGTTAACGCGGACGATACCTGGGGCTGG ACCCCACTGCATCTGGCCGCGTATCAGGGTCACCTGG AAATCGTGGAGGTGCTGCTGAAAAACGGCGCGGATG TGAACGCGTATGATTATATTGGCTGGACCCCGCTGCA TCTGGCGGCGGATGGCCATCTGGAAATTGTGGAAGT GCTGCTGAAAAACGGCGCTGATGTTAATGCTAGCGAT TATATTGGCGATACGCCGCTGCACCTGGCAGCGCATA ACGGCCATCTGGAGATTGTTGAAGTTCTGCTGAAGCA TGGCGCCGATGTGAATGCGCAGGATAAATTTGGCAA AACCGCGTTTGATATTAGCATTGATAACGGCAACGAA GATCTGGCGGAAATTCTGCAG |
| Linker | GS | GGCAGC |
| TEV | ENLYFQGS | GAAAACCTGTATTTTCAGGGATCC |
| Linker | GSGS | GGCAGCGGCAGC |
| GZB | MQPILLLLAFLLLPRADAGEII GGHEAKPHSRPYMAYLMIWD QKSLKRCGGFLIQDDFVLTAA HCWGSSINVTLGAHNIKEQEP TQQFIPVKRPIPHPAYNPKNFS NDIMLLQLERKAKRTRAVQP LRLPSNKAQVKPGQTCSVAG WGQTAPLGKHSHTLQEVKMT VQEDRKCESDLRHYYDSTIEL | ATGCAGCCGATCCTGCTCCTCCTGGCGTTCCTGCTGC TGCCACGTGCTGACGCTGGTGAAATCATCGGTGGTCA CGAAGCTAAACCGCACTCTCGTCCGTACATGGCTTAC CTGATGATCTGGGACCAGAAATCTCTGAAACGTTGCG GTGGTTTCCTGATCCAGGACGACTTCGTTCTGACCGC TGCTCACTGCTGGGGTTCTTCTATCAACGTTACCCTG GGTGCTCACAACATCAAAGAACAGGAACCGACCCAG CAGTTCATCCCGGTTAAACGTCCGATCCCGCACCCGG CTTACAACCCGAAAAACTTCTCTAACGACATCATGCT |

TABLE 1-continued

| N → C | Amino Acid Sequence | Nucleotide Sequence encoding the Amino Acid Sequence |
|---|---|---|
| | CVGDPEIKKTSFKGDSGGPLV CNKVAQGIVSYGRNNGMPPR ACTKVSSFVHWIKKTMKRH | GCTGCAGCTGGAACGTAAAGCTAAACGTACCCGTGC TGTTCAGCCGCTGCGTCTGCCGTCTAACAAAGCTCAG GTTAAACCGGGTCAGACCTGCTCTGTTGCTGGTTGGG GTCAGACCGCTCCGCTGGGTAAACACTCTCACACCCT GCAGGAAGTTAAAATGACCGTTCAGGAAGACCGTAA ATGCGAATCTGACCTGCGTCACTACTACGACTCTACC ATCGAACTGTGCGTTGGTGACCCGGAAATCAAAAAA ACCTCTTTCAAAGGTGACTCTGGTGGTCCGCTGGTTT GCAACAAAGTTGCTCAGGGTATCGTTTCTTACGGTCG TAACAACGGTATGCCGCCGCGTGCTTGCACCAAAGTT TCTTCTTTCGTTCACTGGATCAAAAAAACCATGAAAC GTCAC |
| Linker | GS | GGCAGC |
| MTS | AAVALLPAVLLALLAP | GCCGCGGTAGCGCTGCTCCCGGCGGTCCTGCTGGCCT TGCTGGCGCCC |
| BAA | KKKRK | AAAAAGAAGCGCAAG |
| linker | GS | GGCAGC |
| N9R | SGKIPRTLTA | AGCGGCAAAATTCCGCGTACCCTGACCGCG |
| linker | AS | GCTAGC |
| Dar(E) | DLGKKLLEAARAGQDDEVRI LMANGADVNADDTWGWTPL HLAAYQGHLEIVEVLLKNGA DVNAYDYIGWTPLHLAADGH LEIVEVLLKNGADVNASDYIG DTPLHLAAHNGHLEIVEVLLK HGADVNAQDKFGKTAFDISID NGNEDLAEILQ | GATCTGGGCAAAAAACTGCTGGAAGCGGCGCGCGCG GGCCAGGATGATGAAGTGCGCATTCTGATGGCGAAT GGTGCGGATGTTAACGCGGACGATACCTGGGGCTGG ACCCCACTGCATCTGGCCGCGTATCAGGGTCACCTGG AAATCGTGGAGGTGCTGCTGAAAAACGGCGCGGATG TGAACGCGTATGATTATATTGGCTGGACCCCGCTGCA TCTGGCGGCGGATGGCCATCTGGAAATTGTGGAAGT GCTGCTGAAAAACGGCGCTGATGTTAATGCTAGCGAT TATATTGGCGATACGCCGCTGCACCTGGCAGCGCATA ACGGCCATCTGGAGATTGTTGAAGTTCTGCTGAAGCA TGGCGCCGATGTGAATGCGCAGGATAAATTTGGCAA AACCGCGTTTGATATTAGCATTGATAACGGCAACGAA GATCTGGCGGAAATTCTGCAG |

(wherein, the part "His6-D(E)-TEV" at N-terminus was inserted merely for expression and identification, and has no effect on the activity of the fusion protein, and thus, the part was removed in the fusion protein used in the activity assay)

1.2. Preparation of GEGZB-MTS-BAA-M9R-Dar (EGFR)-MTS-BAA

A fusion protein (amino acid sequence: SEQ ID NO: 3; nucleotide sequence: SEQ ID NO: 4), which comprises, in order from N-terminus to C-terminus, "granzyme B fragment (GEGZB)-cell penetrating fusion peptide [MTS-BAA]-cleavage site (M9R)-targeting moiety [EGFR DAR-Pin (Dar(EGFR))]-cell penetrating fusion peptide [MTS-BAA]", was prepared (the second construct in FIG. 1). The amino acid sequence of KKKRK (SEQ ID NO: 15), which is a representative nuclear transfer signal, was used as "BAA".

The preparation of the fusion protein was performed referring to Example 1.1. The prepared fusion protein (SEQ ID NO: 3) and its coding nucleotide sequence (SEQ ID NO: 4) are summarized in Table 2:

TABLE 2

| N → C | Amino Acid Sequence | Nucleotide Sequence encoding the Amino Acid Sequence |
|---|---|---|
| His6 | MRGSHHHHHHDYDIPTT | ATGCGCGGCAGCCATCACCATCACCATCACGATTACG ATATCCCAACGACC |
| Dar (EGFR) | DLGKKLLEAARAGQDDEVRI LMANGADVNADDTWGWTPL HLAAYQGHLEIVEVLLKNGA DVNAYDYIGWTPLHLAADGH LEIVEVLLKNGADVNASDYIG DTPLHLAAHNGHLEIVEVLLK HGADVNAQDKFGKTAFDISID NGNEDLAEILQ | GATCTGGGCAAAAAACTGCTGGAAGCGGCGCGCGCG GGCCAGGATGATGAAGTGCGCATTCTGATGGCGAAT GGTGCGGATGTTAACGCGGACGATACCTGGGGCTGG ACCCCACTGCATCTGGCCGCGTATCAGGGTCACCTGG AAATCGTGGAGGTGCTGCTGAAAAACGGCGCGGATG TGAACGCGTATGATTATATTGGCTGGACCCCGCTGCA TCTGGCGGCGGATGGCCATCTGGAAATTGTGGAAGT GCTGCTGAAAAACGGCGCTGATGTTAATGCTAGCGAT TATATTGGCGATACGCCGCTGCACCTGGCAGCGCATA ACGGCCATCTGGAGATTGTTGAAGTTCTGCTGAAGCA TGGCGCCGATGTGAATGCGCAGGATAAATTTGGCAA AACCGCGTTTGATATTAGCATTGATAACGGCAACGAA GATCTGGCGGAAATTCTGCAG |

TABLE 2-continued

| N → C | Amino Acid Sequence | Nucleotide Sequence encoding the Amino Acid Sequence |
|---|---|---|
| linker | GS | GGCAGC |
| TEV-GEGZB | ENLYFQGEIIGGHEAKPHSRP YMAYLMIWDQKSLKRCGGFL IQDDFVLTAAHCWGSSINVTL GAHNIKEQEPTQQFIPVKRPIP HPAYNPKNFSNDIMLLQLERK AKRTRAVQPLRLPSNKAQVK PGQTCSVAGWGQTAPLGKHS HTLQEVKMTVQEDRKCESDL RHYYDSTIELCVGDPEIKKTSF KGDSGGPLVCNKVAQGIVSY GRNNGMPPRACTKVSSFVHW IKKTMKRH | GAAAACCTGTATTTTCAGGGAGAAATCATCGGTGGTC ACGAAGCTAAACCGCACTCTCGTCCGTACATGGCTTA CCTGATGATCTGGGACCAGAAATCTCTGAAACGTTGC GGTGGTTTCCTGATCCAGGACGACTTCGTTCTGACCG CTGCTCACTGCTGGGGTTCTTCTATCAACGTTACCCTG GGTGCTCACAACATCAAAGAACAGGAACCGACCCAG CAGTTCATCCCGGTTAAACGTCCGATCCCGCACCCGG CTTACAACCCGAAAAACTTCTCTAACGACATCATGCT GCTGCAGCTGGAACGTAAAGCTAAACGTACCCGTGC TGTTCAGCCGCTGCGTCTGCCGTCTAACAAAGCTCAG GTTAAACCGGGTCAGACCTGCTCTGTTGCTGGTTGGG GTCAGACCGCTCCGCTGGGTAAACACTCTCACACCCT GCAGGAAGTTAAAATGACCGTTCAGGAAGACCGTAA ATGCGAATCTGACCTGCGTCACTACTACGACTCTACC ATCGAACTGTGCGTTGGTGACCCGGAAATCAAAAAA ACCTCTTTCAAAGGTGACTCTGGTGGTCCGCTGGTTT GCAACAAAGTTGCTCAGGGTATCGTTTCTTACGGTCG TAACAACGGTATGCCGCCGCGTGCTTGCACCAAAGTT TCTTCTTTCGTTCACTGGATCAAAAAAACCATGAAAC GTCAC |
| linker | GS | GGCAGC |
| MTS | AAVALLPAVLLALLAP | GCCGCGGTAGCGCTGCTCCCGGCGGTCCTGCTGGCCT TGCTGGCGCCC |
| BAA | KKKRK | AAAAAGAAGCGCAAG |
| linker | GS | GGCAGC |
| M9R | SGKIPRTLTA | AGCGGCAAAATTCCGCGTACCCTGACCGCG |
| NheI | AS | GCTAGC |
| Dar (EGFR) | DLGKKLLEAARAGQDDEVRI LMANGADVNADDTWGWTPL HLAAYQGHLEIVEVLLKNGA DVNAYDYIGWTPLHLAADGH LEIVEVLLKNGADVNASDYIG DTPLHLAAHNGHLEIVEVLLK HGADVNAQDKFGKTAFDISID NGNEDLAEILQ | GATCTGGGCAAAAAACTGCTGGAAGCGGCGCGCGCG GGCCAGGATGATGAAGTGCGCATTCTGATGGCGAAT GGTGCGGATGTTAACGCGGACGATACCTGGGGCTGG ACCCCACTGCATCTGGCCGCGTATCAGGGTCACCTGG AAATCGTGGAGGTGCTGCTGAAAAACGGCGCGGATG TGAACGCGTATGATTATATTGGCTGGACCCCGCTGCA TCTGGCGGCGGATGGCCATCTGGAAATTGTGGAAGT GCTGCTGAAAAACGGCGCTGATGTTAATGCTAGCGAT TATATTGGCGATACGCCGCTGCACCTGGCAGCGCATA ACGGCCATCTGGAGATTGTTGAAGTTCTGCTGAAGCA TGGCGCCGATGTGAATGCGCAGGATAAATTTGGCAA AACCGCGTTTGATATTAGCATTGATAACGGCAACGAA GATCTGGCGGAAATTCTGCAG |
| linker | GS | GGCAGC |
| TAT | YGRKKRRQRRR | TATGGCCGCAAGAAACGTCGCCAGCGCCGTCGT |
| NLS | KKKRK | AAGAAAAAACGTAAG |

(wherein, the part "His6-D(E)-TEV" at N-terminus was inserted merely for expression and identification, and has no effect on the activity of the fusion protein, and thus, the part was removed in the fusion protein used in the activity assay)

1.3. Preparation of GEGZB-MTS-BAA-M9R-Dar (EGFR)

A fusion protein (amino acid sequence: SEQ ID NO: 5; nucleotide sequence: SEQ ID NO: 6), which comprises, in order from N-terminus to C-terminus, "granzyme B fragment (GEGZB)-cell penetrating fusion peptide [MTS-BAA]-cleavage site (M9R)-targeting moiety [EGFR DAR-Pin (Dar(EGFR))]", was prepared (the third construct in FIG. 1). The amino acid sequence of KKKRK (SEQ ID NO: 15), which is a representative nuclear transfer signal, was used as "BAA".

The preparation of the fusion protein was performed referring to Example 1.1. The prepared fusion protein (SEQ ID NO: 5) and its coding nucleotide sequence (SEQ ID NO: 6) are summarized in Table 3:

TABLE 3

| N → C | Amino Acid Sequence | Nucleotide Sequence encoding the Amino Acid Sequence |
|---|---|---|
| His6 | MRGSHHHHHHDYDIPTT | ATGCGCGGCAGCCATCACCATCACCATCACGATTACG<br>ATATCCCAACGACC |
| Dar<br>(EGFR) | DLGKKLLEAARAGQDDEVRI<br>LMANGADVNADDTWGWTPL<br>HLAAYQGHLEIVEVLLKNGA<br>DVNAYDYIGWTPLHLAADGH<br>LEIVEVLLKNGADVNASDYIG<br>DTPLHLAAHNGHLEIVEVLLK<br>HGADVNAQDKFGKTAFDISID<br>NGNEDLAEILQ | GATCTGGGCAAAAAACTGCTGGAAGCGGCGCGCGCG<br>GGCCAGGATGATGAAGTGCGCATTCTGATGGCGAAT<br>GGTGCGGATGTTAACGCGGACGATACCTGGGGCTGG<br>ACCCCACTGCATCTGGCCGCGTATCAGGGTCACCTGG<br>AAATCGTGGAGGTGCTGCTGAAAAACGGCGCGGATG<br>TGAACGCGTATGATTATATTGGCTGGACCCCGCTGCA<br>TCTGGCGGCGGATGGCCATCTGGAAATTGTGGAAGT<br>GCTGCTGAAAAACGGCGCTGATGTTAATGCTAGCGAT<br>TATATTGGCGATACGCCGCTGCACCTGGCAGCGCATA<br>ACGGCCATCTGGAGATTGTTGAAGTTCTGCTGAAGCA<br>TGGCGCCGATGTGAATGCGCAGGATAAATTTGGCAA<br>AACCGCGTTTGATATTAGCATTGATAACGGCAACGAA<br>GATCTGGCGGAAATTCTGCAG |
| linker | GS | GGCAGC |
| TEV-<br>GEGZB | ENLYFQGEIIGGHEAKPHSRP<br>YMAYLMIWDQKSLKRCGGFL<br>IQDDFVLTAAHCWGSSINVTL<br>GAHNIKEQEPTQQFIPVKRPIP<br>HPAYNPKNFSNDIMLLQLERK<br>AKRTRAVQPLRLPSNKAQVK<br>PGQTCSVAGWGQTAPLGKHS<br>HTLQEVKMTVQEDRKCESDL<br>RHYYDSTIELCVGDPEIKKTSF<br>KGDSGGPLVCNKVAQGIVSY<br>GRNNGMPPRACTKVSSFVHW<br>IKKTMKRH | GAAAACCTGTATTTTCAGGGAGAAATCATCGGTGGTC<br>ACGAAGCTAAACCGCACTCTCGTCCGTACATGGCTTA<br>CCTGATGATCTGGGACCAGAAATCTCTGAAACGTTGC<br>GGTGGTTTCCTGATCCAGGACGACTTCGTTCTGACCG<br>CTGCTCACTGCTGGGGTTCTTCTATCAACGTTACCCTG<br>GGTGCTCACAACATCAAAGAACAGGAACCGACCCAG<br>CAGTTCATCCCGGTTAAACGTCCGATCCCGCACCCGG<br>CTTACAACCCGAAAAACTTCTCTAACGACATCATGCT<br>GCTGCAGCTGGAACGTAAAGCTAAACGTACCCGTGC<br>TGTTCAGCCGCTGCGTCTGCCGTCTAACAAAGCTCAG<br>GTTAAACCGGGTCAGACCTGCTCTGTTGCTGGTTGGG<br>GTCAGACCGCTCCGCTGGGTAAACACTCTCACACCCT<br>GCAGGAAGTTAAAATGACCGTTCAGGAAGACCGTAA<br>ATGCGAATCTGACCTGCGTCACTACTACGACTCTACC<br>ATCGAACTGTGCGTTGGTGACCCGGAAATCAAAAAA<br>ACCTCTTTCAAAGGTGACTCTGGTGGTCCGCTGGTTT<br>GCAACAAAGTTGCTCAGGGTATCGTTTCTTACGGTCG<br>TAACAACGGTATGCCGCCGCGTGCTTGCACCAAAGTT<br>TCTTCTTTCGTTCACTGGATCAAAAAAACCATGAAAC<br>GTCAC |
| linker | GS | GGCAGC |
| MTS | AAVALLPAVLLALLAP | GCCGCGGTAGCGCTGCTCCCGGCGGTCCTGCTGGCCT<br>TGCTGGCGCCC |
| BAA | KKKRK | AAAAAGAAGCGCAAG |
| linker | GS | GGCAGC |
| N9R | SGKIPRTLTA | AGCGGCAAAATTCCGCGTACCCTGACCGCG |
| NheI | AS | GCTAGC |
| Dar<br>(EGFR) | DLGKKLLEAARAGQDDEVRI<br>LMANGADVNADDTWGWTPL<br>HLAAYQGHLEIVEVLLKNGA<br>DVNAYDYIGWTPLHLAADGH<br>LEIVEVLLKNGADVNASDYIG<br>DTPLHLAAHNGHLEIVEVLLK<br>HGADVNAQDKFGKTAFDISID<br>NGNEDLAEILQ | GATCTGGGCAAAAAACTGCTGGAAGCGGCGCGCGCG<br>GGCCAGGATGATGAAGTGCGCATTCTGATGGCGAAT<br>GGTGCGGATGTTAACGCGGACGATACCTGGGGCTGG<br>ACCCCACTGCATCTGGCCGCGTATCAGGGTCACCTGG<br>AAATCGTGGAGGTGCTGCTGAAAAACGGCGCGGATG<br>TGAACGCGTATGATTATATTGGCTGGACCCCGCTGCA<br>TCTGGCGGCGGATGGCCATCTGGAAATTGTGGAAGT<br>GCTGCTGAAAAACGGCGCTGATGTTAATGCTAGCGAT<br>TATATTGGCGATACGCCGCTGCACCTGGCAGCGCATA<br>ACGGCCATCTGGAGATTGTTGAAGTTCTGCTGAAGCA<br>TGGCGCCGATGTGAATGCGCAGGATAAATTTGGCAA<br>AACCGCGTTTGATATTAGCATTGATAACGGCAACGAA<br>GATCTGGCGGAAATTCTGCAG |

(wherein, the part "His6-D(E)-TEV" at N-terminus was inserted merely for expression and identification, and has no effect on the activity of the fusion protein, and thus, the part was removed in the fusion protein used in the activity assay)

1.4. Preparation of IEPDGZB-MTS-BAA-M9R-Dar (EGFR)-MTS-BAA

A fusion protein (amino acid sequence: SEQ ID NO: 7; nucleotide sequence: SEQ ID NO: 8), which comprises, in order from N-terminus to C-terminus, "granzyme B fragment (IEPDGZB)-cell penetrating fusion peptide [(MTS)-BAA]-cleavage site (M9R)-targeting moiety [EGFR DAR-Pin (Dar(EGFR))]-cell penetrating fusion peptide [MTS-BAA]", was prepared (the fourth construct in FIG. 1). The amino acid sequence of KKKRK (SEQ ID NO: 15), which is a representative nuclear transfer signal, was used as "BAA".

The preparation of the fusion protein was performed referring to Example 1.1. The prepared fusion protein (SEQ ID NO: 7) and its coding nucleotide sequence (SEQ ID NO: 8) are summarized in Table 4:

TABLE 4

| N → C | Amino Acid Sequence | Nucleotide Sequence encoding the Amino Acid Sequence |
|---|---|---|
| His6 | MRGSHHHHHHDYDIPTT | ATGCGCGGCAGCCATCACCATCACCATCACGATTACG ATATCCCAACGACC |
| Dar (EGFR) | DLGKKLLEAARAGQDDEVRI LMANGADVNADDTWGWTPL HLAAYQGHLEIVEVLLKNGA DVNAYDYIGWTPLHLAADGH LEIVEVLLKNGADVNASDYIG DTPLHLAAHNGHLEIVEVLLK HGADVNAQDKFGKTAFDISID NGNEDLAEILQ | GATCTGGGCAAAAAACTGCTGGAAGCGGCGCGCGCG GGCCAGGATGATGAAGTGCGCATTCTGATGGCGAAT GGTGCGGATGTTAACGCGGACGATACCTGGGGCTGG ACCCCACTGCATCTGGCCGCGTATCAGGGTCACCTGG AAATCGTGGAGGTGCTGCTGAAAAACGGCGCGGATG TGAACGCGTATGATTATATTGGCTGGACCCCGCTGCA TCTGGCGGCGGATGGCCATCTGGAAATTGTGGAAGT GCTGCTGAAAAACGGCGCTGATGTTAATGCTAGCGAT TATATTGGCGATACGCCGCTGCACCTGGCAGCGCATA ACGGCCATCTGGAGATTGTTGAAGTTCTGCTGAAGCA TGGCGCCGATGTGAATGCGCAGGATAAATTTGGCAA AACCGCGTTTGATATTAGCATTGATAACGGCAACGAA GATCTGGCGGAAATTCTGCAG |
| linker | GS | GGCAGC |
| TEV | ENLYFQGS | GAAAACCTGTATTTTCAGGGATCC |
| linker | GSGS | GGCAGCGGCAGC |
| IEPD-GZB | MGSIEPDIIGGHEAKPHSRPY MAYLMIWDQKSLKRCGGFLI QDDFVLTAAHCWGSSINVTL GAHNIKEQEPTQQFIPVKRPIP HPAYNPKNFSNDIMLLQLERK AKRTRAVQPLRLPSNKAQVK PGQTCSVAGWGQTAPLGKHS HTLQEVKMTVQEDRKCESDL RHYYDSTIELCVGDPEIKKTSF KGDSGGPLVCNKVAQGIVSY GRNNGMPPRACTKVSSFVHW IKKTMKRH | ATGGGCAGCATCGAACCAGATATCATCGGTGGTCAC GAAGCTAAACCGCACTCTCGTCCGTACATGGCTTACC TGATGATCTGGGACCAGAAATCTCTGAAACGTTGCG TGGTTTCCTGATCCAGGACGACTTCGTTCTGACCGCT GCTCACTGCTGCGGTGGGTTCTTCTATCAACGTTACCCTGG GTGCTCACAACATCAAAGAACAGGAACCGACCCAGC AGTTCATCCCGGTTAAACGTCCGATCCCGCACCCGGC TTACAACCCGAAAAACTTCTCTAACGACATCATGCTG CTGCAGCTGGAACGTAAAGCTAAACGTACCCGTGCT GTTCAGCCGCTGCGTCTGCCGTCTAACAAAGCTCAGG TTAAACCGGGTCAGACCTGCTCTGTTGCTGGTTGGGG TCAGACCGCTCCGCTGGGTAAACACTCTCACACCCTG CAGGAAGTTAAAATGACCGTTCAGGAAGACCGTAAA TGCGAATCTGACCTGCGTCACTACTACGACTCTACCA TCGAACTGTGCGTTGGTGACCCGGAAATCAAAAAAA CCTCTTTCAAAGGTGACTCTGGTGGTCCGCTGGTTTG CAACAAAGTTGCTCAGGGTATCGTTTCTTACGGTCGT AACAACGGTATGCCGCCGCGTGCTTGCACCAAGTTT CTTCTTTCGTTCACTGGATCAAAAAAACCATGAAACG TCAC |
| linker | GS | GGCAGC |
| MTS | AAVALLPAVLLALLAP | GCCGCGGTAGCGCTGCTCCCGGCGGTCCTGCTGGCCT TGCTGGCGCCC |
| BAA | KKKRK | AAAAAGAAGCGCAAG |
| linker | GS | GGCAGC |
| N9R | SGKIPRTLTA | AGCGGCAAAATTCCGCGTACCCTGACCGCG |
| NheI | AS | GCTAGC |
| Dar (EGFR) | DLGKKLLEAARAGQDDEVRI LMANGADVNADDTWGWTPL HLAAYQGHLEIVEVLLKNGA DVNAYDYIGWTPLHLAADGH LEIVEVLLKNGADVNASDYIG DTPLHLAAHNGHLEIVEVLLK HGADVNAQDKFGKTAFDISID NGNEDLAEILQ | GATCTGGGCAAAAAACTGCTGGAAGCGGCGCGCGCG GGCCAGGATGATGAAGTGCGCATTCTGATGGCGAAT GGTGCGGATGTTAACGCGGACGATACCTGGGGCTGG ACCCCACTGCATCTGGCCGCGTATCAGGGTCACCTGG AAATCGTGGAGGTGCTGCTGAAAAACGGCGCGGATG TGAACGCGTATGATTATATTGGCTGGACCCCGCTGCA TCTGGCGGCGGATGGCCATCTGGAAATTGTGGAAGT GCTGCTGAAAACGGCGCTGATGTTAATGCTAGCGAT TATATTGGCGATACGCCGCTGCACCTGGCAGCGCATA ACGGCCATCTGGAGATTGTTGAAGTTCTGCTGAAGCA TGGCGCCGATGTGAATGCGCAGGATAAATTTGGCAA AACCGCGTTTGATATTAGCATTGATAACGGCAACGAA GATCTGGCGGAAATTCTGCAG |

TABLE 4-continued

| N → C Amino Acid Sequence | | Nucleotide Sequence encoding the Amino Acid Sequence |
|---|---|---|
| linker | GS | GGCAGC |
| TAT | YGRKKRRQRRR | TATGGCCGCAAGAAACGTCGCCAGCGCCGTCGT |
| NLS | KKKRK | AAGAAAAAACGTAAG |

(wherein, the part "His6-D(E)-TEV" at N-terminus was inserted merely for expression and identification, and has no effect on the activity of the fusion protein, and thus, the part was removed in the fusion protein used in the activity assay; and the sequence "IEPD" included at the N-terminus of the granzyme B fragment (IEPD-GZB) is an auto-cleavage sequence which induces auto-activation of granzyme B and cleavage by granzyme B to be removed, making the sequence "IIG" to be exposed on the N-terminus of the granzyme B fragment (IEPD-GZB)

1.5. Preparation of IEPDGZB-MTS-BAA-M9R-Dar (EGFR)

A fusion protein (amino acid sequence: SEQ ID NO: 9; nucleotide sequence: SEQ ID NO: 10), which comprises, in order from N-terminus to C-terminus, "granzyme B fragment (IEPDGZB)-cell penetrating fusion peptide [MTS-BAA]-cleavage site (M9R)-targeting moiety [EGFR DAR-Pin (Dar(EGFR))]", was prepared (the fifth construct in FIG. 1). The amino acid sequence of KKKRK (SEQ ID NO: 15), which is a representative nuclear transfer signal, was used as "BAA".

The preparation of the fusion protein was performed referring to Example 1.1. The prepared fusion protein (SEQ ID NO: 9) and its coding nucleotide sequence (SEQ ID NO: 10) are summarized in Table 5:

TABLE 5

| N → C Amino Acid Sequence | | Nucleotide Sequence encoding the Amino Acid Sequence |
|---|---|---|
| His6 | MRGSHHHHHHDYDIPTT | ATGCGCGGCAGCCATCACCATCACCATCACGATTACG ATATCCCAACGACC |
| Dar (EGFR) | DLGKKLLEAARAGQDDEVRI LMANGADVNADDTWGWTPL HLAAYQGHLEIVEVLLKNGA DVNAYDYIGWTPLHLAADGH LEIVEVLLKNGADVNASDYIG DTPLHLAAHNGHLEIVEVLLK HGADVNAQDKFGKTAFDISID NGNEDLAEILQ | GATCTGGGCAAAAAACTGCTGGAAGCGGCGCGCGCG GGCCAGGATGATGAAGTGCGCATTCTGATGGCGAAT GGTGCGGATGTTAACGCGGACGATACCTGGGGCTGG ACCCCACTGCATCTGGCCGCGTATCAGGGTCACCTGG AAATCGTGGAGGTGCTGCTGAAAAACGGCGCGGATG TGAACGCGTATGATTATATTGGCTGGACCCCGCTGCA TCTGGCGGCGGATGGCCATCTGGAAATTGTGGAAGT GCTGCTGAAAAACGGCGCTGATGTTAATGCTAGCGAT TATATTGGCGATACGCCGCTGCACCTGGCAGCGCATA ACGGCCATCTGGAGATTGTTGAAGTTCTGCTGAAGCA TGGCGCCGATGTGAATGCGCAGGATAAATTTGGCAA AACCGCGTTTGATATTAGCATTGATAACGGCAACGAA GATCTGGCGGAAATTCTGCAG |
| linker | GS | GGCAGC |
| TEV | ENLYFQGS | GAAAACCTGTATTTTCAGGGATCC |
| linker | GSGS | GGCAGCGGCAGC |
| IEPD-GZB | MGS<u>IEPD</u>IIGGHEAKPHSRPY MAYLMIWDQKSLKRCGGFLI QDDFVLTAAHCWGSSINVTL GAHNIKEQEPTQQFIPVKRPIP HPAYNPKNFSNDIMLLQLERK AKRTRAVQPLRLPSNKAQVK PGQTCSVAGWGQTAPLGKHS HTLQEVKMTVQEDRKCESDL RHYYDSTIELCVGDPEIKKTSF KGDSGGPLVCNKVAQGIVSY GRNNGMPPRACTKVSSFVHW IKKTMKRH | ATGGGCAGCATCGAACCAGATATCATCGGTGGTCAC GAAGCTAAACCGCACTCTCGTCCGTACATGGCTTACC TGATGATCTGGGACCAGAAATCTCTGAAACGTTGCGG TGGTTTCCTGATCCAGGACGACTTCGTTCTGACCGCT GCTCACTGCTGGGGTTCTTCTATCAACGTTACCCTGG GTGCTCACAACATCAAAGAACAGGAACCGACCCAGC AGTTCATCCCGGTTAAACGTCCGATCCCGCACCCGGC TTACAACCCGAAAAACTTCTCTAACGACATCATGCTG CTGCAGCTGGAACGTAAAGCTAAACGTACCCGTGCT GTTCAGCCGCTGCGTCTGCCGTCTAACAAAGCTCAGG TTAAACCGGGTCAGACCTGCTCTGTTGCTGGTTGGGG TCAGACCGCTCCGCTGGGTAAACACTCTCACACCCTG CAGGAAGTTAAAATGACCGTTCAGGAAGACCGTAAA TGCGAATCTGACCTGCGTCACTACTACGACTCTACCA TCGAACTGTGCGTTGGTGACCCGGAAATCAAAAAAA CCTCTTTCAAAGGTGACTCTGGTGGTCCGCTGGTTTG CAACAAAGTTGCTCAGGGTATCGTTTCTTACGGTCGT AACAACGGTATGCCGCCGCGTGCTTGCACCAAAGTTT CTTCTTTCGTTCACTGGATCAAAAAAACCATGAAACG TCAC |

TABLE 5-continued

| N → C | Amino Acid Sequence | Nucleotide Sequence encoding the Amino Acid Sequence |
|---|---|---|
| linker | GS | GGCAGC |
| MTS | AAVALLPAVLLALLAP | GCCGCGGTAGCGCTGCTCCCGGCGGTCCTGCTGGCCT TGCTGGCGCCC |
| BAA | KKKRK | AAAAAGAAGCGCAAG |
| linker | GS | GGCAGC |
| N9R | SGKIPRTLTA | AGCGGCAAAATTCCGCGTACCCTGACCGCG |
| NheI | AS | GCTAGC |
| Dar (EGFR) | DLGKKLLEAARAGQDDEVRI LMANGADVNADDTWGWTPL HLAAYQGHLEIVEVLLKNGA DVNAYDYIGWTPLHLAADGH LEIVEVLLKNGADVNASDYIG DTPLHLAAHNGHLEIVEVLLK HGADVNAQDKFGKTAFDISID NGNEDLAEILQ | GATCTGGGCAAAAAACTGCTGGAAGCGGCGCGCGCG GGCCAGGATGATGAAGTGCGCATTCTGATGGCGAAT GGTGCGGATGTTAACGCGGACGATACCTGGGGCTGG ACCCCACTGCATCTGGCCGCGTATCAGGGTCACCTGG AAATCGTGGAGGTGCTGCTGAAAAACGGCGCGGATG TGAACGCGTATGATTATATTGGCTGGACCCCGCTGCA TCTGGCCGCGGATGGCCATCTGGAAATTGTGGAAGT GCTGCTGAAAAACGGCGCTGATGTTAATGCTAGCGAT TATATTGGCGATACGCCGCTGCACCTGGCAGCGCATA ACGGCCATCTGGAGATTGTTGAAGTTCTGCTGAAGCA TGGCGCCGATGTGAATGCGCAGGATAAATTTGGCAA AACCGCGTTTGATATTAGCATTGATAACGGCAACGAA GATCTGGCGGAAATTCTGCAG |

(wherein, the part "His6-D(E)-TEV" at N-terminus was inserted merely for expression and identification, and has no effect on the activity of the fusion protein, and thus, the part was removed in the fusion protein used in the activity assay; and the sequence "IEPD" included at the N-terminus of the granzyme B fragment (IEPD-GZB) is an auto-cleavage sequence which induces auto-activation of granzyme B and cleavage by granzyme B to be removed, making the sequence "IIG" to be exposed on the N-terminus of the granzyme B fragment (IEPD-GZB))

Example 2

Cancer Cell Proliferation Inhibition by Granzyme B Containing Fusion Protein

Anticancer effects of the prepared granzyme B containing fusion proteins were examined in human colon cancer cell line, HCT116 (ATCC) and RKO (ATCC).

Figure 3:
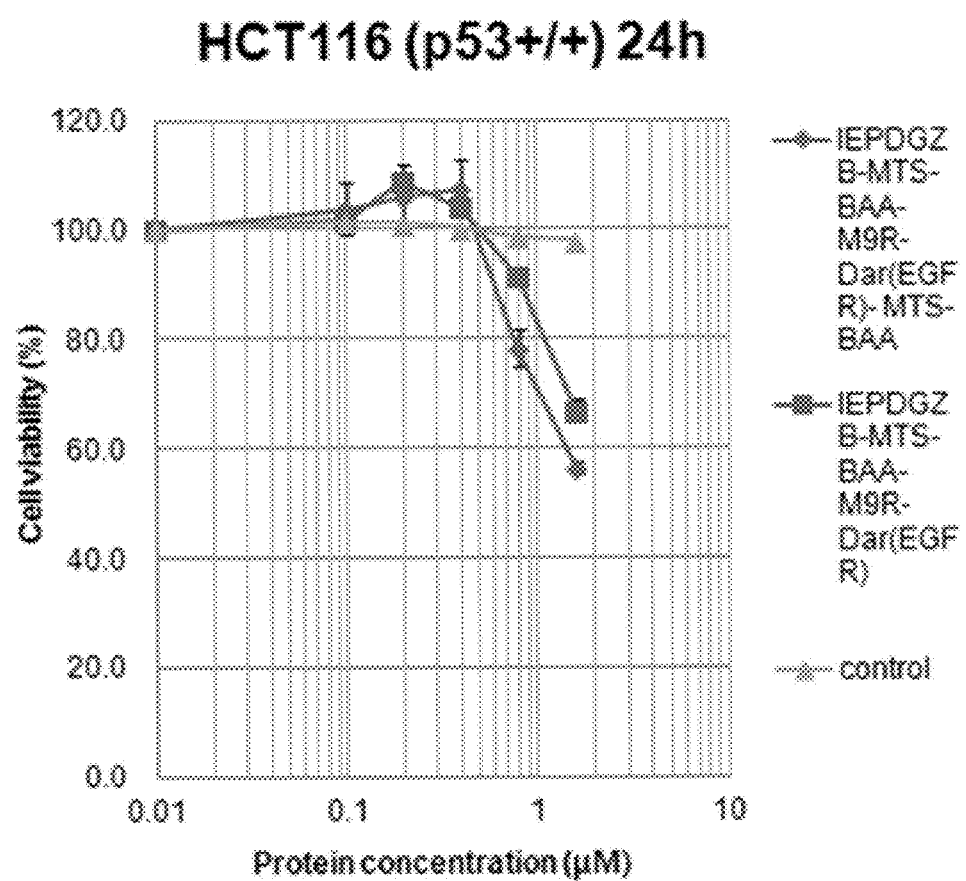
FIG. 3 is a graph showing cell viability of human colon cancer cell line HCT116 (ATCC) when treated with a fusion protein including granzyme B.
Figure 4:
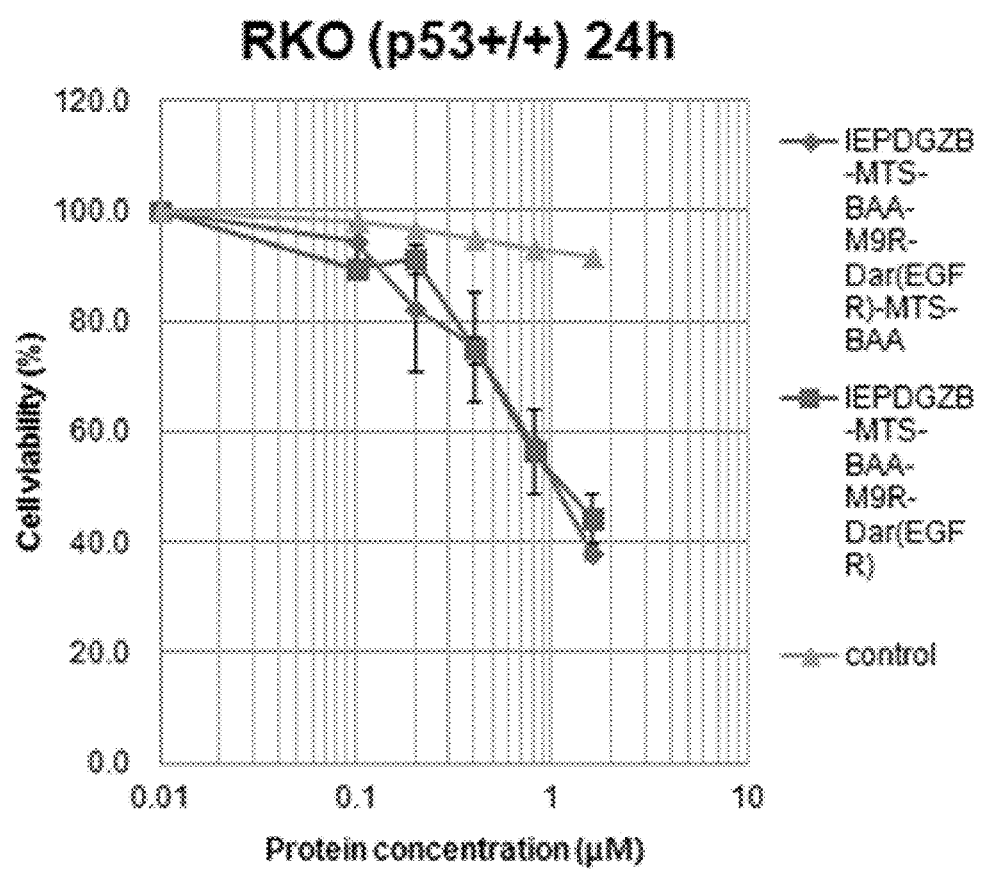
FIG. 4 is a graph showing cell viability of human colon cancer cell line RKO (ATCC) when treated with a fusion protein including granzyme B.

The cells were inoculated in RPMI medium (Gibco) supplemented with 10%(v/v) FBS in each 96-well plate in the amount of $1 \times 10^3$ cells per each well. In the next day, the cells were treated with each of granzyme B containing fusion proteins 'IEPDGZB-MTS-BAA-M9R-Dar(EGFR)-MTS-BAA' (SEQ ID NO: 7), and 'IEPDGZB-MTS-BAA-M9R-Dar(EGFR)' (SEQ ID NO: 9), wherein the concentration of each fusion protein was 0, 0.1, 0.2, 0.4, 0.8, or 1.6 µM, and the amount of each fusion protein treated was 100 µL per a well. The cells were incubated in $CO_2$ incubator for 24 hours under the condition of 37° C., and $CO_2$ 5%. After adding 80 µL of CellTiter-Glo reagent (Promega) to each well, luminescence was measured using EnVision Multilabel Reader (PerkinElmer), to obtain the cell viability (%). As a control protein, His6-Dar(EGFR)-linker-TEV was used, which was obtained from cleaved fusion proteins The obtained results are demonstrated in FIG. 3 (HCT116) and FIG. 4 (RKO). As shown in FIGS. 3 and 4, in both of HCT116 and RKO cell lines, the fusion proteins exhibit a decrease in cell viability by about 40~60% at the concentration of 1.6 µM. Such effect on cell viability of a cancer cell line is considerable, and at least about 10-fold superior to that of other tumor suppressor (e.g., p53 n-terminal peptide, p18 protein, etc.) when examined under the same conditions.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A fusion protein comprising (1) granzyme B; or a fragment of granzyme B comprising an active region of granzyme B and a dipeptidyl peptidase I (DPPI) cleavage sequence or an auto-cleavage sequence, (2) a cell penetrating peptide, (3) a targeting moiety, and (4) a peptidase or protease cleavage site between the cell penetrating peptide and the targeting moiety, wherein the cell penetrating peptide is a fusion peptide comprising (1) a hydrophobic peptide comprising SEQ ID NO: 12 or a peptide fragment comprising 7 to 16 contiguous amino acid residues of SEQ ID NO: 12; and (2) a basic peptide comprising a basic peptide unit, wherein the basic peptide unit comprises about 1 to about 6 basic amino acids or a repeat comprising about 2 to about 6 basic peptide units, wherein the basic amino acids are selected from the group consisting of lysine, arginine, and histidine;

or (1) a hydrophobic peptide comprising a total of about 5 to about 40 amino acids, wherein the hydrophobic peptide comprises about 70% or more hydrophobic amino acids based on the total number of amino acids in the hydrophobic peptide, and wherein the hydrophobic amino acids are selected from the group consisting of glycine, alanine, valine, leucine, isoleucine, methionine, proline, tryptophan, and phenylalanine; and (2) a basic peptide comprising KKKRK (SEQ ID NO: 15), KKKR(SEQ ID NO: 16), RKRK(SEQ ID NO: 17), RKRKRK(SEQ ID NO: 18), KKKKK(SEQ ID NO: 19), KKKKKR(SEQ ID NO: 20), KKKRKR (SEQ ID NO: 21), RRRRR(SEQ ID NO: 22), or RRRRRR(SEQ ID NO: 23).

2. The fusion protein of claim 1, wherein the cell penetrating peptide is a fusion peptide comprising (1) a hydrophobic peptide comprising SEQ ID NO: 12 or a peptide fragment comprising 7 to 16 contiguous amino acid residues of SEQ ID NO: 12; and (2) a basic peptide comprising KKKRK (SEQ ID NO: 15), KKKR(SEQ ID NO: 16), RKRK(SEQ ID NO: 17), RKRKRK(SEQ ID NO: 18), KKKKK(SEQ ID NO: 19), KKKKKR(SEQ ID NO: 20), KKKRKR(SEQ ID NO: 21), RRRRR(SEQ ID NO: 22), or RRRRRR(SEQ ID NO: 23).

3. The fusion protein of claim 1, wherein the cleavage sequence in the fragment of granzyme B comprises from about 2 to about 20 amino acids, comprising the contiguous amino acids GE or IEPD (SEQ ID NO: 36).

4. The fusion protein of claim 1, wherein the cleavage site of the peptidase or protease is a cleavage site recognized by matrix metalloproteinase, cathepsin, urokinase-type plasminogen activator, or a combination thereof.

5. The fusion protein of claim 1, wherein the targeting moiety comprises an antibody, an antigen-binding fragment of an antibody, a DARPin, an affibody, a lasso scaffold, a cyclotide, a knottin, an avimer, a Kunitz domain, an anticalin, an adnectin, a pronectin, a fynomer, a nanofitin, an affilin, or a combination thereof, wherein the targeting moiety targets:

a growth factor a receptor tyrosine kinase protein, or a combination thereof.

6. The fusion protein of claim 5, wherein the growth factor comprises epidermal growth factor (EGF), platelet-derived growth factor (PDGF), fibroblast growth factor (FGF), vascular endothelial growth factor (VEGF), or a combination thereof; and the receptor tyrosine kinase protein comprises an ErbB family member, insulin receptor, platelet-derived growth factor receptor (PDGFR), fibroblast growth factor receptor (FGFR), vascular endothelial growth factor receptor (VEGFR), hepatocyte growth factor receptor (HGFR), tropomyosin-receptor-kinase (Trk) receptor, Ephrin (Eph) receptor, AXL receptor, leukocyte receptor tyrosine kinase (LTK) receptor, TIE receptor, receptor tyrosine kinase-like orphan (ROR) receptor, discoidin domain receptor (DDR), RET receptor, KLG receptor, related to receptor tyrosine kinase (RYK) receptor, Muscle-Specific Kinase (MuSK) receptor, or a combination thereof.

7. The fusion protein of claim 1, wherein the fusion protein comprises in order from N-terminus to C-terminus (1) the granzyme B or a fragment thereof, (2) the cell penetrating peptide, (3) the cleavage site of a peptidase or protease, and (4) the targeting moiety.

8. The fusion protein of claim 1, wherein the fusion protein comprises SEQ ID NO: 1, 3, 5, 7, or 9.

9. A pharmaceutical composition comprising the fusion protein of claim 1 and a carrier.

10. A polynucleotide encoding a fusion protein of claim 1.

11. A method of preparing a fusion protein of claim 1 comprising expressing a polynucleotide encoding the fusion protein in a cell.

* * * * *

SEQUENCE LISTING

```
<160> NUMBER OF SEQ ID NOS: 68

<210> SEQ ID NO 1
<211> LENGTH: 621
<212> TYPE: PRT
<213> ORGANISM: Artificial Sequence
<220> FEATURE:
<223> OTHER INFORMATION: Synthetic Amino acid sequence of precursor of
      GZB-MTS-BAA-M9R-D(E)

<400> SEQUENCE: 1

Met Arg Gly Ser His His His His His His Asp Tyr Asp Ile Pro Thr
 1               5                  10                  15

Thr Asp Leu Gly Lys Lys Leu Leu Glu Ala Ala Arg Ala Gly Gln Asp
            20                  25                  30

Asp Glu Val Arg Ile Leu Met Ala Asn Gly Ala Asp Val Asn Ala Asp
        35                  40                  45

Asp Thr Trp Gly Trp Thr Pro Leu His Leu Ala Ala Tyr Gln Gly His
    50                  55                  60

Leu Glu Ile Val Glu Val Leu Leu Lys Asn Gly Ala Asp Val Asn Ala
65                  70                  75                  80

Tyr Asp Tyr Ile Gly Trp Thr Pro Leu His Leu Ala Ala Asp Gly His
                85                  90                  95

Leu Glu Ile Val Glu Val Leu Leu Lys Asn Gly Ala Asp Val Asn Ala
            100                 105                 110

Ser Asp Tyr Ile Gly Asp Thr Pro Leu His Leu Ala Ala His Asn Gly
        115                 120                 125

His Leu Glu Ile Val Glu Val Leu Leu Lys His Gly Ala Asp Val Asn
    130                 135                 140

Ala Gln Asp Lys Phe Gly Lys Thr Ala Phe Asp Ile Ser Ile Asp Asn
145                 150                 155                 160

Gly Asn Glu Asp Leu Ala Glu Ile Leu Gln Gly Ser Glu Asn Leu Tyr
                165                 170                 175

Phe Gln Gly Ser Gly Ser Gly Ser Met Gln Pro Ile Leu Leu Leu Leu
            180                 185                 190

Ala Phe Leu Leu Leu Pro Arg Ala Asp Ala Gly Glu Ile Ile Gly Gly
        195                 200                 205

His Glu Ala Lys Pro His Ser Arg Pro Tyr Met Ala Tyr Leu Met Ile
    210                 215                 220

Trp Asp Gln Lys Ser Leu Lys Arg Cys Gly Gly Phe Leu Ile Gln Asp
225                 230                 235                 240

Asp Phe Val Leu Thr Ala Ala His Cys Trp Gly Ser Ser Ile Asn Val
                245                 250                 255

Thr Leu Gly Ala His Asn Ile Lys Glu Gln Glu Pro Thr Gln Gln Phe
            260                 265                 270

Ile Pro Val Lys Arg Pro Ile Pro His Pro Ala Tyr Asn Pro Lys Asn
        275                 280                 285
```

Phe Ser Asn Asp Ile Met Leu Leu Gln Leu Glu Arg Lys Ala Lys Arg
    290                 295                 300

Thr Arg Ala Val Gln Pro Leu Arg Leu Pro Ser Asn Lys Ala Gln Val
305                 310                 315                 320

Lys Pro Gly Gln Thr Cys Ser Val Ala Gly Trp Gly Gln Thr Ala Pro
                325                 330                 335

Leu Gly Lys His Ser His Thr Leu Gln Glu Val Lys Met Thr Val Gln
                340                 345                 350

Glu Asp Arg Lys Cys Glu Ser Asp Leu Arg His Tyr Tyr Asp Ser Thr
            355                 360                 365

Ile Glu Leu Cys Val Gly Asp Pro Glu Ile Lys Lys Thr Ser Phe Lys
370                 375                 380

Gly Asp Ser Gly Gly Pro Leu Val Cys Asn Lys Val Ala Gln Gly Ile
385                 390                 395                 400

Val Ser Tyr Gly Arg Asn Asn Gly Met Pro Pro Arg Ala Cys Thr Lys
                405                 410                 415

Val Ser Ser Phe Val His Trp Ile Lys Lys Thr Met Lys Arg His Gly
                420                 425                 430

Ser Ala Ala Val Ala Leu Leu Pro Ala Val Leu Leu Ala Leu Leu Ala
            435                 440                 445

Pro Lys Lys Lys Arg Lys Gly Ser Ser Gly Lys Ile Pro Arg Thr Leu
450                 455                 460

Thr Ala Ala Ser Asp Leu Gly Lys Lys Leu Leu Glu Ala Ala Arg Ala
465                 470                 475                 480

Gly Gln Asp Asp Glu Val Arg Ile Leu Met Ala Asn Gly Ala Asp Val
                485                 490                 495

Asn Ala Asp Asp Thr Trp Gly Trp Thr Pro Leu His Leu Ala Ala Tyr
            500                 505                 510

Gln Gly His Leu Glu Ile Val Glu Val Leu Leu Lys Asn Gly Ala Asp
        515                 520                 525

Val Asn Ala Tyr Asp Tyr Ile Gly Trp Thr Pro Leu His Leu Ala Ala
    530                 535                 540

Asp Gly His Leu Glu Ile Val Glu Val Leu Leu Lys Asn Gly Ala Asp
545                 550                 555                 560

Val Asn Ala Ser Asp Tyr Ile Gly Asp Thr Pro Leu His Leu Ala Ala
                565                 570                 575

His Asn Gly His Leu Glu Ile Val Glu Val Leu Leu Lys His Gly Ala
            580                 585                 590

Asp Val Asn Ala Gln Asp Lys Phe Gly Lys Thr Ala Phe Asp Ile Ser
        595                 600                 605

Ile Asp Asn Gly Asn Glu Asp Leu Ala Glu Ile Leu Gln
    610                 615                 620

<210> SEQ ID NO 2
<211> LENGTH: 1866
<212> TYPE: DNA
<213> ORGANISM: Artificial Sequence
<220> FEATURE:
<223> OTHER INFORMATION: Synthetic Nucleotide sequence of precursor of
      GZB-MTS-BAA-M9R-D(E)

<400> SEQUENCE: 2
catatgcgcg gcagccatca ccatcaccat cacgattacg atatcccaac gaccgatctg      60
ggcaaaaaac tgctggaagc ggcgcgcgcg

-continued

```
gcgaatggtg cggatgttaa cgcggacgat acctggggct ggaccccact gcatctggcc    180
gcgtatcagg gtcacctgga atcgtggag gtgctgctga aaacggcgc ggatgtgaac     240
gcgtatgatt atattggctg accccgctg catctggcgg cggatggcca tctggaaatt     300
gtggaagtgc tgctgaaaaa cggcgctgat gttaatgcta gcgattatat ggcgatacg     360
ccgctgcacc tggcagcgca taacggccat ctggagattg ttgaagttct gctgaagcat    420
ggcgccgatg tgaatgcgca ggataaattt ggcaaaaccg cgtttgatat tagcattgat    480
aacggcaacg aagatctggc ggaaattctg cagggcagcg aaaaacctgta ttttcaggga    540
tccggcagcg gcagcatgca gccgatcctg ctcctcctgg cgttcctgct gctgccacgt    600
gctgacgctg gtgaaatcat cggtggtcac gaagctaaac cgcactctcg tccgtacatg    660
gcttacctga tgatctggga ccagaaatct ctgaaacgtt gcggtggttt cctgatccag    720
gacgacttcg ttctgaccgc tgctcactgc tgggggttctt ctatcaacgt taccctgggt    780
gctcacaaca tcaaagaaca ggaaccgacc cagcagttca tcccggttaa acgtccgatc    840
ccgcacccgg cttacaaccc gaaaaacttc tctaacgaca tcatgctgct gcagctggaa    900
cgtaaagcta acgtacccg tgctgttcag ccgctgcgtc tgccgtctaa caaagctcag    960
gttaaaccgg tcagacctg ctctgttgct ggttggggtc agaccgctcc gctgggtaaa   1020
cactctcaca ccctgcagga agttaaaatg accgttcagg aagaccgtaa atgcgaatct   1080
gacctgcgtc actactacga ctctaccatc gaactgtgcg ttggtgaccc ggaaatcaaa   1140
aaacctctt tcaaaggtga ctctggtggt ccgctggttt gcaacaaagt tgctcagggt   1200
atcgtttctt acggtcgtaa caacggtatg ccgccgcgtg cttgcaccaa agtttcttct   1260
ttcgttcact ggatcaaaaa aaccatgaaa cgtcacggca cgccgcggt agcgctgctc   1320
ccggcggtcc tgctggcctt gctggcgccc aaaaagaagc gcaagggcag cagcggcaaa   1380
attccgcgta ccctgaccgc ggctagcgat ctgggcaaaa aactgctgga agcggcgcgc   1440
gcgggccagg atgatgaagt gcgcattctg atggcgaatg gtgcggatgt taacgcggac   1500
gatacctggg gctggacccc actgcatctg gccgcgtatc agggtcacct ggaaatcgtg   1560
gaggtgctgc tgaaaaacgg cgcggatgtg aacgcgtatg attatattgg ctggaccccg   1620
ctgcatctgg cggcggatgg ccatctggaa attgtggaag tgctgctgaa aaacggcgct   1680
gatgttaatg ctagcgatta tattggcgat acgccgctgc acctggcagc gcataacggc   1740
catctggaga ttgttgaagt tctgctgaag catggcgccg atgtgaatgc gcaggataaa   1800
tttggcaaaa ccgcgtttga tattagcatt gataacggca acgaagatct ggcggaaatt   1860
ctgcag                                                                1866
```

<210> SEQ ID NO 3
<211> LENGTH: 615
<212> TYPE: PRT
<213> ORGANISM: Artificial Sequence
<220> FEATURE:
<223> OTHER INFORMATION: Synthetic Amino acid sequence of precursor of GEGZB-MTS-BAA-M9R-Dar(EGFR)-MTS-BAA

<400> SEQUENCE: 3

Met Arg Gly Ser His His His His His His Asp Tyr Asp Ile Pro Thr
1               5                   10                  15

Thr Asp Leu Gly Lys Lys Leu Leu Glu Ala Ala Arg Ala Gly Gln Asp
            20                  25                  30

Asp Glu Val Arg Ile Leu Met Ala Asn Gly Ala Asp Val Asn Ala Asp
        35                  40                  45

```
Asp Thr Trp Gly Trp Thr Pro Leu His Leu Ala Ala Tyr Gln Gly His
     50                  55                  60
Leu Glu Ile Val Glu Val Leu Leu Lys Asn Gly Ala Asp Val Asn Ala
 65                  70                  75                  80
Tyr Asp Tyr Ile Gly Trp Thr Pro Leu His Leu Ala Ala Asp Gly His
                 85                  90                  95
Leu Glu Ile Val Glu Val Leu Leu Lys Asn Gly Ala Asp Val Asn Ala
                100                 105                 110
Ser Asp Tyr Ile Gly Asp Thr Pro Leu His Leu Ala Ala His Asn Gly
            115                 120                 125
His Leu Glu Ile Val Glu Val Leu Leu Lys His Gly Ala Asp Val Asn
    130                 135                 140
Ala Gln Asp Lys Phe Gly Lys Thr Ala Phe Asp Ile Ser Ile Asp Asn
145                 150                 155                 160
Gly Asn Glu Asp Leu Ala Glu Ile Leu Gln Gly Ser Glu Asn Leu Tyr
                165                 170                 175
Phe Gln Gly Glu Ile Ile Gly Gly His Glu Ala Lys Pro His Ser Arg
            180                 185                 190
Pro Tyr Met Ala Tyr Leu Met Ile Trp Asp Gln Lys Ser Leu Lys Arg
        195                 200                 205
Cys Gly Gly Phe Leu Ile Gln Asp Asp Phe Val Leu Thr Ala Ala His
    210                 215                 220
Cys Trp Gly Ser Ser Ile Asn Val Thr Leu Gly Ala His Asn Ile Lys
225                 230                 235                 240
Glu Gln Glu Pro Thr Gln Gln Phe Ile Pro Val Lys Arg Pro Ile Pro
                245                 250                 255
His Pro Ala Tyr Asn Pro Lys Asn Phe Ser Asn Asp Ile Met Leu Leu
            260                 265                 270
Gln Leu Glu Arg Lys Ala Lys Arg Thr Arg Ala Val Gln Pro Leu Arg
        275                 280                 285
Leu Pro Ser Asn Lys Ala Gln Val Lys Pro Gly Gln Thr Cys Ser Val
    290                 295                 300
Ala Gly Trp Gly Gln Thr Ala Pro Leu Gly Lys His Ser His Thr Leu
305                 310                 315                 320
Gln Glu Val Lys Met Thr Val Gln Glu Asp Arg Lys Cys Glu Ser Asp
                325                 330                 335
Leu Arg His Tyr Tyr Asp Ser Thr Ile Glu Leu Cys Val Gly Asp Pro
            340                 345                 350
Glu Ile Lys Lys Thr Ser Phe Lys Gly Asp Ser Gly Gly Pro Leu Val
        355                 360                 365
Cys Asn Lys Val Ala Gln Gly Ile Val Ser Tyr Gly Arg Asn Asn Gly
    370                 375                 380
Met Pro Pro Arg Ala Cys Thr Lys Val Ser Ser Phe Val His Trp Ile
385                 390                 395                 400
Lys Lys Thr Met Lys Arg His Gly Ser Ala Ala Val Ala Leu Leu Pro
                405                 410                 415
Ala Val Leu Leu Ala Leu Leu Ala Pro Lys Lys Lys Arg Lys Gly Ser
            420                 425                 430
Ser Gly Lys Ile Pro Arg Thr Leu Thr Ala Ala Ser Asp Leu Gly Lys
        435                 440                 445
Lys Leu Leu Glu Ala Ala Arg Ala Gly Gln Asp Asp Glu Val Arg Ile
    450                 455                 460
```

```
Leu Met Ala Asn Gly Ala Asp Val Asn Ala Asp Asp Thr Trp Gly Trp
465                 470                 475                 480

Thr Pro Leu His Leu Ala Ala Tyr Gln Gly His Leu Glu Ile Val Glu
                485                 490                 495

Val Leu Leu Lys Asn Gly Ala Asp Val Asn Ala Tyr Asp Tyr Ile Gly
            500                 505                 510

Trp Thr Pro Leu His Leu Ala Ala Asp Gly His Leu Glu Ile Val Glu
        515                 520                 525

Val Leu Leu Lys Asn Gly Ala Asp Val Asn Ala Ser Asp Tyr Ile Gly
            530                 535                 540

Asp Thr Pro Leu His Leu Ala Ala His Asn Gly His Leu Glu Ile Val
545                 550                 555                 560

Glu Val Leu Leu Lys His Gly Ala Asp Val Asn Ala Gln Asp Lys Phe
                565                 570                 575

Gly Lys Thr Ala Phe Asp Ile Ser Ile Asp Asn Gly Asn Glu Asp Leu
            580                 585                 590

Ala Glu Ile Leu Gln Gly Ser Tyr Gly Arg Lys Arg Arg Gln Arg
        595                 600                 605

Arg Arg Lys Lys Lys Arg Lys
    610                 615
```

<210> SEQ ID NO 4
<211> LENGTH: 1848
<212> TYPE: DNA
<213> ORGANISM: Artificial Sequence
<220> FEATURE:
<223> OTHER INFORMATION: Synthetic Nucleotide sequence of precursor of
      GEGZB-MTS-BAA-M9R-Dar(EGFR)-MTS-BAA

<400> SEQUENCE: 4

```
catatgcgcg gcagccatca ccatcaccat cacgattacg atatcccaac gaccgatctg      60
ggcaaaaaac tgctggaagc ggcgcgcgcg ggccaggatg atgaagtgcg cattctgatg     120
gcgaatggtg cggatgttaa cgcggacgat acctggggct ggaccccact gcatctggcc     180
gcgtatcagg gtcacctgga atcgtggag gtgctgctga aaacggcgc ggatgtgaac      240 gcgtatgatt atattggctg gacccgctg catctggcgg cggatggcca tctggaaatt     300
gtggaagtgc tgctgaaaaa cggcgctgat gttaatgcta gcgattatat tggcgatacg     360
ccgctgcacc tggcagcgca taacggccat ctggagattg ttgaagttct gctgaagcat     420
ggcgccgatg tgaatgcgca ggataaattt ggcaaaaccg cgtttgatat tagcattgat     480
aacggcaacg aagatctggc ggaaattctg cagggcagcg aaaacctgta ttttcaggga     540
gaaatcatcg gtggtcacga agctaaaccg cactctcgtc cgtacatggc ttacctgatg     600
atctgggacc agaaatctct gaaacgttgc ggtggtttcc tgatccagga cgacttcgtt     660
ctgaccgctg ctcactgctg gggttcttct atcaacgtta ccctgggtgc tcacaacatc     720
aaagaacagg aaccgaccca gcagttcatc ccggttaaac gtccgatccc gcacccggct     780 tacaaccga aaaacttctc taacgacatc atgctgctgc agctggaacg taaagctaaa     840 cgtaccgtg ctgttcagcc gctgcgtctg ccgtctaaca agctcaggt taaaccgggt     900 cagacctgct ctgttgctgg ttggggtcag accgctccgc tgggtaaaca ctctcacacc     960
ctgcaggaag ttaaaatgac cgttcaggaa gaccgtaaat gcgaatctga cctgcgtcac    1020
tactacgact ctaccatcga actgtgcgtt ggtgacccgg aaatcaaaaa acctctcttc    1080
aaaggtgact ctggtggtcc gctggtttgc aacaaagttg ctcagggtat cgtttcttac    1140
```

```
ggtcgtaaca acggtatgcc gccgcgtgct tgcaccaaag tttcttcttt cgttcactgg    1200
atcaaaaaaa ccatgaaacg tcacggcagc gccgcggtag cgctgctccc ggcggtcctg    1260
ctggccttgc tggcgcccaa aaagaagcgc aagggcagca gcggcaaaat tccgcgtacc    1320
ctgaccgcgg ctagcgatct gggcaaaaaa ctgctggaag cggcgcgcgc gggccaggat    1380
gatgaagtgc gcattctgat ggcgaatggt gcggatgtta acgcggacga tacctggggc    1440
tggaccccac tgcatctggc cgcgtatcag ggtcacctgg aaatcgtgga ggtgctgctg    1500
aaaaacggcg cggatgtgaa cgcgtatgat tatattggct ggaccccgct gcatctggcg    1560
gcggatggcc atctggaaat tgtggaagtg ctgctgaaaa acggcgctga tgttaatgct    1620
agcgattata ttggcgatac gccgctgcac ctggcagcgc ataacggcca tctggagatt    1680
gttgaagttc tgctgaagca tggcgccgat gtgaatgcgc aggataaatt tggcaaaacc    1740
gcgtttgata ttagcattga taacggcaac gaagatctgg cggaaattct gcagggcagc    1800
tatggccgca agaaacgtcg ccagcgccgt cgtaagaaaa aacgtaag                 1848

<210> SEQ ID NO 5
<211> LENGTH: 597
<212> TYPE: PRT
<213> ORGANISM: Artificial Sequence
<220> FEATURE:
<223> OTHER INFORMATION: Synthetic Amino acid sequence of precursor of
      GEGZB-MTS-BAA-M9R-Dar(EGFR)

<400> SEQUENCE: 5

Met Arg Gly Ser His His His His His His Asp Tyr Asp Ile Pro Thr
 1               5                  10                  15

Thr Asp Leu Gly Lys Lys Leu Leu Glu Ala Ala Arg Ala Gly Gln Asp
            20                  25                  30

Asp Glu Val Arg Ile Leu Met Ala Asn Gly Ala Asp Val Asn Ala Asp
        35                  40                  45

Asp Thr Trp Gly Trp Thr Pro Leu His Leu Ala Ala Tyr Gln Gly His
    50                  55                  60

Leu Glu Ile Val Glu Val Leu Leu Lys Asn Gly Ala Asp Val Asn Ala
65                  70                  75                  80

Tyr Asp Tyr Ile Gly Trp Thr Pro Leu His Leu Ala Ala Asp Gly His
                85                  90                  95

Leu Glu Ile Val Glu Val Leu Leu Lys Asn Gly Ala Asp Val Asn Ala
            100                 105                 110

Ser Asp Tyr Ile Gly Asp Thr Pro Leu His Leu Ala Ala His Asn Gly
        115                 120                 125

His Leu Glu Ile Val Glu Val Leu Leu Lys His Gly Ala Asp Val Asn
    130                 135                 140

Ala Gln Asp Lys Phe Gly Lys Thr Ala Phe Asp Ile Ser Ile Asp Asn
145                 150                 155                 160

Gly Asn Glu Asp Leu Ala Glu Ile Leu Gln Gly Ser Glu Asn Leu Tyr
                165                 170                 175

Phe Gln Gly Glu Ile Ile Gly Gly His Glu Ala Lys Pro His Ser Arg
            180                 185                 190

Pro Tyr Met Ala Tyr Leu Met Ile Trp Asp Gln Lys Ser Leu Lys Arg
        195                 200                 205

Cys Gly Gly Phe Leu Ile Gln Asp Asp Phe Val Leu Thr Ala Ala His
    210                 215                 220

Cys Trp Gly Ser Ser Ile Asn Val Thr Leu Gly Ala His Asn Ile Lys
225                 230                 235                 240
```

```
Glu Gln Glu Pro Thr Gln Gln Phe Ile Pro Val Lys Arg Pro Ile Pro
            245                 250                 255

His Pro Ala Tyr Asn Pro Lys Asn Phe Ser Asn Asp Ile Met Leu Leu
        260                 265                 270

Gln Leu Glu Arg Lys Ala Lys Arg Thr Arg Ala Val Gln Pro Leu Arg
            275                 280                 285

Leu Pro Ser Asn Lys Ala Gln Val Lys Pro Gly Gln Thr Cys Ser Val
        290                 295                 300

Ala Gly Trp Gly Gln Thr Ala Pro Leu Gly Lys His Ser His Thr Leu
305                 310                 315                 320

Gln Glu Val Lys Met Thr Val Gln Glu Asp Arg Lys Cys Glu Ser Asp
                325                 330                 335

Leu Arg His Tyr Tyr Asp Ser Thr Ile Glu Leu Cys Val Gly Asp Pro
        340                 345                 350

Glu Ile Lys Lys Thr Ser Phe Lys Gly Asp Ser Gly Gly Pro Leu Val
            355                 360                 365

Cys Asn Lys Val Ala Gln Gly Ile Val Ser Tyr Gly Arg Asn Asn Gly
    370                 375                 380

Met Pro Pro Arg Ala Cys Thr Lys Val Ser Ser Phe Val His Trp Ile
385                 390                 395                 400

Lys Lys Thr Met Lys Arg His Gly Ser Ala Ala Val Ala Leu Leu Pro
                405                 410                 415

Ala Val Leu Leu Ala Leu Leu Ala Pro Lys Lys Arg Lys Gly Ser
        420                 425                 430

Ser Gly Lys Ile Pro Arg Thr Leu Thr Ala Ala Ser Asp Leu Gly Lys
            435                 440                 445

Lys Leu Leu Glu Ala Ala Arg Ala Gly Gln Asp Asp Glu Val Arg Ile
        450                 455                 460

Leu Met Ala Asn Gly Ala Asp Val Asn Ala Asp Asp Thr Trp Gly Trp
465                 470                 475                 480

Thr Pro Leu His Leu Ala Ala Tyr Gln Gly His Leu Glu Ile Val Glu
            485                 490                 495

Val Leu Leu Lys Asn Gly Ala Asp Val Asn Ala Tyr Asp Tyr Ile Gly
        500                 505                 510

Trp Thr Pro Leu His Leu Ala Ala Asp Gly His Leu Glu Ile Val Glu
        515                 520                 525

Val Leu Leu Lys Asn Gly Ala Asp Val Asn Ala Ser Asp Tyr Ile Gly
        530                 535                 540

Asp Thr Pro Leu His Leu Ala Ala His Asn Gly His Leu Glu Ile Val
545                 550                 555                 560

Glu Val Leu Leu Lys His Gly Ala Asp Val Asn Ala Gln Asp Lys Phe
                565                 570                 575

Gly Lys Thr Ala Phe Asp Ile Ser Ile Asp Asn Gly Asn Glu Asp Leu
            580                 585                 590

Ala Glu Ile Leu Gln
            595

<210> SEQ ID NO 6
<211> LENGTH: 1794
<212> TYPE: PRT
<213> ORGANISM: Artificial Sequence
<220> FEATURE:
<223> OTHER INFORMATION: Synthetic Nucleotide sequence of precursor of
      GEGZB-MTS-BAA-M9R-Dar(EGFR)
```

<400> SEQUENCE: 6

```
Cys Ala Thr Ala Thr Gly Cys Gly Cys Gly Gly Cys Ala Gly Cys Cys
  1               5                  10                  15

Ala Thr Cys Ala Cys Cys Ala Thr Cys Ala Cys Cys Ala Thr Cys Ala
             20                  25                  30

Cys Gly Ala Thr Thr Ala Cys Gly Ala Thr Ala Thr Cys Cys Cys Ala
         35                  40                  45

Ala Cys Gly Ala Cys Cys Gly Ala Thr Cys Thr Gly Gly Gly Cys Ala
     50                  55                  60

Ala Ala Ala Ala Ala Cys Thr Gly Cys Thr Gly Gly Ala Ala Gly Cys
 65                  70                  75                  80

Gly Gly Cys Gly Cys Gly Cys Gly Cys Gly Gly Gly Cys Cys Ala Gly
                 85                  90                  95

Gly Ala Thr Gly Ala Thr Gly Ala Ala Gly Thr Gly Cys Gly Cys Ala
            100                 105                 110

Thr Thr Cys Thr Gly Ala Thr Gly Gly Cys Gly Ala Ala Thr Gly Gly
        115                 120                 125

Thr Gly Cys Gly Gly Ala Thr Gly Thr Thr Ala Ala Cys Gly Cys Gly
    130                 135                 140

Gly Ala Cys Gly Ala Thr Ala Cys Cys Thr Gly Gly Gly Gly Cys Thr
145                 150                 155                 160

Gly Gly Ala Cys Cys Cys Cys Ala Cys Thr Gly Cys Ala Thr Cys Thr
                165                 170                 175

Gly Gly Cys Cys Gly Cys Gly Thr Ala Thr Cys Ala Gly Gly Gly Thr
            180                 185                 190

Cys Ala Cys Cys Thr Gly Gly Ala Ala Ala Thr Cys Gly Thr Gly Gly
        195                 200                 205

Ala Gly Gly Thr Gly Cys Thr Gly Cys Thr Gly Ala Ala Ala Ala Ala
    210                 215                 220

Cys Gly Gly Cys Gly Cys Gly Gly Ala Thr Gly Thr Gly Ala Ala Cys
225                 230                 235                 240

Gly Cys Gly Thr Ala Thr Gly Ala Thr Thr Ala Thr Ala Thr Thr Gly
                245                 250                 255

Gly Cys Thr Gly Gly Ala Cys Cys Cys Cys Gly Cys Thr Gly Cys Ala
            260                 265                 270

Thr Cys Thr Gly Gly Cys Gly Gly Cys Gly Gly Ala Thr Gly Gly Cys
        275                 280                 285

Cys Ala Thr Cys Thr Gly Gly Ala Ala Ala Thr Thr Gly Thr Gly Gly
    290                 295                 300

Ala Ala Gly Thr Gly Cys Thr Gly Cys Thr Gly Ala Ala Ala Ala Ala
305                 310                 315                 320

Cys Gly Gly Cys Gly Cys Thr Gly Ala Thr Gly Thr Thr Ala Ala Thr
                325                 330                 335

Gly Cys Thr Ala Gly Cys Gly Ala Thr Thr Ala Thr Ala Thr Thr Gly
            340                 345                 350

Gly Cys Gly Ala Thr Ala Cys Gly Cys Cys Gly Cys Thr Gly Cys Ala
        355                 360                 365

Cys Cys Thr Gly Gly Cys Ala Gly Cys Gly Cys Ala Thr Ala Ala Cys
    370                 375                 380

Gly Gly Cys Cys Ala Thr Cys Thr Gly Gly Ala Gly Ala Thr Thr Gly
385                 390                 395                 400

Thr Thr Gly Ala Ala Gly Thr Thr Cys Thr Gly Cys Thr Gly Ala Ala
                405                 410                 415
```

-continued

Gly Cys Ala Thr Gly Gly Cys Gly Cys Cys Gly Ala Thr Gly Thr Gly
420 425 430

Ala Ala Thr Gly Cys Gly Cys Ala Gly Gly Ala Thr Ala Ala Ala Thr
435 440 445

Thr Thr Gly Gly Cys Ala Ala Ala Ala Cys Cys Gly Cys Gly Thr Thr
450 455 460

Thr Gly Ala Thr Ala Thr Thr Ala Gly Cys Ala Thr Thr Gly Ala Thr
465 470 475 480

Ala Ala Cys Gly Gly Cys Ala Ala Cys Gly Ala Ala Gly Ala Thr Cys
485 490 495

Thr Gly Gly Cys Gly Gly Ala Ala Ala Thr Thr Cys Thr Gly Cys Ala
500 505 510

Gly Gly Gly Cys Ala Gly Cys Gly Ala Ala Ala Ala Cys Cys Thr Gly
515 520 525

Thr Ala Thr Thr Thr Thr Cys Ala Gly Gly Gly Ala Gly Ala Ala Ala
530 535 540

Thr Cys Ala Thr Cys Gly Gly Thr Gly Gly Thr Cys Ala Cys Gly Ala
545 550 555 560

Ala Gly Cys Thr Ala Ala Ala Cys Cys Gly Cys Ala Cys Thr Cys Thr
565 570 575

Cys Gly Thr Cys Cys Gly Thr Ala Cys Ala Thr Gly Gly Cys Thr Thr
580 585 590

Ala Cys Cys Thr Gly Ala Thr Gly Ala Thr Cys Thr Gly Gly Gly Ala
595 600 605

Cys Cys Ala Gly Ala Ala Ala Thr Cys Thr Cys Thr Gly Ala Ala Ala
610 615 620

Cys Gly Thr Thr Gly Cys Gly Gly Thr Gly Gly Thr Thr Thr Cys Cys
625 630 635 640

Thr Gly Ala Thr Cys Cys Ala Gly Gly Ala Cys Gly Ala Cys Thr Thr
645 650 655

Cys Gly Thr Thr Cys Thr Gly Ala Cys Cys Gly Cys Thr Gly Cys Thr
660 665 670

Cys Ala Cys Thr Gly Cys Thr Gly Gly Gly Gly Thr Thr Cys Thr Thr
675 680 685

Cys Thr Ala Thr Cys Ala Ala Cys Gly Thr Thr Ala Cys Cys Cys Thr
690 695 700

Gly Gly Gly Thr Gly Cys Thr Cys Ala Cys Ala Ala Cys Ala Thr Cys
705 710 715 720

Ala Ala Ala Gly Ala Ala Cys Ala Gly Gly Ala Ala Cys Cys Gly Ala
725 730 735

Cys Cys Cys Ala Gly Cys Ala Gly Thr Thr Cys Ala Thr Cys Cys Cys
740 745 750

Gly Gly Thr Thr Ala Ala Ala Cys Gly Thr Cys Cys Gly Ala Thr Cys
755 760 765

Cys Cys Gly Cys Ala Cys Cys Cys Gly Gly Cys Thr Thr Ala Cys Ala
770 775 780

Ala Cys Cys Cys Gly Ala Ala Ala Ala Ala Cys Thr Thr Cys Thr Cys
785 790 795 800

Thr Ala Ala Cys Gly Ala Cys Ala Thr Cys Ala Thr Gly Cys Thr Gly
805 810 815

Cys Thr Gly Cys Ala Gly Cys Thr Gly Gly Ala Ala Cys Gly Thr Ala
820 825 830

-continued

Ala Ala Gly Cys Thr Ala Ala Cys Gly Thr Ala Cys Cys Gly
        835                 840                 845

Thr Gly Cys Thr Gly Thr Thr Cys Ala Gly Cys Cys Gly Cys Thr Gly
    850                 855                 860

Cys Gly Thr Cys Thr Gly Cys Cys Gly Thr Cys Thr Ala Ala Cys Ala
865                 870                 875                 880

Ala Ala Gly Cys Thr Cys Ala Gly Gly Thr Thr Ala Ala Cys Cys
            885                 890                 895

Gly Gly Gly Thr Cys Ala Gly Ala Cys Cys Thr Gly Cys Thr Cys Thr
                900                 905                 910

Gly Thr Thr Gly Cys Thr Gly Gly Thr Gly Gly Gly Gly Thr Cys
    915                 920                 925

Ala Gly Ala Cys Cys Gly Cys Thr Cys Cys Gly Cys Thr Gly Gly Gly
    930                 935                 940

Thr Ala Ala Ala Cys Ala Cys Thr Cys Thr Ala Cys Ala Cys Cys
945                 950                 955                 960

Cys Thr Gly Cys Ala Gly Gly Ala Ala Gly Thr Thr Ala Ala Ala Ala
            965                 970                 975

Thr Gly Ala Cys Cys Gly Thr Thr Cys Ala Gly Gly Ala Ala Gly Ala
                980                 985                 990

Cys Cys Gly Thr Ala Ala Ala Thr Gly Cys Gly Ala Ala Thr Cys Thr
            995                 1000                1005

Gly Ala Cys Cys Thr Gly Cys Gly Thr Cys Ala Cys Thr Ala Cys Thr
    1010                1015                1020

Ala Cys Gly Ala Cys Thr Cys Thr Ala Cys Cys Ala Thr Cys Gly Ala
1025                1030                1035                1040

Ala Cys Thr Gly Thr Gly Cys Gly Thr Thr Gly Gly Thr Gly Ala Cys
            1045                1050                1055

Cys Cys Gly Gly Ala Ala Ala Thr Cys Ala Ala Ala Ala Ala Ala
        1060                1065                1070

Cys Cys Thr Cys Thr Thr Thr Cys Ala Ala Ala Gly Gly Thr Gly Ala
    1075                1080                1085

Cys Thr Cys Thr Gly Gly Thr Gly Gly Thr Cys Cys Gly Cys Thr Gly
    1090                1095                1100

Gly Thr Thr Thr Gly Cys Ala Ala Cys Ala Ala Ala Gly Thr Thr Gly
1105                1110                1115                1120

Cys Thr Cys Ala Gly Gly Gly Thr Ala Thr Cys Gly Thr Thr Thr Cys
            1125                1130                1135

Thr Thr Ala Cys Gly Gly Thr Cys Gly Thr Ala Ala Cys Ala Ala Cys
                1140                1145                1150

Gly Gly Thr Ala Thr Gly Cys Cys Gly Cys Cys Gly Cys Gly Thr Gly
        1155                1160                1165

Cys Thr Thr Gly Cys Ala Cys Cys Ala Ala Ala Gly Thr Thr Cys
    1170                1175                1180

Thr Thr Cys Thr Thr Thr Cys Gly Thr Thr Cys Ala Cys Thr Gly Gly
1185                1190                1195                1200

Ala Thr Cys Ala Ala Ala Ala Ala Ala Cys Cys Ala Thr Gly Ala
            1205                1210                1215

Ala Ala Cys Gly Thr Cys Ala Cys Gly Gly Cys Ala Gly Cys Gly Cys
                1220                1225                1230

Cys Gly Cys Gly Gly Thr Ala Gly Cys Gly Cys Thr Gly Cys Thr Cys
        1235                1240                1245

Cys Cys Gly Gly Cys Gly Gly Thr Cys Cys Thr Gly Cys Thr Gly Gly 1250 1255 1260

Cys Cys Thr Thr Gly Cys Thr Gly Gly Cys Gly Cys Cys Cys Ala Ala
1265 1270 1275 1280

Ala Ala Ala Gly Ala Ala Gly Cys Gly Cys Ala Ala Gly Gly Gly Cys
1285 1290 1295

Ala Gly Cys Ala Gly Cys Gly Gly Cys Ala Ala Ala Ala Thr Thr Cys
1300 1305 1310

Cys Gly Cys Gly Thr Ala Cys Cys Cys Thr Gly Ala Cys Cys Gly Cys
1315 1320 1325

Gly Gly Cys Thr Ala Gly Cys Gly Ala Thr Cys Thr Gly Gly Gly Cys
1330 1335 1340

Ala Ala Ala Ala Ala Ala Cys Thr Gly Cys Thr Gly Gly Ala Ala Gly
1345 1350 1355 1360

Cys Gly Gly Cys Gly Cys Gly Cys Gly Cys Gly Gly Gly Cys Cys Ala
1365 1370 1375

Gly Gly Ala Thr Gly Ala Thr Gly Ala Ala Gly Thr Gly Cys Gly Cys
1380 1385 1390

Ala Thr Thr Cys Thr Gly Ala Thr Gly Gly Cys Gly Ala Ala Thr Gly
1395 1400 1405

Gly Thr Gly Cys Gly Gly Ala Thr Gly Thr Thr Ala Ala Cys Gly Cys
1410 1415 1420

Gly Gly Ala Cys Gly Ala Thr Ala Cys Cys Thr Gly Gly Gly Gly Cys
1425 1430 1435 1440

Thr Gly Gly Ala Cys Cys Cys Cys Ala Cys Thr Gly Cys Ala Thr Cys
1445 1450 1455

Thr Gly Gly Cys Cys Gly Cys Gly Thr Ala Thr Cys Ala Gly Gly Gly
1460 1465 1470

Thr Cys Ala Cys Cys Thr Gly Gly Ala Ala Ala Thr Cys Gly Thr Gly
1475 1480 1485

Gly Ala Gly Gly Thr Gly Cys Thr Gly Cys Thr Gly Ala Ala Ala Ala
1490 1495 1500

Ala Cys Gly Gly Cys Gly Cys Gly Gly Ala Thr Gly Thr Gly Ala Ala
1505 1510 1515 1520

Cys Gly Cys Gly Thr Ala Thr Gly Ala Thr Thr Ala Thr Ala Thr Thr
1525 1530 1535

Gly Gly Cys Thr Gly Gly Ala Cys Cys Cys Gly Cys Thr Gly Cys
1540 1545 1550

Ala Thr Cys Thr Gly Gly Cys Gly Gly Cys Gly Gly Ala Thr Gly Gly
1555 1560 1565

Cys Cys Ala Thr Cys Thr Gly Gly Ala Ala Ala Thr Thr Gly Thr Gly
1570 1575 1580

Gly Ala Ala Gly Thr Gly Cys Thr Gly Cys Thr Gly Ala Ala Ala Ala
1585 1590 1595 1600

Ala Cys Gly Gly Cys Gly Cys Thr Gly Ala Thr Gly Thr Thr Ala Ala
1605 1610 1615

Thr Gly Cys Thr Ala Gly Cys Gly Ala Thr Thr Ala Thr Ala Thr Thr
1620 1625 1630

Gly Gly Cys Gly Ala Thr Ala Cys Gly Cys Cys Gly Cys Thr Gly Cys
1635 1640 1645

Ala Cys Cys Thr Gly Gly Cys Ala Gly Cys Gly Cys Ala Thr Ala Ala
1650 1655 1660

Cys Gly Gly Cys Cys Ala Thr Cys Thr Gly Gly Ala Gly Ala Thr Thr
1665 1670 1675 1680

```
Gly Thr Thr Gly Ala Ala Gly Thr Thr Cys Thr Gly Cys Thr Gly Ala
                1685                1690                1695

Ala Gly Cys Ala Thr Gly Gly Cys Gly Cys Cys Gly Ala Thr Gly Thr
            1700                1705                1710

Gly Ala Ala Thr Gly Cys Gly Cys Ala Gly Gly Ala Thr Ala Ala Ala
        1715                1720                1725

Thr Thr Thr Gly Gly Cys Ala Ala Ala Cys Cys Gly Cys Gly Thr
    1730                1735                1740

Thr Thr Gly Ala Thr Ala Thr Ala Gly Cys Ala Thr Thr Gly Ala
1745                1750                1755                1760

Thr Ala Ala Cys Gly Gly Cys Ala Ala Cys Gly Ala Ala Gly Ala Thr
            1765                1770                1775

Cys Thr Gly Gly Cys Gly Gly Ala Ala Ala Thr Thr Cys Thr Gly Cys
        1780                1785                1790

Ala Gly
```

<210> SEQ ID NO 7
<211> LENGTH: 626
<212> TYPE: PRT
<213> ORGANISM: Artificial Sequence
<220> FEATURE:
<223> OTHER INFORMATION: Synthetic Amino acid sequence of precursor of
      IEPDGZB-MTS-BAA-M9R-Dar(EGFR)-MTS-BAA

<400> SEQUENCE: 7

```
Met Arg Gly Ser His His His His His His Asp Tyr Asp Ile Pro Thr
 1               5                   10                  15

Thr Asp Leu Gly Lys Lys Leu Leu Glu Ala Ala Arg Ala Gly Gln Asp
            20                  25                  30

Asp Glu Val Arg Ile Leu Met Ala Asn Gly Ala Asp Val Asn Ala Asp
        35                  40                  45

Asp Thr Trp Gly Trp Thr Pro Leu His Leu Ala Ala Tyr Gln Gly His
    50                  55                  60

Leu Glu Ile Val Glu Val Leu Leu Lys Asn Gly Ala Asp Val Asn Ala
 65                  70                  75                  80

Tyr Asp Tyr Ile Gly Trp Thr Pro Leu His Leu Ala Ala Asp Gly His
                85                  90                  95

Leu Glu Ile Val Glu Val Leu Leu Lys Asn Gly Ala Asp Val Asn Ala
            100                 105                 110

Ser Asp Tyr Ile Gly Asp Thr Pro Leu His Leu Ala Ala His Asn Gly
        115                 120                 125

His Leu Glu Ile Val Glu Val Leu Leu Lys His Gly Ala Asp Val Asn
    130                 135                 140

Ala Gln Asp Lys Phe Gly Lys Thr Ala Phe Asp Ile Ser Ile Asp Asn
145                 150                 155                 160

Gly Asn Glu Asp Leu Ala Glu Ile Leu Gln Gly Ser Glu Asn Leu Tyr
                165                 170                 175

Phe Gln Gly Ser Gly Ser Gly Ser Met Gly Ser Ile Glu Pro Asp Ile
            180                 185                 190

Ile Gly Gly His Glu Ala Lys Pro His Ser Arg Pro Tyr Met Ala Tyr
        195                 200                 205

Leu Met Ile Trp Asp Gln Lys Ser Leu Lys Arg Cys Gly Gly Phe Leu
    210                 215                 220

Ile Gln Asp Asp Phe Val Leu Thr Ala Ala His Cys Trp Gly Ser Ser
225                 230                 235                 240
```

```
Ile Asn Val Thr Leu Gly Ala His Asn Ile Lys Glu Gln Glu Pro Thr
            245                 250                 255

Gln Gln Phe Ile Pro Val Lys Arg Pro Ile Pro His Pro Ala Tyr Asn
        260                 265                 270

Pro Lys Asn Phe Ser Asn Asp Ile Met Leu Gln Leu Glu Arg Lys
    275                 280                 285

Ala Lys Arg Thr Arg Ala Val Gln Pro Leu Arg Leu Pro Ser Asn Lys
290                 295                 300

Ala Gln Val Lys Pro Gly Gln Thr Cys Ser Val Ala Gly Trp Gly Gln
305                 310                 315                 320

Thr Ala Pro Leu Gly Lys His Ser His Thr Leu Gln Glu Val Lys Met
            325                 330                 335

Thr Val Gln Glu Asp Arg Lys Cys Glu Ser Asp Leu Arg His Tyr Tyr
            340                 345                 350

Asp Ser Thr Ile Glu Leu Cys Val Gly Asp Pro Glu Ile Lys Lys Thr
        355                 360                 365

Ser Phe Lys Gly Asp Ser Gly Gly Pro Leu Val Cys Asn Lys Val Ala
    370                 375                 380

Gln Gly Ile Val Ser Tyr Gly Arg Asn Asn Gly Met Pro Pro Arg Ala
385                 390                 395                 400

Cys Thr Lys Val Ser Ser Phe Val His Trp Ile Lys Lys Thr Met Lys
            405                 410                 415

Arg His Gly Ser Ala Ala Val Ala Leu Leu Pro Ala Val Leu Leu Ala
            420                 425                 430

Leu Leu Ala Pro Lys Lys Arg Lys Gly Ser Ser Gly Lys Ile Pro
        435                 440                 445

Arg Thr Leu Thr Ala Ala Ser Asp Leu Gly Lys Lys Leu Leu Glu Ala
    450                 455                 460

Ala Arg Ala Gly Gln Asp Asp Glu Val Arg Ile Leu Met Ala Asn Gly
465                 470                 475                 480

Ala Asp Val Asn Ala Asp Asp Thr Trp Gly Trp Thr Pro Leu His Leu
            485                 490                 495

Ala Ala Tyr Gln Gly His Leu Glu Ile Val Glu Val Leu Leu Lys Asn
        500                 505                 510

Gly Ala Asp Val Asn Ala Tyr Asp Tyr Ile Gly Trp Thr Pro Leu His
    515                 520                 525

Leu Ala Ala Asp Gly His Leu Glu Ile Val Glu Val Leu Leu Lys Asn
    530                 535                 540

Gly Ala Asp Val Asn Ala Ser Asp Tyr Ile Gly Asp Thr Pro Leu His
545                 550                 555                 560

Leu Ala Ala His Asn Gly His Leu Glu Ile Val Glu Val Leu Leu Lys
            565                 570                 575

His Gly Ala Asp Val Asn Ala Gln Asp Lys Phe Gly Lys Thr Ala Phe
            580                 585                 590

Asp Ile Ser Ile Asp Asn Gly Asn Glu Asp Leu Ala Glu Ile Leu Gln
        595                 600                 605

Gly Ser Tyr Gly Arg Lys Lys Arg Arg Gln Arg Arg Arg Lys Lys Lys
    610                 615                 620

Arg Lys
625

<210> SEQ ID NO 8
<211> LENGTH: 1881
```

<212> TYPE: DNA
<213> ORGANISM: Artificial Sequence
<220> FEATURE:
<223> OTHER INFORMATION: Synthetic Nucleotide sequence of precursor of
      IEPDGZB-MTS-BAA-M9R-Dar(EGFR)-MTS-BAA

<400> SEQUENCE: 8

```
catatgcgcg gcagccatca ccatcaccat cacgattacg atatcccaac gaccgatctg      60
ggcaaaaaac tgctggaagc ggcgcgcgcg ggccaggatg atgaagtgcg cattctgatg     120
gcgaatggtg cggatgttaa cgcggacgat acctggggct ggaccccact gcatctggcc     180
gcgtatcagg gtcacctgga atcgtggag gtgctgctga aaacggcgc ggatgtgaac      240
gcgtatgatt atattggctg gaccccgctg catctggcgg cggatggcca tctggaaatt     300
gtggaagtgc tgctgaaaaa cggcgctgat gttaatgcta gcgattatat ggcgatacg      360
ccgctgcacc tggcagcgca taacggccat ctggagattg ttgaagttct gctgaagcat     420
ggcgccgatg tgaatgcgca ggataaattt ggcaaaaccg cgtttgatat tagcattgat     480
aacggcaacg aagatctggc ggaaattctg cagggcagcg aaaacctgta ttttcaggga     540
tccggcagcg gcagcatggg cagcatcgaa ccagatatca tcggtggtca cgaagctaaa     600
ccgcactctc gtccgtacat ggcttacctg atgatctggg accagaaatc tctgaaacgt     660
tgcggtggtt tcctgatcca ggacgacttc gttctgaccg ctgctcactg ctggggttct     720
tctatcaacg ttaccctggg tgctcacaac atcaaagaac aggaaccgac ccagcagttc     780
atcccggtta acgtccgat cccgcacccg gcttacaacc gaaaaacttt ctctaacgac      840
atcatgctgc tgcagctgga acgtaaagct aaacgtaccc gtgctgttca gccgctgcgt     900
ctgccgtcta caaagctca ggttaaaccg ggtcagacct gctctgttgc tggttggggt      960
cagaccgctc cgctgggtaa acactctcac accctgcagg aagttaaaat gaccgttcag    1020
gaagaccgta atgcgaatc tgacctgcgt cactactacg actctaccat cgaactgtgc    1080
gttggtgacc cggaaatcaa aaaaacctct ttcaaaggtg actctggtgg tccgctggtt    1140
tgcaacaaag ttgctcaggg tatcgtttct tacggtcgta acaacggtat gccgccgcgt    1200
gcttgcacca aagtttcttc tttcgttcac tggatcaaaa aaaccatgaa acgtcacggc    1260
agcgccgcgg tagcgctgct cccggcggtc ctgctggcct tgctggcgcc caaaaagaag    1320
cgcaagggca gcagcggcaa aattccgcgt accctgaccg cggctagcga tctgggcaaa    1380
aaactgctgg aagcggcgcg cgcgggccag gatgatgaag tgcgcattct gatggcgaat    1440
ggtgcggatg ttaacgcgga cgataccggg gctggaccc cactgcatct ggccgcgtat    1500
cagggtcacc tggaaatcgt ggaggtgctg ctgaaaaacg gcgcggatgt gaacgcgtat    1560
gattatattg ctggaccccc gctgcatctg cggcggatg ccatctgga aattgtggaa      1620
gtgctgctga aaacggcgc tgatgttaat gctagcgatt atattggcga tacgccgctg    1680
cacctggcag cgcataacgg ccatctggag attgttgaag ttctgctgaa gcatggcgcc    1740
gatgtgaatg cgcaggataa atttggcaaa accgcgtttg atattagcat tgataacggc    1800
aacgaagatc tggcggaaat tctgcagggc agctatggcc gcaagaaacg tcgccagcgc    1860
cgtcgtaaga aaaaacgtaa g                                              1881
```

<210> SEQ ID NO 9
<211> LENGTH: 608
<212> TYPE: PRT
<213> ORGANISM: Artificial Sequence
<220> FEATURE:
<223> OTHER INFORMATION: Synthetic Amino acid sequence of precursor of IEPDGZB-MTS-BAA-M9R-Dar(EGFR)

<400> SEQUENCE: 9

| | | | | | | | | | | | | | | |
|---|---|---|---|---|---|---|---|---|---|---|---|---|---|---|
| Met | Arg | Gly | Ser | His | His | His | His | His | Asp | Tyr | Asp | Ile | Pro | Thr |
| 1 | | | | 5 | | | | | 10 | | | | | 15 |

Thr Asp Leu Gly Lys Lys Leu Leu Glu Ala Ala Arg Ala Gly Gln Asp
              20              25              30

Asp Glu Val Arg Ile Leu Met Ala Asn Gly Ala Asp Val Asn Ala Asp
    35              40              45

Asp Thr Trp Gly Trp Thr Pro Leu His Leu Ala Ala Tyr Gln Gly His
        50              55              60

Leu Glu Ile Val Glu Val Leu Leu Lys Asn Gly Ala Asp Val Asn Ala
65            70              75              80

Tyr Asp Tyr Ile Gly Trp Thr Pro Leu His Leu Ala Ala Asp Gly His
            85              90              95

Leu Glu Ile Val Glu Val Leu Leu Lys Asn Gly Ala Asp Val Asn Ala
              100            105            110

Ser Asp Tyr Ile Gly Asp Thr Pro Leu His Leu Ala Ala His Asn Gly
            115            120            125

His Leu Glu Ile Val Glu Val Leu Leu Lys His Gly Ala Asp Val Asn
    130              135            140

Ala Gln Asp Lys Phe Gly Lys Thr Ala Phe Asp Ile Ser Ile Asp Asn
145              150            155            160

Gly Asn Glu Asp Leu Ala Glu Ile Leu Gln Gly Ser Glu Asn Leu Tyr
            165            170            175

Phe Gln Gly Ser Gly Ser Gly Ser Met Gly Ser Ile Glu Pro Asp Ile
        180              185              190

Ile Gly Gly His Glu Ala Lys Pro His Ser Arg Pro Tyr Met Ala Tyr
        195              200            205

Leu Met Ile Trp Asp Gln Lys Ser Leu Lys Arg Cys Gly Gly Phe Leu
    210              215            220

Ile Gln Asp Asp Phe Val Leu Thr Ala Ala His Cys Trp Gly Ser Ser
225              230            235            240

Ile Asn Val Thr Leu Gly Ala His Asn Ile Lys Glu Gln Glu Pro Thr
            245            250            255

Gln Gln Phe Ile Pro Val Lys Arg Pro Ile Pro His Pro Ala Tyr Asn
        260              265            270

Pro Lys Asn Phe Ser Asn Asp Ile Met Leu Leu Gln Leu Glu Arg Lys
        275              280            285

Ala Lys Arg Thr Arg Ala Val Gln Pro Leu Arg Leu Pro Ser Asn Lys
    290              295            300

Ala Gln Val Lys Pro Gly Gln Thr Cys Ser Val Ala Gly Trp Gly Gln
305              310            315            320

Thr Ala Pro Leu Gly Lys His Ser His Thr Leu Gln Glu Val Lys Met
            325            330            335

Thr Val Gln Glu Asp Arg Lys Cys Glu Ser Asp Leu Arg His Tyr Tyr
            340            345            350

Asp Ser Thr Ile Glu Leu Cys Val Gly Asp Pro Glu Ile Lys Lys Thr
        355              360            365

Ser Phe Lys Gly Asp Ser Gly Gly Pro Leu Val Cys Asn Lys Val Ala
    370              375            380

Gln Gly Ile Val Ser Tyr Gly Arg Asn Asn Gly Met Pro Pro Arg Ala
385              390            395            400

```
Cys Thr Lys Val Ser Ser Phe Val His Trp Ile Lys Thr Met Lys
                405                 410                 415

Arg His Gly Ser Ala Ala Val Ala Leu Leu Pro Ala Val Leu Leu Ala
            420                 425                 430

Leu Leu Ala Pro Lys Lys Lys Arg Lys Gly Ser Ser Gly Lys Ile Pro
        435                 440                 445

Arg Thr Leu Thr Ala Ala Ser Asp Leu Gly Lys Lys Leu Leu Glu Ala
    450                 455                 460

Ala Arg Ala Gly Gln Asp Asp Glu Val Arg Ile Leu Met Ala Asn Gly
465                 470                 475                 480

Ala Asp Val Asn Ala Asp Thr Trp Gly Trp Thr Pro Leu His Leu
                485                 490                 495

Ala Ala Tyr Gln Gly His Leu Glu Ile Val Glu Val Leu Leu Lys Asn
                500                 505                 510

Gly Ala Asp Val Asn Ala Tyr Asp Tyr Ile Gly Trp Thr Pro Leu His
            515                 520                 525

Leu Ala Ala Asp Gly His Leu Glu Ile Val Glu Val Leu Leu Lys Asn
        530                 535                 540

Gly Ala Asp Val Asn Ala Ser Asp Tyr Ile Gly Asp Thr Pro Leu His
545                 550                 555                 560

Leu Ala Ala His Asn Gly His Leu Glu Ile Val Glu Val Leu Leu Lys
                565                 570                 575

His Gly Ala Asp Val Asn Ala Gln Asp Lys Phe Gly Lys Thr Ala Phe
                580                 585                 590

Asp Ile Ser Ile Asp Asn Gly Asn Glu Asp Leu Ala Glu Ile Leu Gln
            595                 600                 605

<210> SEQ ID NO 10
<211> LENGTH: 1827
<212> TYPE: DNA
<213> ORGANISM: Artificial Sequence
<220> FEATURE:
<223> OTHER INFORMATION: Synthetic Nucleotide sequence of precursor of
      IEPDGZB-MTS-BAA-M9R-Dar(EGFR)

<400> SEQUENCE: 10
catatgcgcg gcagccatca ccatcaccat cacgattacg atatcccaac gaccgatctg     60
ggcaaaaaac tgctggaagc ggcgcgcgcg ggccaggatg atgaagtgcg cattctgatg    120
gcgaatggtg cggatgttaa cgcggacgat acctggggct ggaccccact gcatctggcc    180
gcgtatcagg gtcacctgga atcgtggag gtgctgctga aaacggcgc ggatgtgaac     240 gcgtatgatt atattggctg gaccccgctg catctggcgg cggatggcca tctggaaatt    300
gtggaagtgc tgctgaaaaa cggcgctgat gttaatgcta gcgattatat tggcgatacg    360
ccgctgcacc tggcagcgca taacggccat ctggagattg ttgaagttct gctgaagcat    420
ggcgccgatg tgaatgcgca ggataaattt ggcaaaaccg cgtttgatat tagcattgat    480
aacggcaacg aagatctggc ggaaattctg caggcagcg aaaacctgta ttttcaggga    540
tccggcagcg gcagcatggg cagcatcgaa ccagatatca tcggtggtca cgaagctaaa    600
ccgcactctc gtccgtacat ggcttacctg atgatctggg accagaaatc tctgaaacgt    660
tgcggtggtt tcctgatcca ggacgacttc gttctgaccg ctgctcactg ctgggggttct    720 tctatcaacg ttacctgggg tgctcacaac atcaaagaac aggaaccgac ccagcagttc    780
atcccggtta acgtccgat cccgcacccg gcttacaacc cgaaaaactt ctctaacgac    840
atcatgctgc tgcagctgga acgtaaagct aaacgtaccc gtgctgttca gccgctgcgt    900
```

```
ctgccgtcta acaaagctca ggttaaaccg ggtcagacct gctctgttgc tggttggggt    960
cagaccgctc cgctgggtaa acactctcac accctgcagg aagttaaaat gaccgttcag   1020
gaagaccgta atgcgaatc tgacctgcgt cactactacg actctaccat cgaactgtgc    1080
gttggtgacc cggaaatcaa aaaacctct ttcaaaggtg actctggtgg tccgctggtt    1140
tgcaacaaag ttgctcaggg tatcgtttct tacggtcgta acaacggtat gccgccgcgt   1200
gcttgcacca aagtttcttc tttcgttcac tggatcaaaa aaaccatgaa acgtcacggc   1260
agcgccgcgg tagcgctgct cccggcggtc ctgctggcct tgctggcgcc aaaaagaag    1320 cgcaagggca gcagcggcaa aattccgcgt accctgaccg cggctagcga tctgggcaaa   1380
aaactgctgg aagcggcgcg cgcgggccag gatgatgaag tgcgcattct gatggcgaat   1440
ggtgcggatg ttaacgcgga cgatacctgg ggctggaccc cactgcatct ggccgcgtat   1500
cagggtcacc tggaaatcgt ggaggtgctg ctgaaaaacg gcgcggatgt gaacgcgtat   1560
gattatattg ctggaccccc gctgcatctg cggcggatg gccatctgga aattgtggaa    1620
gtgctgctga aaaacggcgc tgatgttaat gctagcgatt atattggcga tacgccgctg   1680
cacctggcag cgcataacgg ccatctggag attgttgaag ttctgctgaa gcatggcgcc   1740
gatgtgaatg cgcaggataa atttggcaaa accgcgtttg atattagcat tgataacggc   1800
aacgaagatc tggcggaaat tctgcag                                      1827

<210> SEQ ID NO 11
<211> LENGTH: 227
<212> TYPE: PRT
<213> ORGANISM: Artificial Sequence
<220> FEATURE:
<223> OTHER INFORMATION: Synthetic Active region of granzyme B

<400

Ala Gln Gly Ile Val Ser Tyr Gly Arg Asn Asn Gly Met Pro Pro Arg
            195                 200                 205

Ala Cys Thr Lys Val Ser Ser Phe Val His Trp Ile Lys Lys Thr Met
    210                 215                 220

Lys Arg His
225

<210> SEQ ID NO 12
<211> LENGTH: 16
<212> TYPE: PRT
<213> ORGANISM: Artificial Sequence
<220> FEATURE:
<223> OTHER INFORMATION: Synthetic membrane-translocation sequence (MTS)

<400> SEQUENCE: 12

Ala Ala Val Ala Leu Leu Pro Ala Val Leu Leu Ala Leu Leu Ala Pro
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Synthetic Fragment of MTS

<400> SEQUENCE: 13

Ala Ala Val Ala Leu Leu Pro
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Fragment of MTS

<400> SEQUENCE: 14

Ala Val Leu Leu Ala Leu Leu Ala Pro
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Unit of basic peptide

<400> SEQUENCE: 15

Lys Lys Lys Arg Lys
1               5

<210> SEQ ID NO 16
<211> LENGTH: 4
<212> TYPE: PRT
<213> ORGANISM: Artificial Sequence
<220> FEATURE:
<223> OTHER INFORMATION: Synthetic Unit of basic peptide

<400> SEQUENCE: 16

Lys Lys Lys Arg
1

<210> SEQ ID NO 17
<211> LENGTH: 4
<212> TYPE: PRT
<213> ORGANISM: Artificial Sequence

```
<220> FEATURE:
<223> OTHER INFORMATION: Synthetic Unit of basic peptide

<400> SEQUENCE: 17

Arg Lys Arg Lys
  1

<210> SEQ ID NO 18
<211> LENGTH: 6
<212> TYPE: PRT
<213> ORGANISM: Artificial Sequence
<220> FEATURE:
<223> OTHER INFORMATION: Synthetic Unit of basic peptide

<400> SEQUENCE: 18

Arg Lys Arg Lys Arg Lys
  1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Unit of basic peptide

<400> SEQUENCE: 19

Lys Lys Lys Lys Lys
  1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Unit of basic peptide

<400> SEQUENCE: 20

Lys Lys Lys Lys Lys Arg
  1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Unit of basic peptide

<400> SEQUENCE: 21

Lys Lys Lys Arg Lys Arg
  1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Unit of basic peptide

<400> SEQUENCE: 22

Arg Arg Arg Arg Arg
  1               5

<210> SEQ ID NO 23
<211> LENGTH: 6
<212> TYPE: PRT
<213> ORGANISM: Artificial Sequence
<220> FEATURE:
```

```
<223> OTHER INFORMATION: Synthetic Unit of basic peptide

<400> SEQUENCE: 23

Arg Arg Arg Arg Arg Arg
 1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic TAT peptide

<400> SEQUENCE: 24

Tyr Gly Arg Lys Lys Arg Arg Gln Arg Arg Arg
 1               5                   10

<210> SEQ ID NO 25
<211> LENGTH: 9
<212> TYPE: PRT
<213> ORGANISM: Artificial Sequence
<220> FEATURE:
<223> OTHER INFORMATION: Synthetic TAT peptide

<400> SEQUENCE: 25

Arg Lys Lys Arg Arg Gln Arg Arg Arg
 1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic  MTD103

<400> SEQUENCE: 26

Leu Ala Leu Pro Val Leu Leu Leu Ala
 1               5

<210> SEQ ID NO 27
<211> LENGTH: 21
<212> TYPE: PRT
<213> ORGANISM: Artificial Sequence
<220> FEATURE:
<223> OTHER INFORMATION: Synthetic TP10

<400> SEQUENCE: 27

Ala Gly Tyr Leu Leu Gly Lys Ile Asn Leu Lys Ala Leu Ala Ala Leu
 1               5                   10                  15

Ala Lys Lys Ile Leu
            20

<210> SEQ ID NO 28
<211> LENGTH: 16
<212> TYPE: PRT
<213> ORGANISM: Artificial Sequence
<220> FEATURE:
<223> OTHER INFORMATION: Synthetic Penetratin

<400> SEQUENCE: 28

Arg Gln Ile Lys Ile Trp Phe Gln Asn Arg Arg Met Lys Trp Lys Lys
 1               5                   10                  15

<210> SEQ ID NO 29
<211> LENGTH: 18
<212> TYPE: PRT
```

-continued

```
<213> ORGANISM: Artificial Sequence
<220> FEATURE:
<223> OTHER INFORMATION: Synthetic MAP(model amphipathic peptide)

<400> SEQUENCE: 29

Lys Leu Ala Leu Lys Leu Ala Leu Lys Ala Leu Lys Ala Ala Leu Lys
 1               5                  10                  15

Leu Ala

<210> SEQ ID NO 30
<211> LENGTH: 153
<212> TYPE: PRT
<213> ORGANISM: Artificial Sequence
<220> FEATURE:
<223> OTHER INFORMATION: Synthetic Anti-EGFR DARPin

<400> SEQUENCE: 30

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Asp Asp
                20                  25                  30

Thr Trp Gly Trp Thr Pro Leu His Leu Ala Ala Tyr Gln Gly His Leu
            35                  40                  45

Glu Ile Val Glu Val Leu Leu Lys Asn Gly Ala Asp Val Asn Ala Tyr
        50                  55                  60

Asp Tyr Ile Gly Trp Thr Pro Leu His Leu Ala Ala Asp Gly His Leu
 65                  70                  75                  80

Glu Ile Val Glu Val Leu Leu Lys Asn Gly Ala Asp Val Asn Ala Ser
                85                  90                  95

Asp Tyr Ile Gly Asp Thr Pro Leu His Leu Ala Ala His Asn Gly His
                100                 105                 110

Leu Glu Ile Val Glu Val Leu Leu Lys His Gly Ala Asp Val Asn Ala
            115                 120                 125

Gln Asp Lys Phe Gly Lys Thr Ala Phe Asp Ile Ser Ile Asp Asn Gly
        130                 135                 140

Asn Glu Asp Leu Ala Glu Ile Leu Gln
145                 150

<210> SEQ ID NO 31
<211> LENGTH: 154
<212> TYPE: PRT
<213> ORGANISM: Artificial Sequence
<220> FEATURE:
<223> OTHER INFORMATION: Synthetic Anti-EGFR DARPin

<400> SEQUENCE: 31

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Thr Asp
                20                  25                  30

Asn Asp Gly Asn Thr Pro Leu His Leu Ser Ala Trp Ile Gly His Leu
            35                  40                  45

Glu Ile Val Glu Val Leu Leu Lys His Gly Ala Asp Val Asn Ala Asp
        50                  55                  60

Asp Leu Leu Gly Met Thr Pro Leu His Leu Ala Ala Asp Thr Gly His
 65                  70                  75                  80

Leu Glu Ile Val Glu Val Leu Leu Lys Tyr Gly Ala Asp Val Asn Ala
                85                  90                  95
```

-continued

```
Arg Asp Thr Arg Gly Lys Thr Pro Leu His Leu Ala Ala Arg Asp Gly
            100                 105                 110

His Leu Glu Ile Val Glu Val Leu Lys His Asp Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 32
<211> LENGTH: 154
<212> TYPE: PRT
<213> ORGANISM: Artificial Sequence
<220> FEATURE:
<223> OTHER INFORMATION: Synthetic Anti-EGFR DARPin

<400> SEQUENCE: 32

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Phe Asp
            20                  25                  30

Tyr Trp Gly Met Thr Pro Leu His Leu Ala Ala Asp Asn Gly His Leu
        35                  40                  45

Glu Ile Val Glu Val Leu Leu Lys His Gly Ala Asp Val Asn Ala Ser
    50                  55                  60

Asp Asn Phe Gly Phe Thr Pro Leu His Leu Ala Ala Phe Tyr Gly His
65                  70                  75                  80

Leu Glu Ile Val Glu Val Leu Leu Lys His Gly Ala Asp Val Asn Ala
                85                  90                  95

Phe Asp Met Trp Gly Asn Thr Pro Leu His Leu Ala Ala Gln Asn Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 33
<211> LENGTH: 187
<212> TYPE: PRT
<213> ORGANISM: Artificial Sequence
<220> FEATURE:
<223> OTHER INFORMATION: Synthetic Anti-EGFR DARPin

<400> SEQUENCE: 33

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asp Asp
            20                  25                  30

Asn Ala Gly Arg Thr Pro Leu His Leu Ala Ala Asn Phe Gly His Leu
        35                  40                  45

Glu Ile Val Glu Val Leu Leu Lys Asn Gly Ala Asp Val Asn Ala Lys
    50                  55                  60

Gly His His Cys Asn Thr Pro Leu His Leu Ala Ala Trp Ala Gly His
65                  70                  75                  80

Leu Glu Ile Val Glu Val Leu Leu Lys Tyr Gly Ala Asp Val Asn Ala
                85                  90                  95
```

Asp Asp Asp Glu Gly Tyr Thr Pro Leu His Leu Ala Ala Asp Ile Gly
            100                 105                 110

Asp Leu Glu Ile Val Glu Val Leu Lys Tyr Gly Ala Asp Val Asn
        115                 120                 125

Ala Trp Asp Met Tyr Gly Arg Thr Pro Leu His Leu Ala Ala Ser Ala
130                 135                 140

Gly His Leu Glu Ile Val Glu Val Leu Lys Tyr Gly Ala Asp Val
145                 150                 155                 160

Asn Ala Gln Asp Lys Phe Gly Lys Thr Ala Phe Asp Ile Ser Ile Asp
                165                 170                 175

Asn Gly Asn Glu Asp Leu Ala Glu Ile Leu Gln
        180                 185

<210> SEQ ID NO 34
<211> LENGTH: 8
<212> TYPE: PRT
<213> ORGANISM: Artificial Sequence
<220> FEATURE:
<223> OTHER INFORMATION: Synthetic TEV

<400> SEQUENCE: 34

Glu Asn Leu Tyr Phe Gln Gly Ser
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic MMP9 cleavage site

<400> SEQUENCE: 35

Ser Gly Lys Ile Pro Arg Thr Leu Thr Ala
1               5                   10

<210> SEQ ID NO 36
<211> LENGTH: 4
<212> TYPE: PRT
<213> ORGANISM: Artificial Sequence
<220> FEATURE:
<223> OTHER INFORMATION: Synthetic cleavage site of granzyme B

<400> SEQUENCE: 36

Ile Glu Pro Asp
1

<210> SEQ ID NO 37
<211> LENGTH: 153
<212> TYPE: PRT
<213> ORGANISM: Artificial Sequence
<220> FEATURE:
<223> OTHER INFORMATION: Synthetic DARPin E_01

<400> SEQUENCE: 37

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asp Asp
            20                  25                  30

Thr Trp Gly Trp Thr Pro Leu His Leu Ala Ala Tyr Gln Gly His Leu
        35                  40                  45

Glu Ile Val Glu Val Leu Leu Lys Asn Gly Ala Asp Val Asn Ala Tyr
    50                  55                  60

```
Asp Tyr Ile Gly Trp Thr Pro Leu His Leu Ala Ala Asp Gly His Leu
 65                  70                  75                  80

Glu Ile Val Glu Val Leu Leu Lys Asn Gly Ala Asp Val Asn Ala Ser
                 85                  90                  95

Asp Tyr Ile Gly Asp Thr Pro Leu His Leu Ala Ala His Asn Gly His
            100                 105                 110

Leu Glu Ile Val Glu Val Leu Leu Lys His Gly Ala Asp Val Asn Ala
        115                 120                 125

Gln Asp Lys Phe Gly Lys Thr Ala Phe Asp Ile Ser Ile Asp Asn Gly
    130                 135                 140

Asn Glu Asp Leu Ala Glu Ile Leu Gln
145                 150

<210> SEQ ID NO 38
<211> LENGTH: 154
<212> TYPE: PRT
<213> ORGANISM: Artificial Sequence
<220> FEATURE:
<223> OTHER INFORMATION: Synthetic DARPin E_67

<400> SEQUENCE: 38

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Thr Asp
             20                  25                  30

Asn Asp Gly Asn Thr Pro Leu His Leu Ser Ala Trp Ile Gly His Leu
        35                  40                  45

Glu Ile Val Glu Val Leu Leu Lys His Gly Ala Asp Val Asn Ala Asp
    50                  55                  60

Asp Leu Leu Gly Met Thr Pro Leu His Leu Ala Ala Asp Thr Gly His
 65                  70                  75                  80

Leu Glu Ile Val Glu Val Leu Leu Lys Tyr Gly Ala Asp Val Asn Ala
                 85                  90                  95

Arg Asp Thr Arg Gly Lys Thr Pro Leu His Leu Ala Ala Arg Asp Gly
            100                 105                 110

His Leu Glu Ile Val Glu Val Leu Leu Lys His Asp Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 39
<211> LENGTH: 154
<212> TYPE: PRT
<213> ORGANISM: Artificial Sequence
<220> FEATURE:
<223> OTHER INFORMATION: Synthetic DARPin E_68

<400> SEQUENCE: 39

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Phe Asp
             20                  25                  30

Tyr Trp Gly Met Thr Pro Leu His Leu Ala Ala Asp Asn Gly His Leu
        35                  40                  45

Glu Ile Val Glu Val Leu Leu Lys His Gly Ala Asp Val Asn Ala Ser
```

```
                    50                  55                  60
Asp Asn Phe Gly Phe Thr Pro Leu His Leu Ala Ala Phe Tyr Gly His
 65                  70                  75                  80

Leu Glu Ile Val Glu Val Leu Lys His Gly Ala Asp Val Asn Ala
                 85                  90                  95

Phe Asp Met Trp Gly Asn Thr Pro Leu His Leu Ala Ala Gln Asn Gly
                100                 105                 110

His Leu Glu Ile Val Glu Val Leu Leu Lys Asn Gly Ala Asp Val Asn
                115                 120                 125

Ala Gln Asp Lys Phe Gly Lys Thr Ala Phe Asp Ile Ser Ile Asp Asn
                130                 135                 140

Gly Asn Glu Asp Leu Ala Glu Ile Leu Gln
145                 150

<210> SEQ ID NO 40
<211> LENGTH: 187
<212> TYPE: PRT
<213> ORGANISM: Artificial Sequence
<220> FEATURE:
<223> OTHER INFORMATION: Synthetic DARPin E_69

<400> SEQUENCE: 40

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Asp Asp
                 20                  25                  30

Asn Ala Gly Arg Thr Pro Leu His Leu Ala Ala Asn Phe Gly His Leu
                 35                  40                  45

Glu Ile Val Glu Val Leu Leu Lys Asn Gly Ala Asp Val Asn Ala Lys
                 50                  55                  60

Gly His His Cys Asn Thr Pro Leu His Leu Ala Ala Trp Ala Gly His
 65                  70                  75                  80

Leu Glu Ile Val Glu Val Leu Leu Lys Tyr Gly Ala Asp Val Asn Ala
                 85                  90                  95

Asp Asp Asp Glu Gly Tyr Thr Pro Leu His Leu Ala Ala Asp Ile Gly
                100                 105                 110

Asp Leu Glu Ile Val Glu Val Leu Leu Lys Tyr Gly Ala Asp Val Asn
                115                 120                 125

Ala Trp Asp Met Tyr Gly Arg Thr Pro Leu His Leu Ala Ala Ser Ala
                130                 135                 140

Gly His Leu Glu Ile Val Glu Val Leu Leu Lys Tyr Gly Ala Asp Val
145                 150                 155                 160

Asn Ala Gln Asp Lys Phe Gly Lys Thr Ala Phe Asp Ile Ser Ile Asp
                165                 170                 175

Asn Gly Asn Glu Asp Leu Ala Glu Ile Leu Gln
                180                 185

<210> SEQ ID NO 41
<211> LENGTH: 154
<212> TYPE: PRT
<213> ORGANISM: Artificial Sequence
<220> FEATURE:
<223> OTHER INFORMATION: Synthetic DARPin 9_16

<400> SEQUENCE: 41

Asp Leu Gly Lys Lys Leu Leu Glu Ala Ala Arg Ala Gly Gln Asp Asp
  1               5                  10                  15
```

-continued

```
Glu Val Arg Ile Leu Met Ala Asn Gly Ala Asp Val Asn Ala His Asp
            20                  25                  30

Phe His Gly Leu Thr Pro Leu His Leu Ala Ala Gly Met Gly His Leu
        35                  40                  45

Glu Ile Val Glu Val Leu Leu Lys Asn Gly Ala Asp Val Asn Ala Val
    50                  55                  60

Asp Thr Asp Gly Ile Thr Leu Leu His Leu Ala Ala Tyr Tyr Gly His
65                  70                  75                  80

Leu Glu Ile Val Glu Val Leu Leu Lys His Gly Ala Asp Val Asn Ala
                85                  90                  95

His Asp Tyr Ala Gly Ser Thr Pro Leu His Leu Ala Ala Asn Thr Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 42
<211> LENGTH: 154
<212> TYPE: PRT
<213> ORGANISM: Artificial Sequence
<220> FEATURE:
<223> OTHER INFORMATION: Synthetic DARPin 9_26

<400> SEQUENCE: 42

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Lys Asp
            20                  25                  30

Phe Tyr Gly Ile Thr Pro Leu His Leu Ala Ala Tyr Gly His Leu
        35                  40                  45

Glu Ile Val Glu Val Leu Leu Lys His Gly Ala Asp Val Asn Ala His
    50                  55                  60

Asp Trp Asn Gly Trp Thr Pro Leu His Leu Ala Ala Lys Tyr Gly His
65                  70                  75                  80

Leu Glu Ile Val Glu Val Leu Leu Lys His Gly Ala Asp Val Asn Ala
                85                  90                  95

Ile Asp Asn Ala Gly Lys Thr Pro Leu His Leu Ala Ala His Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 43
<211> LENGTH: 154
<212> TYPE: PRT
<213> ORGANISM: Artificial Sequence
<220> FEATURE:
<223> OTHER INFORMATION: Synthetic DARPin 9_29
<220> FEATURE:
<221> NAME/KEY: MOD_RES
<222> LOCATION: (67)
<223> OTHER INFORMATION: Xaa is Ala, Ile, Leu, Met, Phe, Pro, Trp, Val,
      Asn, Cys, Gln, Gly, Ser, Thr, Tyr, Asp, Glu, Arg, His or Lys
```

<400> SEQUENCE: 43

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala His Asp
            20                  25                  30

Phe Tyr Gly Ile Thr Pro Leu His Leu Ala Ala Asn Phe Gly His Leu
        35                  40                  45

Glu Ile Val Glu Val Leu Leu Lys His Gly Ala Asp Val Asn Ala Phe
    50                  55                  60

Asp Tyr Xaa Asp Asn Thr Pro Leu His Leu Ala Asp Ala Gly His
65                  70                  75                  80

Leu Glu Ile Val Glu Val Leu Leu Lys Tyr Gly Ala Asp Val Asn Ala
                85                  90                  95

Ser Asp Arg Asp Gly His Thr Pro Leu His Leu Ala Ala Arg Glu Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 44
<211> LENGTH: 154
<212> TYPE: PRT
<213> ORGANISM: Artificial Sequence
<220> FEATURE:
<223> OTHER INFORMATION: Synthetic DARPin H_14

<400> SEQUENCE: 44

Asp Leu Gly Lys Lys Leu Leu Glu Ala Ala Arg Ala Gly Gln Asp Asp
1               5                   10                  15

Glu Val Cys Ile Leu Met Ala Asn Gly Ala Asp Val Asn Ala Thr Asp
            20                  25                  30

Ile His Gly His Thr Pro Leu His Leu Ala Ala Ala Met Gly His Leu
        35                  40                  45

Glu Ile Val Glu Val Leu Leu Lys Asn Gly Ala Asp Val Asn Ala Asn
    50                  55                  60

Asp Trp Arg Gly Phe Thr Pro Leu His Leu Ala Ala Leu Asn Gly His
65                  70                  75                  80

Leu Glu Ile Val Glu Val Leu Leu Lys Asn Gly Ala Asp Val Asn Ala
                85                  90                  95

Thr Asp Thr Ala Gly Asn Thr Pro Leu His Leu Ala Ala Trp Phe Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 45
<211> LENGTH: 187
<212> TYPE: PRT
<213> ORGANISM: Artificial Sequence
<220> FEATURE:

<223> OTHER INFORMATION: Synthetic DARPin B4_01

<400> SEQUENCE: 45

```
Asp Leu Gly Lys Lys Leu Leu Glu Ala Ala Arg Ala Gly Gln Asp Asp
1               5                   10                  15

Glu Val His Ile Leu Met Ala Asn Gly Ala Asp Val Asn Ala Val Asp
            20                  25                  30

Trp Met Gly Asp Thr Pro Leu His Leu Ala Ala Phe Tyr Gly His Leu
        35                  40                  45

Glu Ile Val Glu Val Leu Leu Lys Asn Gly Ala Asp Val Asn Ala Lys
    50                  55                  60

Asp Thr Trp Gly Asp Thr Pro Leu His Leu Ala Ala Leu Leu Gly Arg
65                  70                  75                  80

Leu Glu Ile Val Glu Val Leu Leu Lys His Gly Ala Asp Val Asn Ala
                85                  90                  95

Ile Asp Met Arg Gly Thr Thr Pro Leu His Leu Ala Ala Pro Ala Gly
            100                 105                 110

His Leu Glu Ile Val Glu Val Leu Leu Lys Tyr Gly Ala Asp Val Asn
        115                 120                 125

Ala Asp Asp Val His Gly Asn Thr Pro Leu His Leu Ala Ala Met Ser
    130                 135                 140

Gly His Leu Glu Ile Val Glu Val Leu Leu Lys Tyr Gly Ala Asp Val
145                 150                 155                 160

Asn Ala Gln Asp Lys Phe Gly Lys Thr Ala Phe Asp Ile Ser Ile Asp
                165                 170                 175

Asn Gly Asn Glu Asp Leu Ala Glu Ile Leu Gln
            180                 185
```

<210> SEQ ID NO 46
<211> LENGTH: 154
<212> TYPE: PRT
<213> ORGANISM: Artificial Sequence
<220> FEATURE:
<223> OTHER INFORMATION: Synthetic DARPin B4_02

<400> SEQUENCE: 46

```
Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
            20                  25                  30

Asn Ala Gly Lys Thr Ala Leu His Leu Ala Ala Val Trp Gly His Leu
        35                  40                  45

Glu Ile Val Glu Val Leu Leu Lys Asn Gly Ala Asp Val Asn Ala Tyr
    50                  55                  60

Asp Ala Ser Gly Tyr Thr Leu Leu His Leu Ala Ala Arg Met Gly His
65                  70                  75                  80

Leu Glu Ile Val Glu Val Leu Leu Lys Tyr Gly Ala Asp Val Asn Ala
                85                  90                  95

Arg Asp Arg Phe Gly Ser Thr Pro Leu His Leu Ala Ala Trp His Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150
```

```
<210> SEQ ID NO 47
<211> LENGTH: 154
<212> TYPE: PRT
<213> ORGANISM: Artificial Sequence
<220> FEATURE:
<223> OTHER INFORMATION: Synthetic DARPin B4_07

<400> SEQUENCE: 47
```

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Arg Asp
            20                  25                  30

Val Phe Gly Trp Thr Pro Leu His Leu Ala Ala Val Asp Gly His Leu
        35                  40                  45

Glu Ile Val Glu Val Leu Leu Lys Tyr Gly Ala Asp Val Asn Ala Arg
    50                  55                  60

Asp Val Ala Gly Arg Thr Pro Leu His Leu Ala Ala Ser Phe Gly His
65                  70                  75                  80

Leu Glu Ile Val Glu Val Leu Leu Lys Tyr Gly Ala Asp Val Asn Ala
                85                  90                  95

Val Asp Tyr Thr Gly Thr Thr Pro Leu His Leu Ala Ala Trp His Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

```
<210> SEQ ID NO 48
<211> LENGTH: 154
<212> TYPE: PRT
<213> ORGANISM: Artificial Sequence
<220> FEATURE:
<223> OTHER INFORMATION: Synthetic DARPin B4_33

<400> SEQUENCE: 48
```

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Glu Asp
            20                  25                  30

Ala Thr Gly Phe Thr Pro Leu His Leu Ala Ala Val Trp Gly His Leu
        35                  40                  45

Glu Ile Val Glu Val Leu Leu Lys Asn Gly Ala Asp Val Asn Ala Asn
    50                  55                  60

Asp Gln Tyr Gly Tyr Thr Pro Leu His Leu Ala Ala Arg Met Gly His
65                  70                  75                  80

Leu Glu Ile Val Glu Val Leu Leu Lys His Gly Ala Asp Val Asn Ala
                85                  90                  95

Ile Asp Val Leu Gly Thr Thr Pro Leu His Leu Ala Ala Trp His Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln

-continued

```
145                 150

<210> SEQ ID NO 49
<211> LENGTH: 154
<212> TYPE: PRT
<213> ORGANISM: Artificial Sequence
<220> FEATURE:
<223> OTHER INFORMATION: Synthetic DARPin B4_45

<400> SEQUENCE: 49

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Arg Asp
                20                  25                  30

Asp Gly Gly Thr Thr Pro Leu His Leu Ala Ala Asn His Gly His Leu
            35                  40                  45

Glu Ile Val Glu Val Leu Leu Lys Tyr Gly Ala Asp Val Asn Ala Asn
    50                  55                  60

Asp Arg Tyr Gly Tyr Thr Thr Leu His Leu Ala Arg His Gly His
 65                  70                  75                  80

Leu Glu Ile Val Glu Val Leu Leu Lys His Gly Ala Asp Val Asn Ala
                85                  90                  95

Phe Asp Asn Thr Gly Gln Thr Pro Leu His Leu Ala Ala Trp His Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 50
<211> LENGTH: 187
<212> TYPE: PRT
<213> ORGANISM: Artificial Sequence
<220> FEATURE:
<223> OTHER INFORMATION: Synthetic DARPin B4_50

<400> SEQUENCE: 50

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala His Asp
                20                  25                  30

Arg Tyr Gly Val Thr Pro Leu His Leu Ala Ala Tyr Phe Gly His Leu
            35                  40                  45

Glu Ile Val Glu Val Leu Leu Lys Asn Gly Ala Asp Val Asn Ala Asp
    50                  55                  60

Asp His Asp Gly Tyr Thr Pro Leu His Leu Ala Ala Asp Lys Gly His
 65                  70                  75                  80

Leu Glu Ile Val Glu Val Leu Leu Lys His Gly Ala Asp Val Asn Ala
                85                  90                  95

Asp Asp Ser Met Gly Asn Thr Pro Leu His Leu Ala Ala Arg His Gly
            100                 105                 110

His Leu Glu Ile Val Glu Val Leu Leu Lys His Gly Ala Asp Val Asn
        115                 120                 125

Ala Asn Asp Phe Met Gly Ser Thr Pro Leu His Leu Ala Ala Trp Ser
    130                 135                 140
```

```
Gly His Leu Glu Ile Val Glu Val Leu Lys His Gly Ala Asp Val
145                 150                 155                 160

Asn Ala Gln Asp Lys Phe Gly Lys Thr Ala Phe Asp Ile Ser Ile Asp
                165                 170                 175

Asn Gly Asn Glu Asp Leu Ala Glu Ile Leu Gln
            180                 185
```

<210> SEQ ID NO 51
<211> LENGTH: 220
<212> TYPE: PRT
<213> ORGANISM: Artificial Sequence
<220> FEATURE:
<223> OTHER INFORMATION: Synthetic DARPin B4_58

<400> SEQUENCE: 51

```
Asp Leu Gly Lys Lys Leu Leu Glu Ala Thr Arg Ala Gly Gln Asp Asp
1               5                   10                  15

Glu Val Arg Ile Leu Met Ala Asn Gly Ala Asp Val Asn Ala Phe Asp
                20                  25                  30

Ser Asn Gly Ile Thr Pro Leu His Leu Ala Ala Phe Gly His Leu
                35                  40                  45

Glu Ile Val Glu Val Leu Leu Lys Asn Gly Ala Asp Val Asn Ala His
    50                  55                  60

Asp Ser Tyr Gly Ser Thr Pro Leu His Leu Ala Ala Asn Arg Gly His
65                  70                  75                  80

Leu Glu Ile Val Glu Val Leu Leu Lys Tyr Gly Ala Asp Val Asn Ala
                85                  90                  95

Phe Asp Ser Thr Gly Gln Thr Pro Leu His Leu Ala Ala Ser Gln Gly
                100                 105                 110

His Leu Glu Ile Val Glu Val Leu Leu Lys Tyr Gly Ala Asp Val Asn
                115                 120                 125

Ala Ser Asp Arg Met Gly Phe Thr Pro Leu His Leu Ala Ala Tyr Thr
130                 135                 140

Gly His Leu Glu Ile Val Glu Val Leu Leu Lys Asn Gly Ala Asp Val
145                 150                 155                 160

Asn Ala Lys Asp Phe Val Gly Trp Thr Pro Leu His Leu Ala Ala Tyr
                165                 170                 175

Arg Gly His Leu Glu Ile Val Glu Val Leu Leu Lys His Gly Ala Asp
                180                 185                 190

Val Asn Ala Gln Asp Lys Phe Gly Lys Thr Ala Phe Asp Ile Ser Ile
                195                 200                 205

Asp Asn Gly Asn Glu Asp Leu Ala Glu Ile Leu Gln
                210                 215                 220
```

<210> SEQ ID NO 52
<211> LENGTH: 154
<212> TYPE: PRT
<213> ORGANISM: Artificial Sequence
<220> FEATURE:
<223> OTHER INFORMATION: Synthetic DARPin I_01

<400> SEQUENCE: 52

```
Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asn Asp
                20                  25                  30

Ile Ser Gly Tyr Thr Pro Leu His Leu Ala Ala Tyr Val Gly His Gln
                35                  40                  45
```

```
Glu Ile Val Glu Val Leu Leu Lys Asn Gly Ala Asp Val Asn Ala Asp
 50                  55                  60
Asp Thr Trp Gly Asp Thr Pro Leu His Leu Ala Ala Leu Phe Gly His
 65                  70                  75                  80
Leu Glu Ile Val Glu Val Leu Leu Lys Tyr Gly Ala Asp Val Asn Ala
                 85                  90                  95
His Asp Arg Phe Gly Phe Thr Pro Leu His Leu Ala Ala Ser Ser Gly
                100                 105                 110
His Leu Glu Ile Val Glu Val Leu Leu Lys His Gly Ala Asp Val Asn
                115                 120                 125
Ala Gln Asp Lys Phe Gly Lys Thr Ala Phe Asp Ile Ser Ile Asp Asn
        130                 135                 140
Gly Asn Glu Asp Leu Ala Glu Ile Leu Gln
145                 150
```

<210> SEQ ID NO 53
<211> LENGTH: 121
<212> TYPE: PRT
<213> ORGANISM: Artificial Sequence
<220> FEATURE:
<223> OTHER INFORMATION: Synthetic DARPin I_02

<400> SEQUENCE: 53

```
Asp Leu Gly Lys Lys Leu Leu Glu Ala Ala Arg Ala Gly Gln Asp Asp
 1               5                  10                  15
Glu Val Arg Ile Leu Met Ala Asn Gly Ala Asp Val Asn Ala Arg Asp
                 20                  25                  30
Met Ser Gly Tyr Thr Pro Leu His Leu Ala Ala His Met Gly His Leu
             35                  40                  45
Glu Ile Val Glu Val Leu Leu Lys Asn Gly Ala Asp Val Asn Ala Lys
 50                  55                  60
Asp Asn Trp Gly Asp Thr Pro Leu His Leu Ala Ala Ile Phe Gly His
 65                  70                  75                  80
Leu Glu Ile Val Glu Val Leu Leu Lys Asn Gly Ala Asp Val Asn Ala
                 85                  90                  95
Gln Asp Lys Phe Gly Lys Thr Ala Phe Asp Ile Ser Ile Asp Asn Gly
                100                 105                 110
Asn Glu Asp Leu Ala Glu Ile Leu Gln
                115                 120
```

<210> SEQ ID NO 54
<211> LENGTH: 121
<212> TYPE: PRT
<213> ORGANISM: Artificial Sequence
<220> FEATURE:
<223> OTHER INFORMATION: Synthetic DARPin I_07

<400> SEQUENCE: 54

```
Asp Leu Gly Lys Lys Leu Leu Glu Ala Ala Arg Ala Gly Gln Asp Asp
 1               5                  10                  15
Glu Val Arg Ile Leu Met Ala Asn Gly Ala Asp Val Asn Ala Ser Asp
                 20                  25                  30
Lys Ser Gly Tyr Thr Pro Leu His Leu Ala Ala His Ile Gly His Leu
             35                  40                  45
Glu Ile Val Glu Val Leu Leu Lys His Gly Ala Asp Val Asn Ala His
 50                  55                  60
Asp Ser Trp Gly Asp Thr Pro Leu His Leu Ala Ala Thr Phe Gly His
```

```
                65                  70                  75                  80
Leu Glu Ile Val Glu Val Leu Lys His Gly Ala Asp Val Asn Ala
                        85                  90                  95

Gln Asp Lys Phe Gly Lys Thr Ala Phe Asp Ile Ser Ile Asp Asn Gly
            100                 105                 110

Asn Glu Asp Leu Ala Glu Ile Leu Gln
            115                 120

<210> SEQ ID NO 55
<211> LENGTH: 154
<212> TYPE: PRT
<213> ORGANISM: Artificial Sequence
<220> FEATURE:
<223> OTHER INFORMATION: Synthetic DARPin I_11

<400> SEQUENCE: 55

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Ile Asp
                20                  25                  30

Thr Ile Gly Leu Thr Pro Leu His Leu Ala Ala His Asp Gly His Leu
            35                  40                  45

Glu Ile Val Glu Val Leu Leu Lys Asn Gly Ala Asp Val Asn Ala Ala
        50                  55                  60

Asp Asn Trp Gly Ile Thr Pro Leu His Leu Ala Ala Arg Arg Gly His
 65                 70                  75                  80

Leu Glu Ile Val Glu Val Leu Lys His Gly Ala Asp Val Asn Ala
                    85                  90                  95

Asp Asp Val Gln Gly Asn Thr Pro Leu His Leu Thr Ala His His Gly
            100                 105                 110

His Leu Glu Ile Val Glu Val Leu Leu Lys His Gly Ala Asp Val Asn
                115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150

<210> SEQ ID NO 56
<211> LENGTH: 121
<212> TYPE: PRT
<213> ORGANISM: Artificial Sequence
<220> FEATURE:
<223> OTHER INFORMATION: Synthetic DARPin I_13

<400> SEQUENCE: 56

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Phe Asp
                20                  25                  30

Met Ser Gly Tyr Thr Pro Leu His Leu Ala Ala Tyr Asp Gly His Leu
            35                  40                  45

Glu Ile Val Glu Val Leu Leu Lys Asn Gly Ala Asp Val Asn Ala Asn
        50                  55                  60

Asp Leu Trp Gly Asp Thr Pro Leu His Leu Ala Ala Thr Arg Gly His
 65                 70                  75                  80

Leu Glu Ile Val Glu Val Leu Leu Lys Tyr Gly Ala Asp Val Asn Ala
                    85                  90                  95
```

```
Gln Asp Lys Phe Gly Lys Thr Ala Phe Asp Ile Ser Ile Asp Asn Gly
            100                 105                 110

Asn Glu Asp Leu Ala Glu Ile Leu Gln
        115                 120
```

<210> SEQ ID NO 57
<211> LENGTH: 154
<212> TYPE: PRT
<213> ORGANISM: Artificial Sequence
<220> FEATURE:
<223> OTHER INFORMATION: Synthetic DARPin I_19

<400> SEQUENCE: 57

```
Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Asp Asp
             20                  25                  30

Asn Lys Gly Asp Thr Pro Leu His Leu Ala Ala Ser Phe Gly His Leu
         35                  40                  45

Glu Ile Val Glu Val Leu Leu Lys Asn Gly Ala Asp Val Asn Ala Asp
     50                  55                  60

Asp Tyr Phe Gly Asp Thr Pro Leu His Leu Ala Ala Trp Ser Gly His
 65                  70                  75                  80

Leu Glu Ile Val Glu Val Leu Leu Lys Tyr Gly Ala Asp Val Asn Ala
                 85                  90                  95

Gln Asp Gln Arg Gly Phe Thr Pro Leu His Leu Ala Ala Ile Ala Gly
            100                 105                 110

His Leu Glu Ile Val Glu Val Leu Leu Lys Tyr Gly Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150
```

<210> SEQ ID NO 58
<211> LENGTH: 154
<212> TYPE: PRT
<213> ORGANISM: Artificial Sequence
<220> FEATURE:
<223> OTHER INFORMATION: Synthetic DARPin T_01

<400> SEQUENCE: 58

```
Asp Leu Gly Lys Lys Leu Leu Glu Ala Ala Arg Ala Asp Gln Asp Asp
 1               5                  10                  15

Glu Val Arg Ile Leu Met Ala Asn Gly Ala Asp Val Asn Ala Asn Asp
             20                  25                  30

Ile Trp Gly Ile Thr Pro Leu His Leu Ala Ala Ile Phe Gly His Leu
         35                  40                  45

Glu Ile Val Glu Phe Leu Leu Lys Asn Gly Ala Asp Val Asn Ala Ser
     50                  55                  60

Asp Phe Ser Gly Phe Thr Pro Leu His Leu Ala Ala Tyr Lys Gly His
 65                  70                  75                  80

Leu Glu Ile Val Glu Val Leu Leu Lys His Gly Ala Asp Val Asn Ala
                 85                  90                  95

Asn Asp Ala Thr Gly Thr Thr Pro Leu His Leu Ala Ala Lys Lys Gly
            100                 105                 110

His Leu Glu Ile Val Glu Val Leu Leu Lys Asn Gly Ala Asp Val Asn
            115                 120                 125
```

Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150

<210> SEQ ID NO 59
<211> LENGTH: 154
<212> TYPE: PRT
<213> ORGANISM: Artificial Sequence
<220> FEATURE:
<223> OTHER INFORMATION: Synthetic DARPin T_02

<400> SEQUENCE: 59

Asp Leu Gly Lys Lys Leu Leu Glu Val Ala Arg Ala Gly Gln Asp Asp
  1               5                  10                  15

Glu Val Arg Ile Leu Met Ala Asn Gly Ala Asp Val Asn Ala Ala Asp
                 20                  25                  30

His Gln Ser Phe Thr Pro Leu His Leu Tyr Ala Ile Phe Gly His Leu
             35                  40                  45

Glu Ile Val Glu Val Leu Leu Lys Asn Gly Ala Asp Val Asn Ala Ser
         50                  55                  60

Asp Trp His Gly Asn Thr Pro Leu His Leu Ala Ala Trp Ile Gly His
 65                  70                  75                  80

Leu Glu Ile Val Glu Val Leu Leu Lys Tyr Gly Ala Asp Val Asn Ala
                 85                  90                  95

Thr Asp His Ser Gly Ser Thr Pro Leu His Leu Ala Ala Thr Leu Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150

<210> SEQ ID NO 60
<211> LENGTH: 154
<212> TYPE: PRT
<213> ORGANISM: Artificial Sequence
<220> FEATURE:
<223> OTHER INFORMATION: Synthetic DARPin T_07

<400> SEQUENCE: 60

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Tyr Asp
                 20                  25                  30

Trp Lys Gly Leu Thr Pro Leu His Leu Ala Ala Ile Phe Gly His Leu
             35                  40                  45

Glu Ile Val Glu Ser Ala Met Lys Asn Gly Ala Asp Val Asn Ala Ile
         50                  55                  60

Asp Phe Ser Gly Arg Thr Pro Leu His Leu Ala Ala Leu Ile Gly His
 65                  70                  75                  80

Leu Glu Ile Val Glu Val Leu Leu Lys Tyr Gly Ala Asp Val Asn Ala
                 85                  90                  95

His Asp Ser Ala Gly Ser Thr Pro Leu His Leu Ala Ala Thr Lys Gly
            100                 105                 110

His Leu Glu Ile Val Glu Val Leu Leu Lys Tyr Gly Ala Asp Val Asn

```
                115                 120                 125
Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150

<210> SEQ ID NO 61
<211> LENGTH: 154
<212> TYPE: PRT
<213> ORGANISM: Artificial Sequence
<220> FEATURE:
<223> OTHER INFORMATION: Synthetic DARPin T_08

<400> SEQUENCE: 61

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Trp Asp
                20                  25                  30

Phe Leu Gly Leu Ile Pro Leu Arg Leu Ala Ala Ala Phe Gly His Leu
            35                  40                  45

Glu Ile Val Glu Val Leu Leu Lys Asn Gly Ala Asp Val Asn Ala Lys
        50                  55                  60

Asp Thr Tyr Gly Ile Thr Pro Leu His Leu Ala Ala Met Asn Gly His
65                  70                  75                  80

Leu Glu Ile Val Glu Val Leu Leu Lys Asn Gly Ala Asp Val Asn Ala
                85                  90                  95

Leu Asp Asn Thr Gly Ser Thr Pro Leu His Leu Ala Ala Asn Tyr Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150

<210> SEQ ID NO 62
<211> LENGTH: 154
<212> TYPE: PRT
<213> ORGANISM: Artificial Sequence
<220> FEATURE:
<223> OTHER INFORMATION: Synthetic DARPin T_09

<400> SEQUENCE: 62

Asp Leu Gly Lys Lys Leu Leu Glu Ala Ala Arg Ala Ser Gln Asp Asp
1               5                   10                  15

Glu Val Arg Ile Leu Met Ala Asn Gly Ala Asp Val Asn Ala Asn Asp
                20                  25                  30

Phe Gln Gly Ile Thr Pro Leu His Leu Ala Ala Ile Phe Gly His Leu
            35                  40                  45

Glu Ile Val Glu Val Leu Leu Lys Asn Gly Ala Asp Val Asn Ala Tyr
        50                  55                  60

Asp Gln Met Gly Met Thr Pro Leu His Leu Ala Ala Trp Thr Gly His
65                  70                  75                  80

Leu Glu Ile Val Glu Val Leu Leu Lys His Gly Ala Asp Val Asn Ala
                85                  90                  95

Asp Asp Thr His Gly Ala Thr Pro Leu His Leu Ala Ala His Thr Gly
            100                 105                 110
```

```
His Leu Glu Ile Val Glu Val Leu Lys Tyr Gly Ala Asp Val Asn
            115                 120                 125

Ala Gln Asp Lys Phe Gly Lys Thr Ala Phe Asp Ile Ser Ile Asp Asn
130                 135                 140

Gly Asn Glu Asp Leu Ala Glu Ile Leu Gln
145                 150

<210> SEQ ID NO 63
<211> LENGTH: 154
<212> TYPE: PRT
<213> ORGANISM: Artificial Sequence
<220> FEATURE:
<223> OTHER INFORMATION: Synthetic DARPin T_16

<400> SEQUENCE: 63

Asp Leu Gly Lys Lys Pro Leu Glu Ala Ala Arg Ala Gly Gln Asp Asp
1               5                   10                  15

Glu Val Arg Ile Leu Met Ala Asn Gly Ala Asp Val Asn Ala Tyr Asp
            20                  25                  30

Ile Val Gly Ile Thr Pro Leu His Leu Ala Ala Ile Phe Gly His Leu
        35                  40                  45

Glu Ile Val Glu Val Leu Leu Lys Asn Gly Ala Asp Val Asn Ala Tyr
 50                  55                  60

Asp Met Gln Val Asn Thr Pro Leu His Leu Ala Ala Trp Leu Gly His
65                  70                  75                  80

Leu Glu Ile Val Glu Val Leu Leu Lys Asn Gly Ala Asp Val Asn Ala
                85                  90                  95

Glu Asp Ser Tyr Gly Asn Thr Pro Leu His Leu Ala Ala Asp Lys Gly
            100                 105                 110

His Leu Glu Ile Val Glu Val Leu Leu Lys Asn Gly Ala Asp Val Asn
            115                 120                 125

Ala Gln Asp Lys Phe Gly Lys Thr Ala Phe Asp Ile Ser Ile Asp Asn
130                 135                 140

Gly Asn Glu Asp Leu Ala Glu Ile Leu Gln
145                 150

<210> SEQ ID NO 64
<211> LENGTH: 154
<212> TYPE: PRT
<213> ORGANISM: Artificial Sequence
<220> FEATURE:
<223> OTHER INFORMATION: Synthetic DARPin T_25

<400> SEQUENCE: 64

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asp Asp
            20                  25                  30

Arg Arg Gly Ile Pro Pro Leu His Leu Ala Ala Ile Phe Gly His Leu
        35                  40                  45

Glu Ile Val Glu Val Leu Leu Lys His Gly Ala Asp Val Asn Ala His
 50                  55                  60

Asp Met Gln Gly Arg Thr Pro Leu His Leu Ala Ala Tyr Thr Gly His
65                  70                  75                  80

Leu Glu Ile Val Glu Val Leu Leu Lys Tyr Gly Ala Asp Val Asn Ala
                85                  90                  95

Ile Asp Phe Thr Gly His Thr Pro Leu His Leu Ala Ala Phe Arg Gly
            100                 105                 110
```

His Leu Glu Ile Val Glu Val Leu Lys His Gly Ala Asp Val Asn
         115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 65
<211> LENGTH: 154
<212> TYPE: PRT
<213> ORGANISM: Artificial Sequence
<220> FEATURE:
<223> OTHER INFORMATION: Synthetic DARPin T_27

<400> SEQUENCE: 65

Asp Leu Gly Lys Lys Pro Leu Glu Ala Ala Arg Ala Gly Gln Asp Asp
 1               5                  10                  15

Glu Val Arg Ile Leu Met Ala Asn Gly Ala Asp Val Asn Ala Tyr Asp
             20                  25                  30

Arg His Gly Leu Thr Pro Leu His Leu Val Ala Ile Phe Gly His Leu
         35                  40                  45

Glu Ile Val Glu Val Leu Leu Lys His Gly Ala Asp Val Asn Ala Ile
     50                  55                  60

Asp Ile Ile Gly Tyr Thr Pro Leu His Leu Ala Ala Trp Ser Gly His
 65                  70                  75                  80

Leu Glu Ile Val Glu Val Leu Leu Lys Asn Gly Ala Asp Val Asn Ala
                 85                  90                  95

Ser Asp Val Thr Gly Ser Thr Pro Leu His Leu Ala Ala Asp Lys Gly
            100                 105                 110

His Leu Glu Ile Val Glu Val Leu Leu Lys Tyr Gly Ala Asp Val Asn
         115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 66
<211> LENGTH: 154
<212> TYPE: PRT
<213> ORGANISM: Artificial Sequence
<220> FEATURE:
<223> OTHER INFORMATION: Synthetic DARPin T_37

<400> SEQUENCE: 66

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala His Asp
             20                  25                  30

Lys Arg Gly Ile Thr Pro Leu His Leu Ala Ala Ile Thr Gly His Leu
         35                  40                  45

Glu Met Val Glu Val Leu Leu Lys His Gly Ala Asp Val Asn Ala Val
     50                  55                  60

Asp Ile Gln Gly Arg Thr Pro Leu His Leu Ala Ala Trp Ile Gly His
 65                  70                  75                  80

Leu Glu Ile Val Glu Val Leu Leu Lys Tyr Gly Ala Asp Val Asn Ala
                 85                  90                  95

Met Asp Asp Phe Gly Glu Thr Pro Leu His Leu Ala Ala Arg Thr Gly

```
                100                 105                 110
His Leu Glu Ile Val Glu Val Leu Leu Lys His Gly Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150

<210> SEQ ID NO 67
<211> LENGTH: 154
<212> TYPE: PRT
<213> ORGANISM: Artificial Sequence
<220> FEATURE:
<223> OTHER INFORMATION: Synthetic DARPin T_40

<400> SEQUENCE: 67

Asp Leu Gly Lys Lys Leu Leu Glu Ala Ala Arg Ala Ser Gln Asp Asp
  1               5                  10                  15

Glu Val Arg Ile Leu Met Ala Asn Gly Ala Asp Val Asn Ala Asn Asp
             20                  25                  30

Arg Val Gly Phe Thr Pro Leu His Leu Ala Ala Met Phe Gly His Leu
         35                  40                  45

Glu Leu Val Glu Val Leu Leu Lys Asn Gly Ala Asp Val Asn Ala Ile
     50                  55                  60

Asp Phe Gln Gly Lys Thr Pro Leu His Leu Ala Ala Gln Leu Gly His
 65                  70                  75                  80

Leu Glu Ile Val Glu Val Leu Leu Lys Tyr Gly Ala Asp Val Asn Ala
                 85                  90                  95

Leu Asp Ala Arg Gly Ile Thr Pro Leu His Leu Ala Ala Ile His Gly
            100                 105                 110

His Pro Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 68
<211> LENGTH: 220
<212> TYPE: PRT
<213> ORGANISM: Artificial Sequence
<220> FEATURE:
<223> OTHER INFORMATION: Synthetic DARPin
<220> FEATURE:
<221> NAME/KEY: MOD_RES
<222> LOCATION: (1)..(220)
<223> OTHER INFORMATION: each Xaa is independently Ala, Ile, Leu, Met,
      Phe, Pro, Trp, Val, Asn, Cys, Gln, Gly, Ser, Thr, Tyr, Asp, Glu,
      Arg, His or Lys

<400> SEQUENCE: 68

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Xaa Asp
             20                  25                  30

Xaa Xaa Gly Xaa Thr Pro Leu His Leu Ala Ala Xaa Xaa Gly His Leu
         35                  40                  45

Glu Ile Val Glu Val Leu Leu Lys Xaa Gly Ala Asp Val Asn Ala Xaa
     50                  55                  60
```

-continued

```
Asp Xaa Xaa Gly Xaa Thr Pro Leu His Leu Ala Ala Xaa Xaa Gly His
 65                 70                  75                  80

Leu Glu Ile Val Glu Val Leu Leu Lys Xaa Gly Ala Asp Val Asn Ala
                85                  90                  95

Xaa Asp Xaa Xaa Gly Xaa Thr Pro Leu His Leu Ala Ala Xaa Xaa Gly
            100                 105                 110

His Leu Glu Ile Val Glu Val Leu Leu Lys Xaa Gly Ala Asp Val Asn
        115                 120                 125

Ala Xaa Asp Xaa Xaa Gly Xaa Thr Pro Leu His Leu Ala Ala Xaa Xaa
    130                 135                 140

Gly His Leu Glu Ile Val Glu Val Leu Leu Lys Xaa Gly Ala Asp Val
145                 150                 155                 160

Asn Ala Xaa Asp Xaa Xaa Gly Xaa Thr Pro Leu His Leu Ala Ala Xaa
                165                 170                 175

Xaa Gly His Leu Glu Ile Val Glu Val Leu Leu Lys Xaa Gly Ala Asp
            180                 185                 190

Val Asn Ala Gln Asp Lys Phe Gly Lys Thr Ala Phe Asp Ile Ser Ile
        195                 200                 205

Asp Asn Gly Asn Glu Asp Leu Ala Glu Ile Leu Gln
    210                 215                 220
```